(12) United States Patent
Leung et al.

(10) Patent No.: US 8,507,245 B2
(45) Date of Patent: Aug. 13, 2013

(54) SITE-DIRECTED PEGYLATION OF ARGINASES AND THE USE THEREOF AS ANTI-CANCER AND ANTI-VIRAL AGENTS

(75) Inventors: Yun Chung Leung, Hong Kong (CN);
Wai-hung Lo, Hong Kong (CN)

(73) Assignee: The Hong Kong Polytechnic University, Hunghom, Kowloon (HK)

( * ) Notice: Subject to any disclaimer, the term of this patent is extended or adjusted under 35 U.S.C. 154(b) by 572 days.

(21) Appl. No.: 12/732,188

(22) Filed: Mar. 26, 2010

(65) Prior Publication Data
US 2010/0247508 A1  Sep. 30, 2010

Related U.S. Application Data

(60) Provisional application No. 61/163,863, filed on Mar. 26, 2009.

(51) Int. Cl.
*C12N 9/78* (2006.01)
*C07K 14/00* (2006.01)
*C12P 21/00* (2006.01)

(52) U.S. Cl.
USPC .......... 435/227; 435/69.1; 530/350; 930/240; 930/320

(58) Field of Classification Search
USPC .................. 435/227; 530/350; 930/240, 320
See application file for complete search history.

(56) References Cited

U.S. PATENT DOCUMENTS 5,766,897 A   6/1998   Braxton

FOREIGN PATENT DOCUMENTS

| WO | WO 03/063780 | * | 8/2003 |
|---|---|---|---|
| WO | 2004000349 A1 | | 12/2003 |
| WO | 2004001048 A1 | | 12/2003 |
| WO | 2004022004 A2 | | 3/2004 |
| WO | 2006026915 A1 | | 3/2006 |
| WO | 2006058486 A1 | | 6/2006 |
| WO | 2011/008495 A2 | | 1/2011 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Di Constanzo et al., PNAS 102(37):13058-13063, 2005.*
Bewley et al., Structure 7(4):435-448, 1999.*
Stone et al., Journal of Controlled Release 158:171-179, 2012.*
Paul Ning-Man Cheng et al., Pegylated Recombinant Human Arginase Inhibits the in vitro and in vivo Proliferation of Human Hepatocellular Carcinoma through Arginine Depletion. Cancer Res. Jan. 1, 2007; 67: (1), pp. 309-317.
International Search Report & Written Opinion of PCT/CN2010/071357 dated Jul. 8, 2010.
K. V. Savoca et al., "Preparation of a non-immunogenic arginase by the covalent attachment of polyethylene glycol", Biochimica et Biophysica Acta, 578, p. 47-53, 1979.
K. V. Savoca et al., "Cancer therapy with chemically modified enzymes. II. The therapeutic effectiveness of arginase, and arginase modified by the covalent attachment of polyethylene glycol, on the taper liver tumor and the L5178Y murine leukemia", Cancer Biochem Biophys., vol. 7, p. 261-268, 1984.
Daniel H. Doherty et al., "Site-specific PEGylation of engineered cysteine analogues of recombinant human granulocyte-macrophage colony-stimulating factor", Bioconjugate Chem, 16, p. 1291-1298, 2005.
The extended European Search Report of EP10769236.0 dated Aug. 10, 2012.

* cited by examiner

*Primary Examiner* — Delia Ramirez
(74) *Attorney, Agent, or Firm* — Ella Cheong Hong Kong; Sam T. Yip

(57) ABSTRACT

Mono-pegylated arginase conjugate and method producing thereof. The mono-pegylated arginase is homogeneous in molecular weight and shows therapeutic effect for treating cancers and viral infections. The method of producing such arginase conjugate has a main step of genetically modifying the gene encoding an arginase so that the PEG moiety can attach to the enzyme at a predetermined, specific intended site. This is achieved by removing the PEG attaching amino acid residues at undesirable sites while keeping (or adding, if necessary) the one at the desirable site of the enzyme. Two exemplary mono-pegylated arginase conjugates so produced are human arginase I (HAI) where a polyethylene glycol (PEG) moiety is site-specific covalently bonded to $Cys^{45}$ of the enzyme and *Bacillus caldovelox* arginase (BCA) where a polyethylene glycol (PEG) moiety is site-specific covalently bonded to $Cys^{161}$ of the enzyme.

10 Claims, 30 Drawing Sheets

FIG. 1A

```
ATGAGCGCCAAGTCCAGAACCATAGGGATTATTGGAGCTCCTTTCTCAAAGGGACAGCCA 60
CGAGGAGGGTGGAAGAAGGCCCTACAGTATTGAGAAAGGCTGGTCTGCTTGAGAAACTT 120
AAAGAACAAGAGTGTGATGTGAAGGATTATGGGACCTGCCCTTTGCTGACATCCCTAAT 180
GACAGTCCCTTTCAAATTGTGAAGAATCCAAGGTCTGTGGGAAAAGCAAGCGAGCAGCTG 240
GCTGGCAAGGTGGCAGAAGTCAAGAAGAACGGAAGAATCAGCCTGGTGCTGGGCGGAGAC 300
CACAGTTTGGCAATTGGAAGCATCTCTGGCCATGCCAGGGTCCACCCTGATCTTGGAGTC 360
ATCTGGGTGGATGCTCACACTGATATCAACACTCCACTGACAACCACAAGTGGAAACTTG 420
CATGGACAACCTGTATCTTTCCTCCTGAAGGAACTAAAAGGAAAGATTCCCGATGTGCCA 480
GGATTCTCCTGGGTGACTCCCTGTATATCTGCCAAGGATATTGTGTATATTGGCTTGAGA 540
GACGTGGACCCTGGGGAACACTACATTTTGAAAACTCTAGGCATTAAATACTTTTCAATG 600
ACTGAAGTGGACAGACTAGGAATTGGCAAGGTGATGGAAGAAACACTCAGCTATCTACTA 660
GGAAGAAAGAAAAGGCCAATTCATCTAAGTTTTGATGTTGACGGACTGGACCCATCTTTC 720
ACACCAGCTACTGGCACACCAGTCGTGGGAGGTCTGACATACAGAGAAGGTCTCTACATC 780
ACAGAAGAAATCTACAAAACAGGGCTACTCTCAGGATTAGATATAATGGAAGTGAACCCA 840
TCCCTGGGGAAGACACCAGAAGAAGTAACTCGAACAGTGAACACAGCAGTTGCAATAACC 900
TTGGCTTGTTTCGGACTTGCTCGGGAGGGTAATCACAAGCCTATTGACTACCTTAACCCA 960
CCTAAGTAA 969
```

FIG. 1b

```
ATGAGCGCCAAGTCCAGAACCATAGGGATTATTGGAGCTCCTTTCTCAAAGGGACAGCCA 60
CGAGGAGGGTGGAAGAAGGCCCTACAGTATTGAGAAAGGCTGGTCTGCTTGAGAAACTT 120
AAAGAACAAGAGTGTGATGTGAAGGATTATGGGACCTGCCCTTTGCTGACATCCCTAAT 180
GACAGTCCCTTTCAAATTGTGAAGAATCCAAGGTCTGTGGGAAAAGCAAGCGAGCAGCTG 240
GCTGGCAAGGTGGCAGAAGTCAAGAAGAACGGAAGAATCAGCCTGGTGCTGGGCGGAGAC 300
CACAGTTTGGCAATTGGAAGCATCTCTGGCCATGCCAGGGTCCACCCTGATCTTGGAGTC 360
ATCTGGGTGGATGCTCACACTGATATCAACACTCCACTGACAACCACAAGTGGAAACTTG 420
CATGGACAACCTGTATCTTTCCTCCTGAAGGAACTAAAAGGAAAGATTCCCGATGTGCCA 480
GGATTCTCCTGGGTGACTCCCTCTATATCTGCCAAGGATATTGTGTATATTGGCTTGAGA 540
GACGTGGACCCTGGGGAACACTACATTTTGAAAACTCTAGGCATTAAATACTTTTCAATG 600
ACTGAAGTGGACAGACTAGGAATTGGCAAGGTGATGGAAGAAACACTCAGCTATCTACTA 660
GGAAGAAAGAAAAGGCCAATTCATCTAAGTTTTGATGTTGACGGACTGGACCCATCTTTC 720
ACACCAGCTACTGGCACACCAGTCGTGGGAGGTCTGACATACAGAGAAGGTCTCTACATC 780
ACAGAAGAAATCTACAAAACAGGGCTACTCTCAGGATTAGATATAATGGAAGTGAACCCA 840
TCCCTGGGGAAGACACCAGAAGAAGTAACTCGAACAGTGAACACAGCAGTTGCAATAACC 900
TTGGCTTCTTTCGGACTTGCTCGGGAGGGTAATCACAAGCCTATTGACTACCTTAACCCA 960
CCTAAGTAA 969
```

FIG. 1c

```
ATGAAGCCAATTTCAATTATCGGGGTTCCGATGGATTTAGGGCAGACACG  50
CCGCGGCGTTGATATGGGGCCGAGCGCAATGCGTTATGCAGGCGTCATCG 100
AACGTCTGGAACGTCTTCATTACGATATTGAAGATTTGGGAGATATTCCG 150
ATTGGAAAAGCAGAGCGGTTGCACGAGCAAGGAGATTCACGGTTGCGCAA 200
TTTGAAAGCGGTTGCGGAAGCGAACGAGAAACTTGCGGCGGCGGTTGACC 250
AAGTCGTTCAGCGGGGCGATTTCCGCTTGTGTTGGGCGGCGACCATAGC  300
ATCGCCATTGGCACGCTCGCCGGGGTGGCGAAACATTATGAGCGGCTTGG 350
AGTGATCTGGTATGACGCGCATGGCGACGTCAACACCGCGGAAACGTCGC 400
CGTCTGGAAACATTCATGGCATGCCGCTGGCGGCGAGCCTCGGGTTTGGC 450
CATCCGGCGCTGACGCAAATCGGCGGATACAGCCCCAAAATCAAGCCGGA 500
ACATGTCGTGTTGATCGGCGTCCGTTCCCTTGATGAAGGGGAGAAGAAGT 550
TTATTCGCGAAAAGGAATCAAAATTTACACGATGCATGAGGTTGATCGG  600
CTCGGAATGACAAGGGTGATGGAAGAAACGATCGCCTATTTAAAAGAACG 650
AACGGATGGCGTTCATTTGTCGCTTGACTTGGATGGCCTTGACCCAAGCG 700
ACGCACCGGGAGTCGGAACGCCTGTCATTGGAGGATTGACATACCGCGAA 750
AGCCATTTGGCGATGGAGATGCTGGCCGAGGCACAAATCATCACTTCAGC 800
GGAATTTGTCGAAGTGAACCCGATCTTGGATGAGCGGAACAAAACAGCAT 850
CAGTGGCTGTAGCGCTGATGGGGTCGTTGTTTGGTGAAAAACTCATGTAA 900
```

FIG. 1d

```
ATGAAGCCAATTTCAATTATCGGGGTTCCGATGGATTTAGGGCAGACACG  50
CCGCGGCGTTGATATGGGGCCGAGCGCAATGCGTTATGCAGGCGTCATCG 100
AACGTCTGGAACGTCTTCATTACGATATTGAAGATTTGGGAGATATTCCG 150
ATTGGAAAAGCAGAGCGGTTGCACGAGCAAGGAGATTCACGGTTGCGCAA 200
TTTGAAAGCGGTTGCGGAAGCGAACGAGAAACTTGCGGCGGCGGTTGACC 250
AAGTCGTTCAGCGGGGCGATTTCCGCTTGTGTTGGGCGGCGACCATAGC  300
ATCGCCATTGGCACGCTCGCCGGGGTGGCGAAACATTATGAGCGGCTTGG 350
AGTGATCTGGTATGACGCGCATGGCGACGTCAACACCGCGGAAACGTCGC 400
CGTCTGGAAACATTCATGGCATGCCGCTGGCGGCGAGCCTCGGGTTTGGC 450
CATCCGGCGCTGACGCAAATCGGCGGATACTGCCCCAAAATCAAGCCGGA 500
ACATGTCGTGTTGATCGGCGTCCGTTCCCTTGATGAAGGGGAGAAGAAGT 550
TTATTCGCGAAAAGGAATCAAAATTTACACGATGCATGAGGTTGATCGG  600
CTCGGAATGACAAGGGTGATGGAAGAAACGATCGCCTATTTAAAAGAACG 650
AACGGATGGCGTTCATTTGTCGCTTGACTTGGATGGCCTTGACCCAAGCG 700
ACGCACCGGGAGTCGGAACGCCTGTCATTGGAGGATTGACATACCGCGAA 750
AGCCATTTGGCGATGGAGATGCTGGCCGAGGCACAAATCATCACTTCAGC 800
GGAATTTGTCGAAGTGAACCCGATCTTGGATGAGCGGAACAAAACAGCAT 850
CAGTGGCTGTAGCGCTGATGGGGTCGTTGTTTGGTGAAAAACTCATGCAT 900
CACCATCACCATCACTAA 918
```

FIG. 2a

```
MSAKSRTIGIIGAPFSKGQPRGGVEEGPTVLRKAGLLEKLKEQECDVKDYGDLPFADIPN  60
DSPFQIVKNPRSVGKASEQLAGKVAEVKKNGRISLVLGGDHSLAIGSISGHARVHPDLGV 120
IWVDAHTDINTPLTTTSGNLHGQPVSFLLKELKGKIPDVPGFSWVTPCISAKDIVYIGLR 180
DVDPGEHYILKTLGIKYFSMTEVDRLGIGKVMEETLSYLLGRKKRPIHLSFDVDGLPSF  240
TPATGTPVVGGLTYREGLYITEEIYKTGLLSGLDIMEVNPSLGKTPEEVTRTVNTAVAIT 300
LACFGLAREGNHKPIDYLNPPK 322
```

FIG. 2b

```
MSAKSRTIGIIGAPFSKGQPRGGVEEGPTVLRKAGLLEKLKEQECDVKDYGDLPFADIPN  60

DSPFQIVKNPRSVGKASEQLAGKVAEVKKNGRISLVLGGDHSLAIGSISGHARVHPDLGV 120

IWVDAHTDINTPLTTTSGNLHGQPVSFLLKELKGKIPDVPGFSWVTPSISAKDIVYIGLR 180

DVDPGEHYILKTLGIKYFSMTEVDRLGIGKVMEETLSYLLGRKKRPIHLSFDVDGLPSF  240

TPATGTPVVGGLTYREGLYITEEIYKTGLLSGLDIMEVNPSLGKTPEEVTRTVNTAVAIT 300

LASFGLAREGNHKPIDYLNPPK 322
```

FIG. 2c

```
MKPISIIGVPMDLGQTRRGVDMGPSAMRYAGVIERLERLHYDIEDLGDIP  50
IGKAERLHEQGDSRLRNLKAVAEANEKLAAAVDQVVQRGRFPLVLGGDHS 100
IAIGTLAGVAKHYERLGVIWYDAHGDVNTAETSPSGNIHGMPLAASLGFG 150
HPALTQIGGYSPKIKPEHVVLIGVRSLDEGEKKFIREKGIKIYTMHEVDR 200
LGMTRVMEETIAYLKERTDGVHLSLDLDGLDPSDAPGVGTPVIGGLTYRE 250
SHLAMEMLAEAQIITSAEFVEVNPILDERNKTASVAVALMGSLFGEKLM  299
```

FIG. 2d

```
MKPISIIGVPMDLGQTRRGVDMGPSAMRYAGVIERLERLHYDIEDLGDIP  50
IGKAERLHEQGDSRLRNLKAVAEANEKLAAAVDQVVQRGRFPLVLGGDHS 100
IAIGTLAGVAKHYERLGVIWYDAHGDVNTAETSPSGNIHGMPLAASLGFG 150
HPALTQIGGYCPKIKPEHVVLIGVRSLDEGEKKFIREKGIKIYTMHEVDR 200
LGMTRVMEETIAYLKERTDGVHLSLDLDGLDPSDAPGVGTPVIGGLTYRE 250
SHLAMEMLAEAQIITSAEFVEVNPILDERNKTASVAVALMGSLFGEKLMH 300
HHHHH 305
```

FIG. 3a

```
atgagcgccaagtccagaaccatagggattattggagctcctttctcaaagggacagcca
 M  S  A  K  S  R  T  I  G  I  I  G  A  P  F  S  K  G  Q  P
cgaggagggggtggaagaaggccctacagtattgagaaaggctggtctgcttgagaaactt
 R  G  G  V  E  E  G  P  T  V  L  R  K  A  G  L  L  E  K  L
aaagaacaagagtgtgatgtgaaggattatggggacctgccctttgctgacatccctaat
 K  E  Q  E  C  D  V  K  D  Y  G  D  L  P  F  A  D  I  P  N
gacagtccctttcaaattgtgaagaatccaaggtctgtgggaaaagcaagcgagcagctg
 D  S  P  F  Q  I  V  K  N  P  R  S  V  G  K  A  S  E  Q  L
gctggcaaggtggcagaagtcaagaagaacggaagaatcagcctggtgctgggcggagac
 A  G  K  V  A  E  V  K  K  N  G  R  I  S  L  V  L  G  G  D
cacagtttggcaattggaagcatctctggccatgccagggtccaccctgatcttggagtc
 H  S  L  A  I  G  S  I  S  G  H  A  R  V  H  P  D  L  G  V
atctgggtggatgctcacactgatatcaacactccactgacaaccacaagtggaaacttg
 I  W  V  D  A  H  T  D  I  N  T  P  L  T  T  T  S  G  N  L
catggacaacctgtatctttcctcctgaaggaactaaaaggaaagattcccgatgtgcca
 H  G  Q  P  V  S  F  L  L  K  E  L  K  G  K  I  P  D  V  P
ggattctcctgggtgactccctctatatctgccaaggatattgtgtatattggcttgaga
 G  F  S  W  V  T  P  S  I  S  A  K  D  I  V  Y  I  G  L  R
gacgtggaccctggggaacactacattttgaaaactctaggcattaaatacttttcaatg
 D  V  D  P  G  E  H  Y  I  L  K  T  L  G  I  K  Y  F  S  M
actgaagtggacagactaggaattggcaaggtgatggaagaaacactcagctatctacta
 T  E  V  D  R  L  G  I  G  K  V  M  E  E  T  L  S  Y  L  L
ggaagaaagaaaaggccaattcatctaagttttgatgttgacggactggacccatctttc
 G  R  K  K  R  P  I  H  L  S  F  D  V  D  G  L  D  P  S  F
acaccagctactggcacaccagtcgtgggaggtctgacatacagagaaggtctctacatc
 T  P  A  T  G  T  P  V  V  G  G  L  T  Y  R  E  G  L  Y  I
acagaagaaatctacaaaacagggctactctcaggattagatataatggaagtgaaccca
 T  E  E  I  Y  K  T  G  L  L  S  G  L  D  I  M  E  V  N  P
tccctggggaagacaccagaagaagtaactcgaacagtgaacacagcagttgcaataacc
 S  L  G  K  T  P  E  E  V  T  R  T  V  N  T  A  V  A  I  T
ttggcttcttttcggacttgctcgggagggtaatcacaagcctattgactaccttaaccca
 L  A  S  F  G  L  A  R  E  G  N  H  K  P  I  D  Y  L  N  P
cctaagtaa
 P  K  -
```

FIG. 3b

```
atgcatcaccatcaccatcacatgagcgccaagtccagaaccatagggattattggagct
 M  H  H  H  H  H  H  M  S  A  K  S  R  T  I  G  I  I  G  A
cctttctcaaagggacagccacgaggaggggtggaagaaggccctacagtattgagaaag
 P  F  S  K  G  Q  P  R  G  G  V  E  E  G  P  T  V  L  R  K
gctggtctgcttgagaaacttaaagaacaagagtgtgatgtgaaggattatggggacctg
 A  G  L  L  E  K  L  K  E  Q  E  C  D  V  K  D  Y  G  D  L
ccctttgctgacatccctaatgacagtcccttcaaattgtgaagaatccaaggtctgtg
 P  F  A  D  I  P  N  D  S  P  F  Q  I  V  K  N  P  R  S  V
ggaaaagcaagcgagcagctggctggcaaggtggcagaagtcaagaagaacggaagaatc
 G  K  A  S  E  Q  L  A  G  K  V  A  E  V  K  K  N  G  R  I
agcctggtgctgggcggagaccacagtttggcaattggaagcatctctggccatgccagg
 S  L  V  L  G  G  D  H  S  L  A  I  G  S  I  S  G  H  A  R
gtccaccctgatcttggagtcatctgggtggatgctcacactgatatcaacactccactg
 V  H  P  D  L  G  V  I  W  V  D  A  H  T  D  I  N  T  P  L
acaaccacaagtggaaacttgcatggacaacctgtatctttcctcctgaaggaactaaaa
 T  T  T  S  G  N  L  H  G  Q  P  V  S  F  L  L  K  E  L  K
ggaaagattcccgatgtgccaggattctcctgggtgactccctctatatctgccaaggat
 G  K  I  P  D  V  P  G  F  S  W  V  T  P  S  I  S  A  K  D
attgtgtatattggcttgagagacgtggaccctggggaacactacattttgaaaactcta
 I  V  Y  I  G  L  R  D  V  D  P  G  E  H  Y  I  L  K  T  L
ggcattaaatacttttcaatgactgaagtggacagactaggaattggcaaggtgatggaa
 G  I  K  Y  F  S  M  T  E  V  D  R  L  G  I  G  K  V  M  E
gaaacactcagctatctactaggaagaaagaaaaggccaattcatctaagttttgatgtt
 E  T  L  S  Y  L  L  G  R  K  K  R  P  I  H  L  S  F  D  V
gacggactggacccatctttcacaccagctactggcacaccagtcgtgggaggtctgaca
 D  G  L  D  P  S  F  T  P  A  T  G  T  P  V  V  G  G  L  T
tacagagaaggtctctacatcacagaagaaatctacaaaacagggctactctcaggatta
 Y  R  E  G  L  Y  I  T  E  E  I  Y  K  T  G  L  L  S  G  L
gatataatggaagtgaacccatccctggggaagacaccagaagaagtaactcgaacagtg
 D  I  M  E  V  N  P  S  L  G  K  T  P  E  E  V  T  R  T  V
aacacagcagttgcaataaccttggcttctttcggacttgctcgggagggtaatcacaag
 N  T  A  V  A  I  T  L  A  S  F  G  L  A  R  E  G  N  H  K
cctattgactaccttaacccacctaagtaa
 P  I  D  Y  L  N  P  P  K  -
```

FIG. 3c

```
atgaagccaatttcaattatcggggttccgatggatttagggcagacacgccgcggcgtt
 M  K  P  I  S  I  I  G  V  P  M  D  L  G  Q  T  R  R  G  V
gatatggggccgagcgcaatgcgttatgcaggcgtcatcgaacgtctggaacgtcttcat
 D  M  G  P  S  A  M  R  Y  A  G  V  I  E  R  L  E  R  L  H
tacgatattgaagatttggagatattccgattggaaaagcagagcggttgcacgagcaa
 Y  D  I  E  D  L  G  D  I  P  I  G  K  A  E  R  L  H  E  Q
ggagattcacggttgcgcaatttgaaagcggttgcggaagcgaacgagaaacttgcggcg
 G  D  S  R  L  R  N  L  K  A  V  A  E  A  N  E  K  L  A  A
gcggttgaccaagtcgttcagcggggcgatttccgcttgtgttgggcggcgaccatagc
 A  V  D  Q  V  V  Q  R  G  R  F  P  L  V  L  G  D  H  S
atcgccattggcacgctcgccggggtggcgaaacattatgagcggcttggagtgatctgg
 I  A  I  G  T  L  A  G  V  A  K  H  Y  E  R  L  G  V  I  W
tatgacgcgcatggcgacgtcaacaccgcggaaacgtcgccgtctggaaacattcatggc
 Y  D  A  H  G  D  V  N  T  A  E  T  S  P  S  G  N  I  H  G
atgccgctggcggcgagcctcgggtttggccatccggcgctgacgcaaatcggcggatac
 M  P  L  A  A  S  L  G  F  G  H  P  A  L  T  Q  I  G  G  Y
tgccccaaaatcaagccggaacatgtcgtgttgatcggcgtccgttcccttgatgaaggg
 C  P  K  I  K  P  E  H  V  V  L  I  G  V  R  S  L  D  E  G
gagaagaagtttattcgcgaaaaggaatcaaaatttacacgatgcatgaggttgatcgg
 E  K  K  F  I  R  E  K  G  I  K  I  Y  T  M  H  E  V  D  R
ctcggaatgacaagggtgatggaagaaacgatcgcctatttaaaagaacgaacggatggc
 L  G  M  T  R  V  M  E  E  T  I  A  Y  L  K  E  R  T  D  G
gttcatttgtcgcttgacttggatggccttgacccaagcgacgcaccgggagtcggaacg
 V  H  L  S  L  D  L  D  G  L  D  P  S  D  A  P  G  V  G  T
cctgtcattggaggattgacataccgcgaaagccatttggcgatggagatgctggccgag
 P  V  I  G  G  L  T  Y  R  E  S  H  L  A  M  E  M  L  A  E
gcacaaatcatcacttcagcggaatttgtcgaagtgaacccgatcttggatgagcggaac
 A  Q  I  I  T  S  A  E  F  V  E  V  N  P  I  L  D  E  R  N
aaaacagcatcagtggctgtagcgctgatggggtcgttgtttggtgaaaaactcatgtaa
 K  T  A  S  V  A  V  A  L  M  G  S  L  F  G  E  K  L  M  -
```

FIG. 3d

```
atgaagccaatttcaattatcggggttccgatggatttagggcagacacgccgcggcgtt
 M  K  P  I  S  I  I  G  V  P  M  D  L  G  Q  T  R  R  G  V
gatatggggccgagcgcaatgcgttatgcaggcgtcatcgaacgtctggaacgtcttcat
 D  M  G  P  S  A  M  R  Y  A  G  V  I  E  R  L  E  R  L  H
tacgatattgaagatttgggagatattccgattggaaaagcagagcggttgcacgagcaa
 Y  D  I  E  D  L  G  D  I  P  I  G  K  A  E  R  L  H  E  Q
ggagattcacggttgcgcaatttgaaagcggttgcggaagcgaacgagaaacttgcggcg
 G  D  S  R  L  R  N  L  K  A  V  A  E  A  N  E  K  L  A  A
gcggttgaccaagtcgttcagcggggcgatttccgcttgtgttgggcggcgaccatagc
 A  V  D  Q  V  V  Q  R  G  R  F  P  L  V  L  G  G  D  H  S
atcgccattggcacgctcgccggggtggcgaaacattatgagcggcttggagtgatctgg
 I  A  I  G  T  L  A  G  V  A  K  H  Y  E  R  L  G  V  I  W
tatgacgcgcatggcgacgtcaacaccgcggaaacgtcgccgtctggaaacattcatggc
 Y  D  A  H  G  D  V  N  T  A  E  T  S  P  S  G  N  I  H  G
atgccgctggcggcgagcctcgggtttggccatccggcgctgacgcaaatcggcggatac
 M  P  L  A  A  S  L  G  F  H  P  A  L  T  Q  I  G  G  Y
tgccccaaaatcaagccggaacatgtcgtgttgatcggcgtccgttcccttgatgaaggg
 C  P  K  I  K  P  E  H  V  V  L  I  G  V  R  S  L  D  E  G
gagaagaagtttattcgcgaaaaaggaatcaaaatttacacgatgcatgaggttgatcgg
 E  K  K  F  I  R  E  K  G  I  K  I  Y  T  M  H  E  V  D  R
ctcggaatgacaaggggtgatggaagaaacgatcgcctatttaaaagaacgaacggatggc
 L  G  M  T  R  V  M  E  E  T  I  A  Y  L  K  E  R  T  D  G
gttcatttgtcgcttgacttggatggccttgacccaagcgacgcaccggagtcggaacg
 V  H  L  S  L  D  L  D  G  L  D  P  S  D  A  P  G  V  G  T
cctgtcattggaggattgacataccgcgaaagccatttggcgatggagatgctggccgag
 P  V  I  G  G  L  T  Y  R  E  S  H  L  A  M  E  M  L  A  E
gcacaaatcatcacttcagcggaatttgtcgaagtgaacccgatcttggatgagcggaac
 A  Q  I  I  T  S  A  E  F  V  E  V  N  P  I  L  D  E  R  N
aaaacagcatcagtggctgtagcgctgatggggtcgttgtttggtgaaaaactcatg cat
 K  T  A  S  V  A  V  A  L  M  G  S  L  F  G  E  K  L  M  H
caccatcaccatcac taa
 H  H  H  H  H  -
```

↑
6xHis-tag encoding codons

FIG.6a1
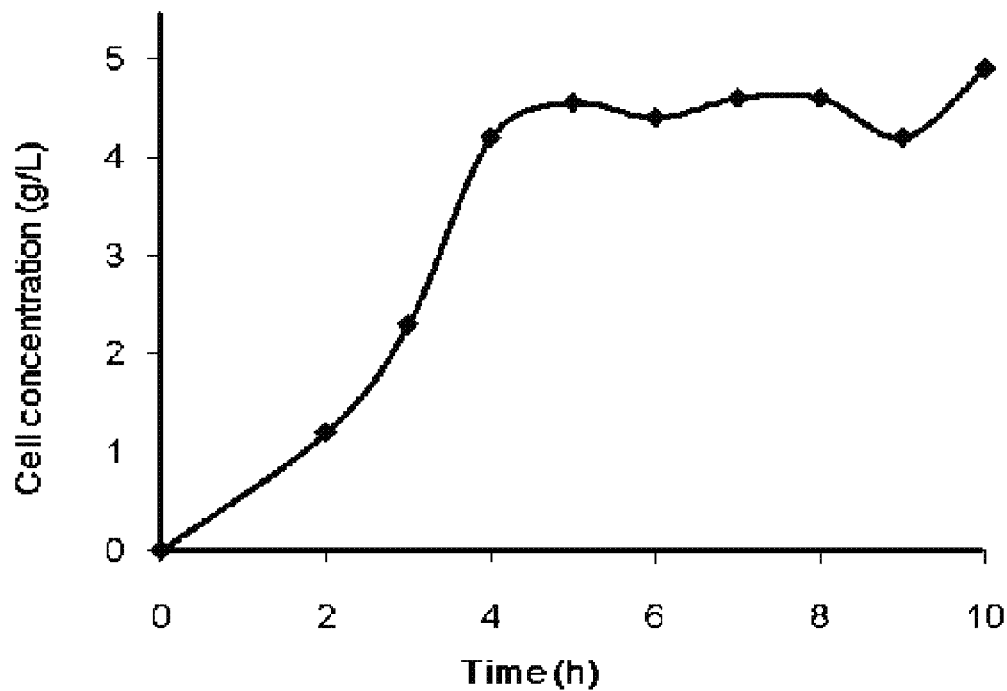
FIG. 6a2
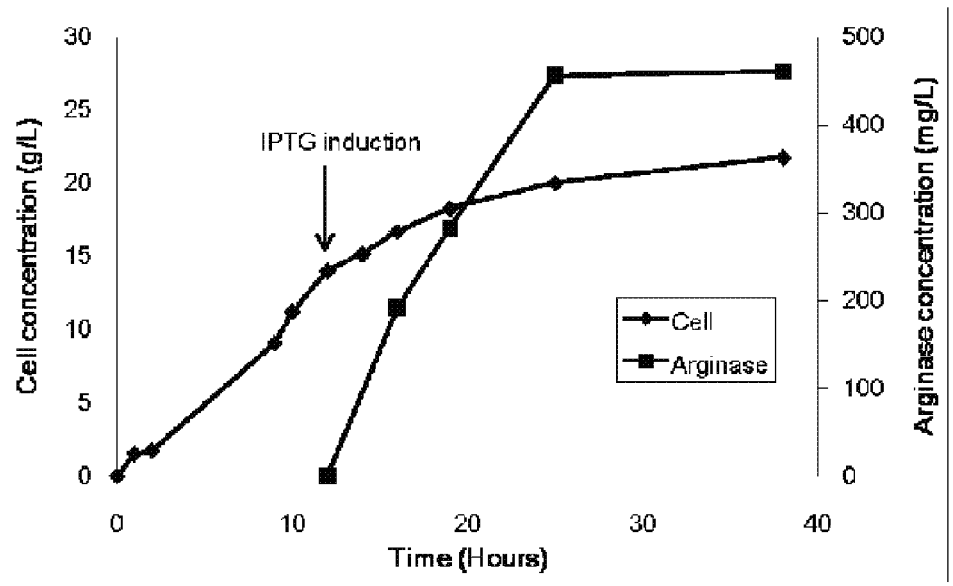

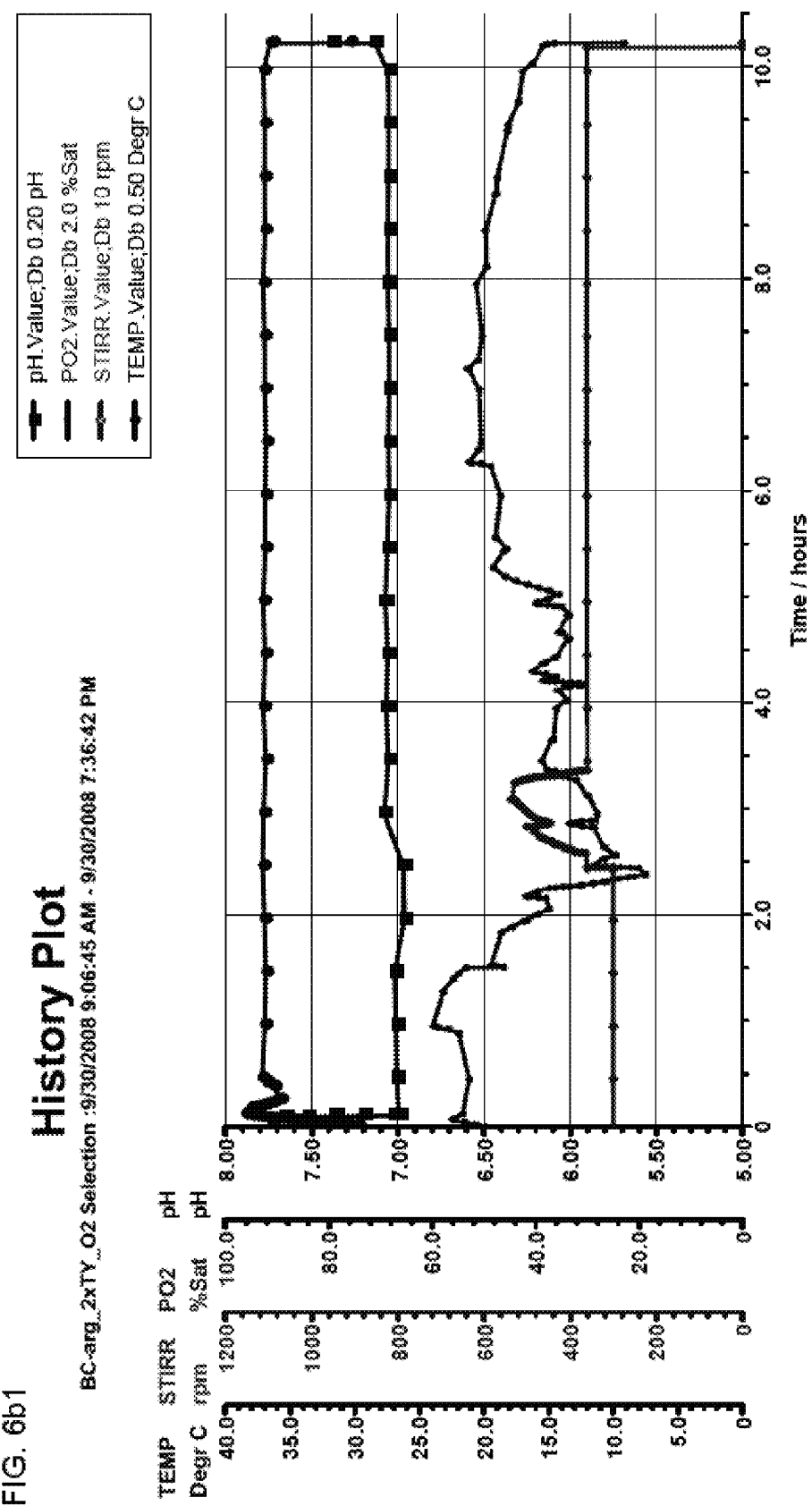
FIG. 6b1

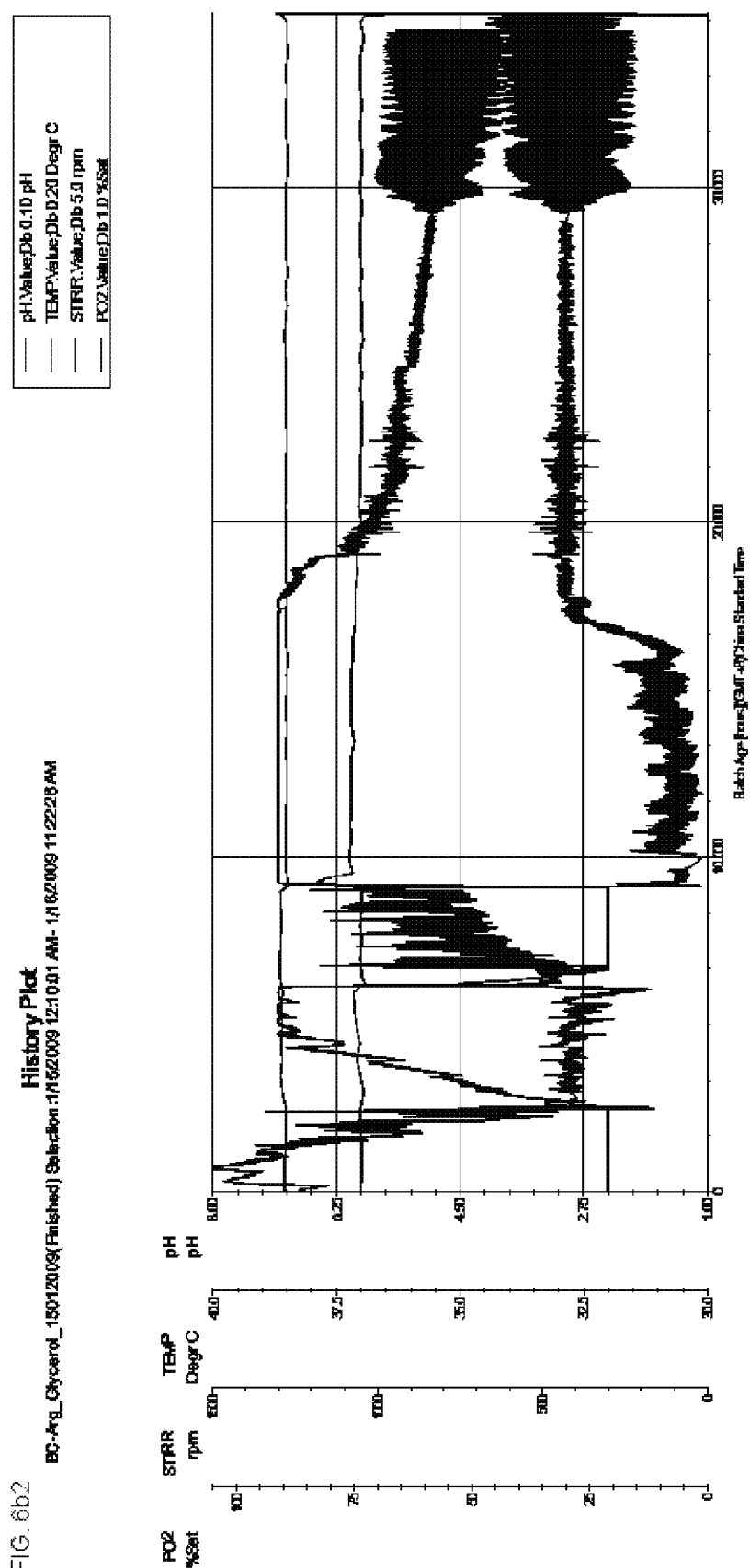
FIG. 6b2

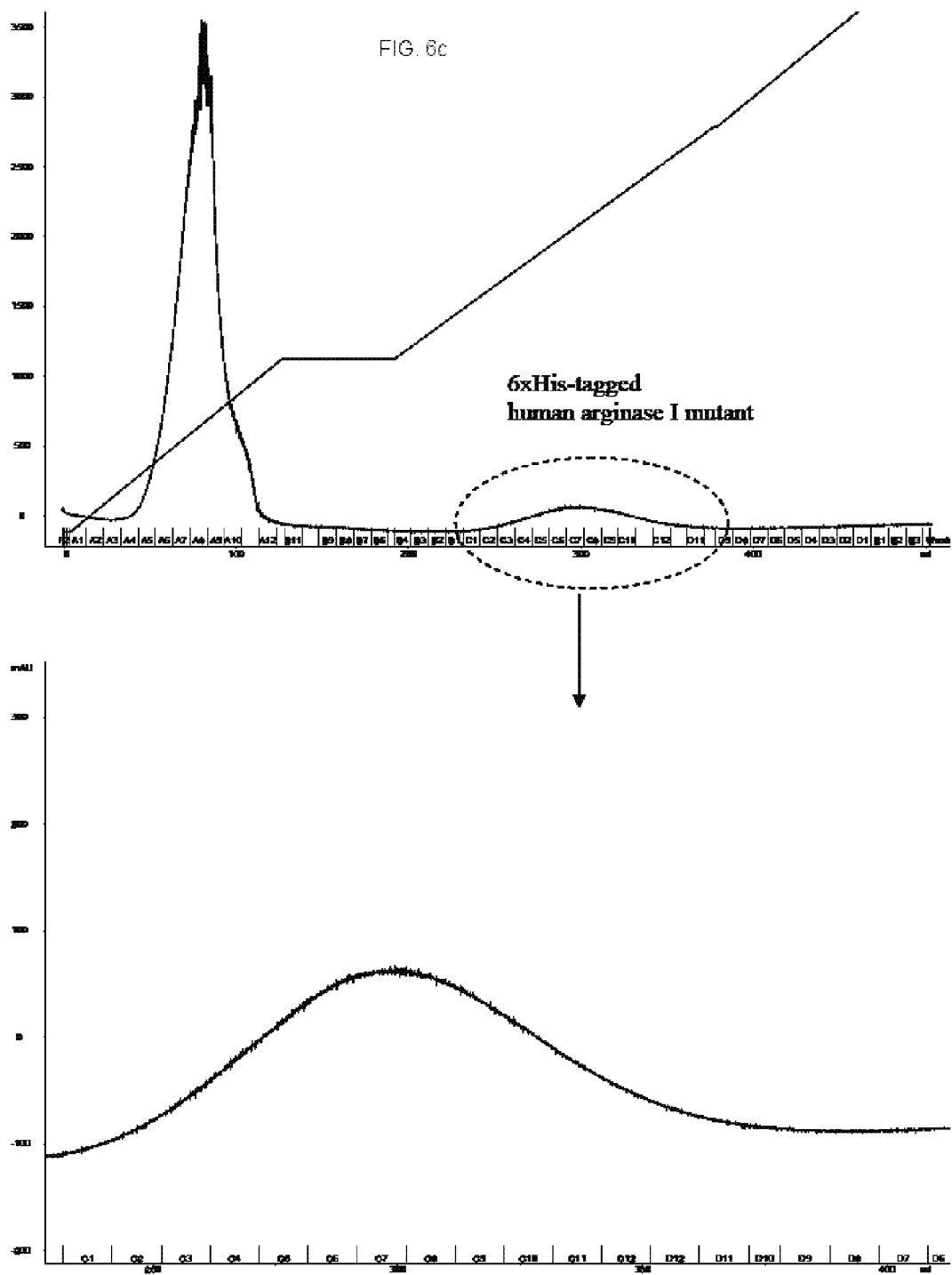

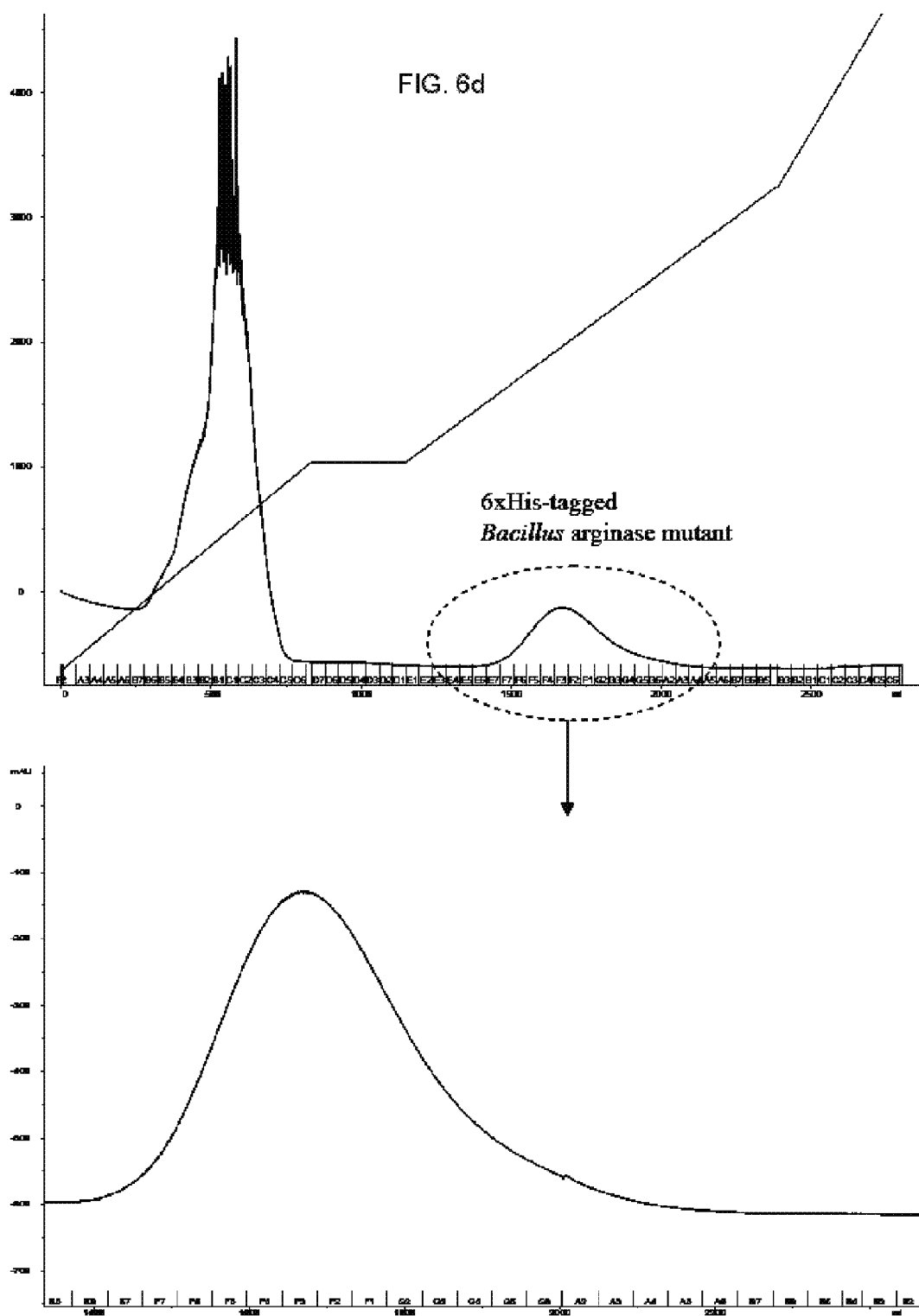

| Lane 1: Low-range protein marker, Bio-Rad |
| Lane 2: Before chelating FF sepharose column (2.5 µL) |
| Lane 3: Flowthrough (2.5 µL) |
| Lane 4: Fraction A8 (10 µL) |
| Lane 5: Fraction C2 (10 µL) |
| Lane 6: Fraction C5 (10 µL) |
| Lane 7: Fraction C8 (10 µL) |
| Lane 8: Fraction C11 (10 µL) |
| Lane 9: Fraction D11 (10 µL) |
| Lane 10: Fraction D7 (10 µL) |

| Lane 1: Low-range marker, Bio-Rad |
| Lane 2: Before chelating FF sepharose column (2.5 µL) |
| Lane 3: Flowthrough (5 µL) |
| Lane 4: Fraction C1 (10 µL) |
| Lane 5: Fraction E7 (10 µL) |
| Lane 6: Fraction F7 (10 µL) |
| Lane 7: Fraction F6 (10 µL) |
| Lane 8: Fraction F3 (10 µL) |
| Lane 9: Fraction G2 (10 µL) |
| Lane 10: Fraction G5 (10 µL) |

| Lane 1: Low-range marker, Bio-Rad |
| Lane 2: Unpegylated human arginase I |
| Lane 3: Cys⁴⁵ pegylated human arginase I |

| Lane 1: Low-range marker, Bio-Rad |
| Lane 2: Unpegylated Bacillus caldovelox arginase |
| Lane 3: Cys¹⁶¹ pegylated Bacillus caldovelox arginase |

Fig. 15 Cytotoxicity of Cys$^{45}$ pegylated human arginase I (HAI-PEG20)

SEQUENCE LISTING

<160> NUMBER OF SEQ ID NOS: 22

<210> SEQ ID NO 1
<211> LENGTH: 969
<212> TYPE: DNA
<213> ORGANISM: Homo sapiens

<400> SEQUENCE: 1

```
atgagcgcca agtccagaac catagggatt attggagctc ctttctcaaa gggacagcca      60
cgaggagggg tggaagaagg ccctacagta ttgagaaagg ctggtctgct tgagaaactt     120
aaagaacaag agtgtgatgt gaaggattat ggggacctgc cctttgctga catccctaat     180
gacagtccct ttcaaattgt gaagaatcca aggtctgtgg gaaaagcaag cgagcagctg     240
gctggcaagg tggcagaagt caagaagaac ggaagaatca gcctggtgct gggcggagac     300
cacagtttgg caattggaag catctctggc catgccaggg tccaccctga tcttggagtc     360
atctgggtgg atgctcacac tgatatcaac actccactga caaccacaag tggaaacttg     420
catggacaac ctgtatcttt cctcctgaag gaactaaaag gaaagattcc cgatgtgcca     480
ggattctcct gggtgactcc ctgtatatct gccaaggata ttgtgtatat tggcttgaga     540
gacgtggacc ctgggggaaca ctacattttg aaaactctag gcattaaata cttttcaatg     600
actgaagtgg acagactagg aattggcaag gtgatggaag aaacactcag ctatctacta     660
ggaagaaaga aaaggccaat tcatctaagt tttgatgttg acggactgga cccatctttc     720
acaccagcta ctggcacacc agtcgtggga ggtctgacat acagagaagg tctctacatc     780
acagaagaaa tctacaaaac agggctactc tcaggattag atataatgga agtgaaccca     840
tccctgggga agacaccaga agaagtaact cgaacagtga acacagcagt tgcaataacc     900
ttggcttgtt tcggacttgc tcgggagggt aatcacaagc ctattgacta ccttaaccca     960
cctaagtaa                                                            969
```

<210> SEQ ID NO 2
<211> LENGTH: 969
<212> TYPE: DNA
<213> ORGANISM: artificial sequence
<220> FEATURE:
<223> OTHER INFORMATION: Human arginase I designed for site-directed pegylation

<400> SEQUENCE: 2

```
atgagcgcca agtccagaac catagggatt attggagctc ctttctcaaa gggacagcca      60
cgaggagggg tggaagaagg ccctacagta ttgagaaagg ctggtctgct tgagaaactt     120
aaagaacaag agtgtgatgt gaaggattat ggggacctgc cctttgctga catccctaat     180
gacagtccct ttcaaattgt gaagaatcca aggtctgtgg gaaaagcaag cgagcagctg     240
```

```
gctggcaagg tggcagaagt caagaagaac ggaagaatca gcctggtgct gggcggagac      300
cacagtttgg caattggaag catctctggc catgccaggg tccaccctga tcttggagtc      360
atctgggtgg atgctcacac tgatatcaac actccactga caaccacaag tggaaacttg      420
catggacaac ctgtatcttt cctcctgaag gaactaaaag gaaagattcc cgatgtgcca      480
ggattctcct gggtgactcc ctctatatct gccaaggata ttgtgtatat tggcttgaga      540
gacgtggacc ctggggaaca ctacattttg aaaactctag cattaaaata cttttcaatg      600
actgaagtgg acagactagg aattggcaag gtgatggaag aaacactcag ctatctacta      660
ggaagaaaga aaaggccaat tcatctaagt tttgatgttg acggactgga cccatctttc      720
acaccagcta ctggcacacc agtcgtggga ggtctgacat acagaaagg tctctacatc       780 acagaagaaa tctacaaaac agggctactc tcaggattag atataatgga agtgaaccca      840
tccctgggga agacaccaga agaagtaact cgaacagtga acacagcagt tgcaataacc      900
ttggcttctt tcggacttgc tcgggagggt aatcacaagc ctattgacta ccttaaccca      960
cctaagtaa                                                              969
```

<210> SEQ ID NO 3
<211> LENGTH: 900
<212> TYPE: DNA
<213> ORGANISM: Bacillus caldovelox

<400> SEQUENCE: 3

```
atgaagccaa tttcaattat cggggttccg atggatttag gcagacacg ccgcggcgtt       60 gatatggggc cgagcgcaat gcgttatgca ggcgtcatcg aacgtctgga acgtcttcat      120
tacgatattg aagatttggg agatattccg attggaaaag cagagcggtt gcacgagcaa      180
ggagattcac ggttgcgcaa tttgaaagcg gttgcggaag cgaacgagaa acttgcggcg      240
gcggttgacc aagtcgttca gcgggggcga tttccgcttg tgttgggcgg cgaccatagc      300
atcgccattg gcacgctcgc cggggtggcg aaacattatg agcggcttgg agtgatctgg      360
tatgacgcgc atgcgacgt caacaccgcg gaaacgtcgc cgtctggaaa cattcatggc      420
atgccgctgg cggcgagcct cgggtttggc catccggcgc tgacgcaaat cggcggatac      480
agccccaaaa tcaagccgga acatgtcgtg ttgatcggcg tccgttccct tgatgaaggg      540
gagaagaagt ttattcgcga aaaggaatc aaaatttaca cgatgcatga ggttgatcgg      600
ctcggaatga caagggtgat ggaagaaacg atcgcctatt taaaagaacg aacgatggc      660 gttcatttgt cgcttgactt ggatggcctt gacccaagcg acgcaccggg agtcggaacg      720
cctgtcattg gaggattgac ataccgcgaa agccatttgg cgatggagat gctggccgag      780
gcacaaatca tcacttcagc ggaatttgtc gaagtgaacc cgatcttgga tgagcggaac      840
aaaacagcat cagtggctgt agcgctgatg gggtcgttgt ttggtgaaaa actcatgtaa      900
```

<210> SEQ ID NO 4
<211> LENGTH: 918
<212> TYPE: DNA
<213> ORGANISM: artificial sequence
<220> FEATURE:
<223> OTHER INFORMATION: Bacillus caldovelox arginase designed for site-
      directed pegylation

<400> SEQUENCE: 4

```
atgaagccaa tttcaattat cggggttccg atggatttag gcagacacg ccgcggcgtt       60 gatatggggc cgagcgcaat gcgttatgca ggcgtcatcg aacgtctgga acgtcttcat      120
```

```
tacgatattg aagatttggg agatattccg attggaaaag cagagcggtt gcacgagcaa    180
ggagattcac ggttgcgcaa tttgaaagcg gttgcggaag cgaacgagaa acttgcggcg    240
gcggttgacc aagtcgttca gcggggggcga tttccgcttg tgttgggcgg cgaccatagc   300
atcgccattg gcacgctcgc cggggtggcg aaacattatg agcggcttgg agtgatctgg    360
tatgacgcgc atggcgacgt caacaccgcg gaaacgtcgc cgtctggaaa cattcatggc    420
atgccgctgg cggcgagcct cgggtttggc catccgcgc tgacgcaaat cggcggatac     480
tgccccaaaa tcaagccgga acatgtcgtg ttgatcggcg tccgttccct tgatgaaggg    540
gagaagaagt ttattcgcga aaaggaatc aaaatttaca cgatgcatga ggttgatcgg     600
ctcggaatga caagggtgat ggaagaaacg atcgcctatt aaaagaacg aacggatggc     660
gttcatttgt cgcttgactt ggatggcctt gacccaagcg acgcaccggg agtcggaacg    720
cctgtcattg aggattgac ataccgcgaa agccatttgg cgatggagat gctggccgag     780
gcacaaatca tcacttcagc ggaatttgtc gaagtgaacc cgatcttgga tgagcggaac    840
aaaacagcat cagtggctgt agcgctgatg gggtcgttgt ttggtgaaaa actcatgcat    900
caccatcacc atcactaa                                                 918

<210> SEQ ID NO 5
<211> LENGTH: 322
<212> TYPE: PRT
<213> ORGANISM: Homo sapiens

<400> SEQUENCE: 5

Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Cys Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240
```

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
            275                 280                 285

Val Thr Arg Thr Val Asn Thr Ala Val Ala Ile Thr Leu Ala Cys Phe
        290                 295                 300

Gly Leu Ala Arg Glu Gly Asn His Lys Pro Ile Asp Tyr Leu Asn Pro
305                 310                 315                 320

Pro Lys

<210> SEQ ID NO 6
<211> LENGTH: 322
<212> TYPE: PRT
<213> ORGANISM: artificial sequence
<220> FEATURE:
<223> OTHER INFORMATION: amino acid sequence of human arginase I with
      Cys168 and Cys303 replaced by Ser

<400> SEQUENCE: 6

Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Cys Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Ser Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

```
Leu Asp Ile Met Glu Val Asn Pro Ser Leu Gly Lys Thr Pro Glu
        275                 280                 285

Val Thr Arg Thr Val Asn Thr Ala Val Ala Ile Thr Leu Ala Ser Phe
    290                 295                 300

Gly Leu Ala Arg Glu Gly Asn His Lys Pro Ile Asp Tyr Leu Asn Pro
305                 310                 315                 320

Pro Lys

<210> SEQ ID NO 7
<211> LENGTH: 299
<212> TYPE: PRT
<213> ORGANISM: Bacillus caldovelox

<400> SEQUENCE: 7

Met Lys Pro Ile Ser Ile Ile Gly Val Pro Met Asp Leu Gly Gln Thr
1               5                   10                  15

Arg Arg Gly Val Asp Met Gly Pro Ser Ala Met Arg Tyr Ala Gly Val
                20                  25                  30

Ile Glu Arg Leu Glu Arg Leu His Tyr Asp Ile Glu Asp Leu Gly Asp
            35                  40                  45

Ile Pro Ile Gly Lys Ala Glu Arg Leu His Glu Gln Gly Asp Ser Arg
        50                  55                  60

Leu Arg Asn Leu Lys Ala Val Ala Glu Ala Asn Glu Lys Leu Ala Ala
65                  70                  75                  80

Ala Val Asp Gln Val Val Gln Arg Gly Arg Phe Pro Leu Val Leu Gly
                85                  90                  95

Gly Asp His Ser Ile Ala Ile Gly Thr Leu Ala Gly Val Ala Lys His
                100                 105                 110

Tyr Glu Arg Leu Gly Val Ile Trp Tyr Asp Ala His Gly Asp Val Asn
            115                 120                 125

Thr Ala Glu Thr Ser Pro Ser Gly Asn Ile His Gly Met Pro Leu Ala
130                 135                 140

Ala Ser Leu Gly Phe Gly His Pro Ala Leu Thr Gln Ile Gly Gly Tyr
145                 150                 155                 160

Ser Pro Lys Ile Lys Pro Glu His Val Val Leu Ile Gly Val Arg Ser
                165                 170                 175

Leu Asp Glu Gly Glu Lys Lys Phe Ile Arg Glu Lys Gly Ile Lys Ile
            180                 185                 190

Tyr Thr Met His Glu Val Asp Arg Leu Gly Met Thr Arg Val Met Glu
        195                 200                 205

Glu Thr Ile Ala Tyr Leu Lys Glu Arg Thr Asp Gly Val His Leu Ser
210                 215                 220

Leu Asp Leu Asp Gly Leu Asp Pro Ser Asp Ala Pro Gly Val Gly Thr
225                 230                 235                 240

Pro Val Ile Gly Gly Leu Thr Tyr Arg Glu Ser His Leu Ala Met Glu
                245                 250                 255

Met Leu Ala Glu Ala Gln Ile Ile Thr Ser Ala Glu Phe Val Glu Val
            260                 265                 270

Asn Pro Ile Leu Asp Glu Arg Asn Lys Thr Ala Ser Val Ala Val Ala
        275                 280                 285

Leu Met Gly Ser Leu Phe Gly Glu Lys Leu Met
    290                 295

<210> SEQ ID NO 8
<211> LENGTH: 305
<212> TYPE: PRT
```

<210> ORGANISM: artificial sequence
<220> FEATURE:
<223> OTHER INFORMATION: amino acid sequence of 6xHis-tagged Bacillus
      caldovelox arginase with Ser161 replaced by Cys.

<400> SEQUENCE: 8

```
Met Lys Pro Ile Ser Ile Ile Gly Val Pro Met Asp Leu Gly Gln Thr
1               5                   10                  15

Arg Arg Gly Val Asp Met Gly Pro Ser Ala Met Arg Tyr Ala Gly Val
            20                  25                  30

Ile Glu Arg Leu Glu Arg Leu His Tyr Asp Ile Glu Asp Leu Gly Asp
        35                  40                  45

Ile Pro Ile Gly Lys Ala Glu Arg Leu His Glu Gln Gly Asp Ser Arg
    50                  55                  60

Leu Arg Asn Leu Lys Ala Val Ala Glu Ala Asn Glu Lys Leu Ala Ala
65                  70                  75                  80

Ala Val Asp Gln Val Val Gln Arg Gly Arg Phe Pro Leu Val Leu Gly
                85                  90                  95

Gly Asp His Ser Ile Ala Ile Gly Thr Leu Ala Gly Val Ala Lys His
            100                 105                 110

Tyr Glu Arg Leu Gly Val Ile Trp Tyr Asp Ala His Gly Asp Val Asn
        115                 120                 125

Thr Ala Glu Thr Ser Pro Ser Gly Asn Ile His Gly Met Pro Leu Ala
    130                 135                 140

Ala Ser Leu Gly Phe Gly His Pro Ala Leu Thr Gln Ile Gly Gly Tyr
145                 150                 155                 160

Cys Pro Lys Ile Lys Pro Glu His Val Val Leu Ile Gly Val Arg Ser
                165                 170                 175

Leu Asp Glu Gly Glu Lys Lys Phe Ile Arg Glu Lys Gly Ile Lys Ile
            180                 185                 190

Tyr Thr Met His Glu Val Asp Arg Leu Gly Met Thr Arg Val Met Glu
        195                 200                 205

Glu Thr Ile Ala Tyr Leu Lys Glu Arg Thr Asp Gly Val His Leu Ser
    210                 215                 220

Leu Asp Leu Asp Gly Leu Asp Pro Ser Asp Ala Pro Gly Val Gly Thr
225                 230                 235                 240

Pro Val Ile Gly Gly Leu Thr Tyr Arg Glu Ser His Leu Ala Met Glu
                245                 250                 255

Met Leu Ala Glu Ala Gln Ile Ile Thr Ser Ala Glu Phe Val Glu Val
            260                 265                 270

Asn Pro Ile Leu Asp Glu Arg Asn Lys Thr Ala Ser Val Ala Val Ala
        275                 280                 285

Leu Met Gly Ser Leu Phe Gly Glu Lys Leu Met His His His His His
    290                 295                 300

His
305
```

<210> SEQ ID NO 9
<211> LENGTH: 969
<212> TYPE: DNA
<213> ORGANISM: artificial sequence
<220> FEATURE:
<223> OTHER INFORMATION: human arginase I mutant (C168S/C303S)

<400> SEQUENCE: 9
atgagcgcca agtccagaac catagggatt attggagctc ctttctcaaa gggacagcca      60
cgaggagggg tggaagaagg ccctacagta ttgagaaagg ctggtctgct tgagaaactt     120

-continued

```
aaagaacaag agtgtgatgt gaaggattat ggggacctgc cctttgctga catccctaat      180
gacagtccct ttcaaattgt gaagaatcca aggtctgtgg gaaaagcaag cgagcagctg      240
gctggcaagg tggcagaagt caagaagaac ggaagaatca gcctggtgct gggcggagac      300
cacagtttgg caattggaag catctctggc catgccaggg tccaccctga tcttggagtc      360
atctgggtgg atgctcacac tgatatcaac actccactga caaccacaag tggaaacttg      420
catggacaac ctgtatcttt cctcctgaag gaactaaaag gaaagattcc cgatgtgcca      480
ggattctcct gggtgactcc ctctatatct gccaaggata ttgtgtatat tggcttgaga      540
gacgtggacc ctggggaaca ctacattttg aaaactctag cattaaata cttttcaatg      600 actgaagtgg acagactagg aattggcaag gtgatggaag aaacactcag ctatctacta      660
ggaagaaaga aaaggccaat tcatctaagt tttgatgttg acggactgga cccatctttc      720
acaccagcta ctggcacacc agtcgtggga ggtctgacat acagagaagg tctctacatc      780
acagaagaaa tctacaaaac agggctactc tcaggattga atataatgga agtgaaccca      840
tccctgggga agacaccaga agaagtaact cgaacagtga acacagcagt tgcaataacc      900
ttggcttctt tcggacttgc tcgggagggt aatcacaagc ctattgacta ccttaaccca      960
cctaagtaa                                                              969
```

<210> SEQ ID NO 10
<211> LENGTH: 322
<212> TYPE: PRT
<213> ORGANISM: artificial sequence
<220> FEATURE:
<223> OTHER INFORMATION: human arginase I mutant (C168S/C303S)

<400> SEQUENCE: 10

```
Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Cys Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Ser Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205
```

```
Gly Lys Val Met Glu Glu Thr Leu Ser Tyr Leu Leu Gly Arg Lys Lys
             210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
        275                 280                 285

Val Thr Arg Thr Val Asn Thr Ala Val Ala Ile Thr Leu Ala Ser Phe
    290                 295                 300

Gly Leu Ala Arg Glu Gly Asn His Lys Pro Ile Asp Tyr Leu Asn Pro
305                 310                 315                 320

Pro Lys
```

```
<210> SEQ ID NO 11
<211> LENGTH: 990
<212> TYPE: DNA
<213> ORGANISM: artificial sequence
<220> FEATURE:
<223> OTHER INFORMATION: 6xHis-tagged human arginase I mutant
      (C168S/C303S)

<400> SEQUENCE: 11
atgcatcacc atcaccatca catgagcgcc aagtccagaa ccatagggat tattggagct      60
cctttctcaa agggacagcc acgaggaggg gtggaagaag ccctacagt attgagaaag      120
gctggtctgc ttgagaaact taaagaacaa gagtgtgatg tgaaggatta tgggacctg      180
cccttgctg acatccctaa tgacagtccc tttcaaattg tgaagaatcc aaggtctgtg      240
ggaaaagcaa gcgagcagct ggctggcaag gtggcagaag tcaagaagaa cggaagaatc      300
agcctggtgc tgggcggaga ccacagtttg gcaattggaa gcatctctgg ccatgccagg      360
gtccacccctg atcttggagt catctgggtg gatgctcaca ctgatatcaa cactccactg      420
acaaccacaa gtggaaactt gcatggacaa cctgtatctt cctcctgaa ggaactaaaa      480
ggaaagattc ccgatgtgcc aggattctcc tgggtgactc cctctatatc tgccaaggat      540
attgtgtata ttggcttgag agacgtggac cctggggaac actacatttt gaaaactcta      600
ggcattaaat acttttcaat gactgaagtg gacagactag gaattggcaa ggtgatggaa      660
gaaacactca gctatctact aggaagaaag aaaaggccaa ttcatctaag ttttgatgtt      720
gacggactgg acccatcttt cacaccagct actggcacac cagtcgtggg aggtctgaca      780
tacagagaag gtctctacat cacagaagaa atctacaaaa cagggctact ctcaggatta      840
gatataatgg aagtgaaccc atccctgggg aagacaccag aagaagtaac tcgaacagtg      900
aacacagcag ttgcaataac cttggcttct ttcggacttg ctcgggaggg taatcacaag      960
cctattgact accttaaccc acctaagtaa                                      990
```

```
<210> SEQ ID NO 12
<211> LENGTH: 329
<212> TYPE: PRT
<213> ORGANISM: artificial sequence
<220> FEATURE:
<223> OTHER INFORMATION: 6xHis-tagged human arginase I mutant
      (C168S/C303S)

<400> SEQUENCE: 12

Met His His His His His His Met Ser Ala Lys Ser Arg Thr Ile Gly
```

```
            1               5                   10                  15
Ile Ile Gly Ala Pro Phe Ser Lys Gly Gln Pro Arg Gly Gly Val Glu
                    20                  25                  30

Glu Gly Pro Thr Val Leu Arg Lys Ala Gly Leu Leu Glu Lys Leu Lys
                35                  40                  45

Glu Gln Glu Cys Asp Val Lys Asp Tyr Gly Asp Leu Pro Phe Ala Asp
            50                  55                  60

Ile Pro Asn Asp Ser Pro Phe Gln Ile Val Lys Asn Pro Arg Ser Val
65                  70                  75                  80

Gly Lys Ala Ser Glu Gln Leu Ala Gly Lys Val Ala Glu Val Lys Lys
                85                  90                  95

Asn Gly Arg Ile Ser Leu Val Leu Gly Asp His Ser Leu Ala Ile
                    100                 105                 110

Gly Ser Ile Ser Gly His Ala Arg Val His Pro Asp Leu Gly Val Ile
            115                 120                 125

Trp Val Asp Ala His Thr Asp Ile Asn Thr Pro Leu Thr Thr Thr Ser
        130                 135                 140

Gly Asn Leu His Gly Gln Pro Val Ser Phe Leu Leu Lys Glu Leu Lys
145                 150                 155                 160

Gly Lys Ile Pro Asp Val Pro Gly Phe Ser Trp Val Thr Pro Ser Ile
                165                 170                 175

Ser Ala Lys Asp Ile Val Tyr Ile Gly Leu Arg Asp Val Asp Pro Gly
            180                 185                 190

Glu His Tyr Ile Leu Lys Thr Leu Gly Ile Lys Tyr Phe Ser Met Thr
        195                 200                 205

Glu Val Asp Arg Leu Gly Ile Gly Lys Val Met Glu Glu Thr Leu Ser
    210                 215                 220

Tyr Leu Leu Gly Arg Lys Lys Arg Pro Ile His Leu Ser Phe Asp Val
225                 230                 235                 240

Asp Gly Leu Asp Pro Ser Phe Thr Pro Ala Thr Gly Thr Pro Val Val
                245                 250                 255

Gly Gly Leu Thr Tyr Arg Glu Gly Leu Tyr Ile Thr Glu Glu Ile Tyr
            260                 265                 270

Lys Thr Gly Leu Leu Ser Gly Leu Asp Ile Met Glu Val Asn Pro Ser
        275                 280                 285

Leu Gly Lys Thr Pro Glu Glu Val Thr Arg Thr Val Asn Thr Ala Val
    290                 295                 300

Ala Ile Thr Leu Ala Ser Phe Gly Leu Ala Arg Glu Gly Asn His Lys
305                 310                 315                 320

Pro Ile Asp Tyr Leu Asn Pro Pro Lys
                325

<210> SEQ ID NO 13
<211> LENGTH: 900
<212> TYPE: DNA
<213> ORGANISM: artificial sequence
<220> FEATURE:
<223> OTHER INFORMATION: Bacillus caldovelox arginase mutant (S161C)

<400> SEQUENCE: 13
atgaagccaa tttcaattat cggggttccg atggatttag gcagacacg  ccgcggcgtt    60 gatatgggc cgagcgcaat gcgttatgca ggcgtcatcg aacgtctgga acgtcttcat   120
tacgatattg aagatttggg agatattccg attggaaaag cagagcggtt gcacgagcaa   180
ggagattcac ggttgcgcaa tttgaaagcg gttgcggaag cgaacgagaa acttgcggcg   240
```

```
gcggttgacc aagtcgttca gcgggggcga tttccgcttg tgttgggcgg cgaccatagc    300
atcgccattg gcacgctcgc cggggtggcg aaacattatg agcggcttgg agtgatctgg    360
tatgacgcgc atggcgacgt caacaccgcg gaaacgtcgc cgtctggaaa cattcatggc    420
atgccgctgg cggcgagcct cgggtttggc catccggcgc tgacgcaaat cggcggatac    480
tgccccaaaa tcaagccgga acatgtcgtg ttgatcggcg tccgttccct tgatgaaggg    540
gagaagaagt ttattcgcga aaaggaatc aaaatttaca cgatgcatga ggttgatcgg    600
ctcggaatga caagggtgat ggaagaaacg atcgcctatt taaaagaacg aacggatggc    660
gttcatttgt cgcttgactt ggatggcctt gacccaagcg acgcaccggg agtcggaacg    720
cctgtcattg gaggattgac ataccgcgaa agccatttgg cgatggagat gctggccgag    780
gcacaaatca tcacttcagc ggaatttgtc gaagtgaacc cgatcttgga tgagcggaac    840
aaaacagcat cagtggctgt agcgctgatg gggtcgttgt ttggtgaaaa actcatgtaa    900
```

<210> SEQ ID NO 14
<211> LENGTH: 299
<212> TYPE: PRT
<213> ORGANISM: artificial sequence
<220> FEATURE:
<223> OTHER INFORMATION: Bacillus caldovelox arginase mutant (S161C)

<400> SEQUENCE: 14

```
Met Lys Pro Ile Ser Ile Ile Gly Val Pro Met Asp Leu Gly Gln Thr
1               5                   10                  15

Arg Arg Gly Val Asp Met Gly Pro Ser Ala Met Arg Tyr Ala Gly Val
            20                  25                  30

Ile Glu Arg Leu Glu Arg Leu His Tyr Asp Ile Glu Asp Leu Gly Asp
        35                  40                  45

Ile Pro Ile Gly Lys Ala Glu Arg Leu His Glu Gln Gly Asp Ser Arg
    50                  55                  60

Leu Arg Asn Leu Lys Ala Val Ala Glu Ala Asn Glu Lys Leu Ala Ala
65                  70                  75                  80

Ala Val Asp Gln Val Val Gln Arg Gly Arg Phe Pro Leu Val Leu Gly
                85                  90                  95

Gly Asp His Ser Ile Ala Ile Gly Thr Leu Ala Gly Val Ala Lys His
            100                 105                 110

Tyr Glu Arg Leu Gly Val Ile Trp Tyr Asp Ala His Gly Asp Val Asn
        115                 120                 125

Thr Ala Glu Thr Ser Pro Ser Gly Asn Ile His Gly Met Pro Leu Ala
    130                 135                 140

Ala Ser Leu Gly Phe Gly His Pro Ala Leu Thr Gln Ile Gly Gly Tyr
145                 150                 155                 160

Cys Pro Lys Ile Lys Pro Glu His Val Val Leu Ile Gly Val Arg Ser
                165                 170                 175

Leu Asp Glu Gly Glu Lys Lys Phe Ile Arg Glu Lys Gly Ile Lys Ile
            180                 185                 190

Tyr Thr Met His Glu Val Asp Arg Leu Gly Met Thr Arg Val Met Glu
        195                 200                 205

Glu Thr Ile Ala Tyr Leu Lys Glu Arg Thr Asp Gly Val His Leu Ser
    210                 215                 220

Leu Asp Leu Asp Gly Leu Asp Pro Ser Asp Ala Pro Gly Val Gly Thr
225                 230                 235                 240

Pro Val Ile Gly Gly Leu Thr Tyr Arg Glu Ser His Leu Ala Met Glu
                245                 250                 255
```

```
Met Leu Ala Glu Ala Gln Ile Ile Thr Ser Ala Glu Phe Val Glu Val
            260                 265                 270

Asn Pro Ile Leu Asp Glu Arg Asn Lys Thr Ala Ser Val Ala Val Ala
        275                 280                 285

Leu Met Gly Ser Leu Phe Gly Glu Lys Leu Met
    290                 295
```

<210> SEQ ID NO 15
<211> LENGTH: 918
<212> TYPE: DNA
<213> ORGANISM: artificial sequence
<220> FEATURE:
<223> OTHER INFORMATION: 6xHis-tagged Bacillus caldovelox arginase
       mutant (S161C)

<400> SEQUENCE: 15

```
atgaagccaa tttcaattat cggggttccg atggatttag ggcagacacg ccgcggcgtt    60
gatatgggc cgagcgcaat gcgttatgca ggcgtcatcg aacgtctgga acgtcttcat    120
tacgatattg aagatttggg agatattccg attggaaaag cagagcggtt gcacgagcaa    180
ggagattcac ggttgcgcaa tttgaaagcg gttgcggaag cgaacgagaa acttgcggcg    240
gcggttgacc aagtcgttca gcgggggcga tttccgcttg tgttgggcgg cgaccatagc    300
atcgccattg gcacgctcgc cggggtggcg aaacattatg agcggcttgg agtgatctgg    360
tatgacgcgc atggcgacgt caacaccgcg gaaacgtcgc cgtctggaaa cattcatggc    420
atgccgctgg cggcgagcct cgggtttggc catccggcgc tgacgcaaat cggcggatac    480
tgccccaaaa tcaagccgga acatgtcgtg ttgatcggcg tccgttccct tgatgaaggg    540
gagaagaagt ttattcgcga aaaggaatc aaaatttaca cgatgcatga ggttgatcgg    600
ctcggaatga caagggtgat ggaagaaacg atcgcctatt aaaagaacg aacgatggc    660
gttcatttgt cgcttgactt ggatggcctt gacccaagcg acgcaccggg agtcggaacg    720
cctgtcattg gaggattgac ataccgcgaa agccatttgg cgatggagat gctggccgag    780
gcacaaatca tcacttcagc ggaatttgtc gaagtgaacc cgatcttgga tgagcggaac    840
aaaacagcat cagtggctgt agcgctgatg gggtcgttgt ttggtgaaaa actcatgcat    900
caccatcacc atcactaa                                                 918
```

<210> SEQ ID NO 16
<211> LENGTH: 305
<212> TYPE: PRT
<213> ORGANISM: artificial sequence
<220> FEATURE:
<223> OTHER INFORMATION: 6xHis-tagged Bacillus caldovelox arginase
       mutant (S161C)

<400> SEQUENCE: 16

```
Met Lys Pro Ile Ser Ile Ile Gly Val Pro Met Asp Leu Gly Gln Thr
1               5                   10                  15

Arg Arg Gly Val Asp Met Gly Pro Ser Ala Met Arg Tyr Ala Gly Val
            20                  25                  30

Ile Glu Arg Leu Glu Arg Leu His Tyr Asp Ile Glu Asp Leu Gly Asp
        35                  40                  45

Ile Pro Ile Gly Lys Ala Glu Arg Leu His Glu Gln Gly Asp Ser Arg
    50                  55                  60

Leu Arg Asn Leu Lys Ala Val Ala Glu Ala Asn Glu Lys Leu Ala Ala
65                  70                  75                  80

Ala Val Asp Gln Val Val Gln Arg Gly Arg Phe Pro Leu Val Leu Gly
                85                  90                  95
```

Gly Asp His Ser Ile Ala Ile Gly Thr Leu Ala Gly Val Ala Lys His
            100                 105                 110

Tyr Glu Arg Leu Gly Val Ile Trp Tyr Asp Ala His Gly Asp Val Asn
        115                 120                 125

Thr Ala Glu Thr Ser Pro Ser Gly Asn Ile His Gly Met Pro Leu Ala
    130                 135                 140

Ala Ser Leu Gly Phe Gly His Pro Ala Leu Thr Gln Ile Gly Gly Tyr
145                 150                 155                 160

Cys Pro Lys Ile Lys Pro Glu His Val Val Leu Ile Gly Val Arg Ser
                165                 170                 175

Leu Asp Glu Gly Glu Lys Lys Phe Ile Arg Glu Lys Gly Ile Lys Ile
            180                 185                 190

Tyr Thr Met His Glu Val Asp Arg Leu Gly Met Thr Arg Val Met Glu
        195                 200                 205

Glu Thr Ile Ala Tyr Leu Lys Glu Arg Thr Asp Gly Val His Leu Ser
210                 215                 220

Leu Asp Leu Asp Gly Leu Asp Pro Ser Asp Ala Pro Gly Val Gly Thr
225                 230                 235                 240

Pro Val Ile Gly Gly Leu Thr Tyr Arg Glu Ser His Leu Ala Met Glu
                245                 250                 255

Met Leu Ala Glu Ala Gln Ile Ile Thr Ser Ala Glu Phe Val Glu Val
            260                 265                 270

Asn Pro Ile Leu Asp Glu Arg Asn Lys Thr Ala Ser Val Ala Val Ala
        275                 280                 285

Leu Met Gly Ser Leu Phe Gly Glu Lys Leu Met His His His His
    290                 295                 300

His
305

<210> SEQ ID NO 17
<211> LENGTH: 24
<212> TYPE: DNA
<213> ORGANISM: artificial sequence
<220> FEATURE:
<223> OTHER INFORMATION: Primer

<400> SEQUENCE: 17
gatatacata tgcatcacca tcac                                          24

<210> SEQ ID NO 18
<211> LENGTH: 36
<212> TYPE: DNA
<213> ORGANISM: artificial sequence
<220> FEATURE:
<223> OTHER INFORMATION: Primer

<400> SEQUENCE: 18
agtgcaggat ccttacttag gtgggttaag gtagtc                             36

<210> SEQ ID NO 19
<211> LENGTH: 27
<212> TYPE: DNA
<213> ORGANISM: artificial sequence
<220> FEATURE:
<223> OTHER INFORMATION: Primer

<400> SEQUENCE: 19
gggtgactcc ctctatatct gccaagg                                       27

```
<210> SEQ ID NO 20
<211> LENGTH: 27
<212> TYPE: DNA
<213> ORGANISM: artificial sequence
<220> FEATURE:
<223> OTHER INFORMATION: Primer

<400> SEQUENCE: 20
ccttggcaga tatagaggga gtcaccc                                             27

<210> SEQ ID NO 21
<211> LENGTH: 29
<212> TYPE: DNA
<213> ORGANISM: artificial sequence
<220> FEATURE:
<223> OTHER INFORMATION: Primer

<400> SEQUENCE: 21
gcaataacct tggcttcttt cggacttgc                                           29

<210> SEQ ID NO 22
<211> LENGTH: 29
<212> TYPE: DNA
<213> ORGANISM: artificial sequence
<220> FEATURE:
<223> OTHER INFORMATION: Primer

<400> SEQUENCE: 22
gcaagtccga agaagccaa ggttattgc                                            29
```

SITE-DIRECTED PEGYLATION OF ARGINASES AND THE USE THEREOF AS ANTI-CANCER AND ANTI-VIRAL AGENTS

CROSS REFERENCE

This application claims benefit from U.S. Provisional Patent Application No. 61/163,863, filed Mar. 26, 2009, the content of which is incorporated herewith in its entirety by reference.

FIELD OF THE INVENTION

The present invention relates to the modification of an arginase for the purpose of increasing the enzyme's serum or circulating half-life and improving its pharmacokinetic properties, in vivo biological activity, stability, and reducing the immune reaction (immunogenicity) to the enzyme in vivo. More specifically, the invention relates to the site-specific covalent conjugation of monopolyethylene glycol to the arginase through genetically modifying the gene encoding the enzyme to produce mono- and site-specific, pegylated arginase, which become effective means of a number of arginine-dependent diseases, such as, for example, various cancers and human immunodeficiency virus (HIV) infection.

BACKGROUND OF THE INVENTION

Arginase

Arginase is a manganese metalloenzyme containing a metal-activated hydroxide ion, a critical nucleophile in metalloenzymes that catalyze hydrolysis or hydration reactions. Arginase converts naturally occurring arginine into ornithine and urea. The enzyme exits in many living organisms, including bacteria and humans (Jenkinson et al., 1996, Comp Biochem Physiol B Biochem Mol Biol, 114:107-32).

Pegylation of Arginase

Arginase may be used as therapeutic agent and administered parenterally for various indications. However, parenterally administrated arginase, which is a protein, may be immunogenic and have a short pharmacological half-life. Consequently, it can be difficult to achieve therapeutically useful blood levels of the proteins in patients. These problems may be overcome by conjugating the proteins to polymers such as polyethylene glycol (PEG).

Covalent attachment of the inert, non-toxic, biodegradable polymer PEG, to molecules has important applications in biotechnology and medicine. Pegylation of biologically and pharmaceutically active proteins has been reported to improve pharmacokinetics, resulting in sustained duration, improve safety (e.g. lower toxicity, immunogenicity and antigenicity), increase efficacy, decrease dosing frequency, improve drug solubility and stability, reduce proteolysis, and facilitate controlled drug release (Roberts et al., 2002, Adv Drug Deliv Rev, 54:459-76; Harris & Chess, 2003, Nat Rev Drug Discov, 2:214-221).

PEG-protein conjugates produced by conventional methods in the art contain heterogeneous species, each being attached with a variable number of PEG molecules, ranging from zero to the number of amino groups that the protein has. Even for species that has the same number of PEG molecule attached, the site of attachment on the protein may vary from species to species. Such non-specific pegylation, however, can result in conjugates that are partially or virtually inactive. Reduction of activity may be caused by shielding the protein's active receptor binding domain when the PEG is attached at a improper site. Thus, there is a clear need for a better way of producing homogeneously pegylated protein molecules which retain the activity of the parent protein and making possible the administration of correct and consistent dosages necessary for clinical uses.

Cancer Treatment Via Amino Acid Deprivation

Amino acid deprivation therapy is an effective means for the treatment of some cancers. Although normal cells do not require arginine, many cancer cell lines are auxotrophic for this amino acid. Many lines of evidence have shown that in vitro arginine depletion, either with an arginine-degrading enzyme or using arginine-deficient medium, leads to rapid destruction of a wide range of cancer cells (Scott et al., 2000, Br J Cancer, 83:800-10). But direct use of enzymes, which are proteins, has problems of immunogenicity, antigenicity and short circulating half-life.

Inhibition of Virus by Arginine Deprivation

Viral infections are among the leading causes of death with millions of deaths each year being directly attributable to several viruses including hepatitis and human immunodeficiency virus (HIV). However, there are several problems with current anti-viral therapies. First, there are relatively few effective antiviral drugs. Many of the existing anti-virals cause adverse or undesirable side-effects. Most effective therapies (such as vaccination) are highly specific for only a single strain of virus. Frequently the virus undergoes mutation such that it becomes resistant to either the drug or vaccine. There is a need for methods for inhibiting viral replication which do not have the problems associated with the prior art.

Many studies over the last 30 years have demonstrated that extracellular arginine is required for viral replication in vitro. Historically this has been accomplished by making tissue culture media deficient in arginine and dialyzing the serum used as a supplement in order to achieve arginine free medium. Using this methodology to achieve arginine deprivation results in inhibition of replication of a large number of diverse families of viruses including: adeno virus (Rouse et al., 1963, Virology, 20:357-365), herpes virus (Tankersley, 1964, J Bacteriol, 87: 609-13).

Human Immunodeficiency Virus (HIV)

Acquired immune deficiency syndrome (AIDS) is a fatal disease, reported cases of which have increased dramatically within the past several years. The AIDS virus was first identified in 1983. It has been known by several names and acronyms. It is the third known T-lymphotropic virus (HTLV-III), and it has the capacity to replicate within cells of the immune system, causing profound cell destruction. The AIDS virus is a retrovirus, a virus that uses reverse transcriptase during replication. Two distinct families of HIV have been described to date, namely HIV-1 and HIV-2. The acronym "HIV" is used herein to refer to human immunodeficiency viruses generically. HIV replication is believed to be arginine-dependent, depletion of which would thus inhibit HIV replication.

SUMMARY OF THE INVENTION

One object of the present invention is to provide novel PEG-arginase conjugates substantially homogeneous and having a PEG moiety covalently bound to a specific site at the arginase molecule. Two preferred embodiments of the present invention are $Cys^{45}$-human arginase I (HAI) and $Cys^{161}$-Bacillus caldovelox arginase (BCA).

Another object of the present invention is to provide a method of producing site-directed, mono-pegylated arginase conjugates, which have potent anti-cancer and anti-viral effects. One particular embodiment of the present invention comprises three general steps. The first step is a genetically modification of a gene encoding for an arginase so that the resulting arginase will have a single free cysteine residue at a given position. The second step is expressing the modified gene in a chosen system to produce desired arginase. The expressing system may be human cells or issues, or other organisms including, for example, a bacterial cell, a fungal cell, a plant cell, an animal cell, an insect cell, a yeast cell, or a transgenic animal. The third step is conjugation between the free cysteine residue of the arginase and a maleimide group (MAL) of PEG compound, resulting in a covalent bond between the PEG compound and the free cysteine of the arginase.

Another object of the present invention is to provide a method of treating viral infection via arginine depletion. This treating method employs homogeneous monopegylated arginase to inhibit viruses' replication.

Another object of the present invention is to provide a method of anti-human immunodeficiency virus (HIV). This method employs homogeneous monopegylated arginase to inhibit HIV's replication.

Another object of the present invention is to provide a method of enhancing arginase's enzymatic activity by replacing the valine at position 20 of Bacillus caldovelox arginase (or the corresponding position in HAI and other arginases) with another amino acid residue, for example, proline.

Still another object of the present invention is to provide a method of enhancing arginase's enzymatic activity, which is accomplished by replacing the native metal cofactor manganese with cobalt.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

BRIEF DESCRIPTION OF THE DRAWINGS

FIG. 1 shows the nucleotide sequence of human arginase I (a) (SEQ ID No: 1), its mutated nucleotide sequence designed for site-directed pegylation (b) (SEQ ID No: 2) according to the present invention, the nucleotide sequence of Bacillus caldovelox arginase (c) (SEQ ID No: 3), and its mutated nucleotide sequence designed for site-directed pegylation (d) (SEQ ID No: 4) according to the present invention.

FIG. 2 shows the amino acid sequence of human arginase I (a) (SEQ ID No: 5), its modified amino acid sequence designed for $Cys^{45}$ site-directed pegylation (b) (SEQ ID No: 6) according to the present invention, the amino acid sequence of Bacillus caldovelox arginase (c) (SEQ ID No: 7), and its modified amino acid sequence designed for $Cys^{161}$ site-directed pegylation (d) (SEQ ID No: 8) according to the present invention.

FIG. 3 shows the nucleotide and amino acid sequences of the human arginase I mutant (C168S/C303S) designed for $Cys^{45}$ site-directed pegylation (a) (SEQ ID No: 9 and 10), the alignment of the nucleotide and amino acid sequences of the 6xHis-tagged human arginase I mutant (C168S/C303S) designed for $Cys^{45}$ site-directed pegylation (b) (SEQ ID No: 11 and 12), the nucleotide and amino acid sequences of the Bacillus caldovelox arginase mutant (S161C) designed for $Cys^{161}$ site-directed pegylation (c) (SEQ ID No: 13 and 14), and the alignment of the nucleotide and amino acid sequences of the 6xHis-tagged Bacillus caldovelox arginase mutant (S161C) designed for $Cys^{161}$ site-directed pegylation (d) (SEQ ID No: 15 and 16).

FIG. 6 depicts the time-course for fermentation in a 2-liter fermenter by the E. coli BL21-DE3 containing the arginase gene, showing the results obtained from the batch fermentation (a1) and the results obtained from the fed-batch fermentation (a2); the history plots of the batch fermentation (b1) and the fed-batch fermentation (b2), showing the changes of parameters such as temperature, stirring rate, pH, dissolved oxygen values; the elution profile of the 6xHis-tagged human arginase I mutant from a chelating FF sepharose column (c) with the first peak being protein impurities and the second peak being the purified human arginase I; and the elution profile of the 6xHis-tagged Bacillus caldovelox arginase mutant from a chelating FF sepharose column (d) with the first peak being the protein impurities and the second peak being the purified Bacillus caldovelox arginase.

DETAILED DESCRIPTION OF PARTICULAR EMBODIMENTS OF THE INVENTION

Cloning of Human Arginase I Gene (HAI)

The gene sequence of human arginase I is shown in FIG. 1a (SEQ ID No: 1). The gene for 6xHis-tagged human arginase I (HAI) was generated by polymerase chain reaction (PCR) from the pAED4/HAI plasmid using the following oligonucleotides to generate an NdeI site at 5'-end and BamHI site at 3'-end. Primer HuAr07-F: 5' GAT.ATA.CAT.ATG.CAT. CAC.CAT.CAC 3' (SEQ ID NO: 17) and Primer HuAr08-R: 5' AGT.GCA.GGA.TCC.TTA.CTT.AGG.TGG.GT-T.AAG.GTA.GTC 3' (SEQ ID NO:18). The PCR product was cut with NdeI and BamHI and subcloned into pET3a expression plasmid vector (Strategene).

The pET3a E. coli expression plasmid vector contains a T7 promoter. The T7 promoter is positioned upstream from the gene 10 leader fragment. The correct sequence was confirmed by DNA sequencing the entire coding region for human arginase I (FIG. 1a). This plasmid is referred to as pET3a/HAI.

Cloning of Bacillus caldovelox Arginase Gene (BCA)

The gene sequence of Bacillus caldovelox arginase is shown in FIG. 1c (SEQ ID No: 3). The gene for 6xHis-tagged Bacillus caldovelox arginase (BCA) was cut from the pUC57/BCA plasmid using NdeI and BamHI restriction enzymes. The insert fragment was subcloned into pET3a expression plasmid vector (Strategene).

The correct sequence was confirmed by sequencing the entire coding region for Bacillus caldovelox arginase (FIG. 1c). This plasmid is referred to as pET3a/BCA.

Mutagenesis of HAI

The plasmid pET3a/HAI was used as a template for site-directed mutagenesis according to the QuikChange® site-directed mutagenesis kit (Strategene). The codons for $Cys^{168}$ and $Cys^{303}$ residues were mutated to the codons for $Ser^{168}$ and $Ser^{303}$ respectively using the following mutagenic primers (SEQ ID No: 19, 20, 21, and 22, respectively).

```
Codon for Cys168 mutated to codon for Ser168:
Primer HuAr01-F:
5' GGG.TGA.CTC.CCT.CTA.TAT.CTG.CCA.AGG 3'

Primer HuAr02-R:
5' CCT.TGG.CAG.ATA.TAG.AGG.GAG.TCA.CCC 3'

Codon for Cys303 mutated to codon for Ser303
Primer HuAr03-F:
5' GCA.ATA.ACC.TTG.GCT.TCT.TTC.GGA.CTT.GC 3'

Primer HuAr04-R:
5' GCA.AGT.CCG.AAA.GAA.GCC.AAG.GTT.ATT.GC 3'.
```

Figure 4A:
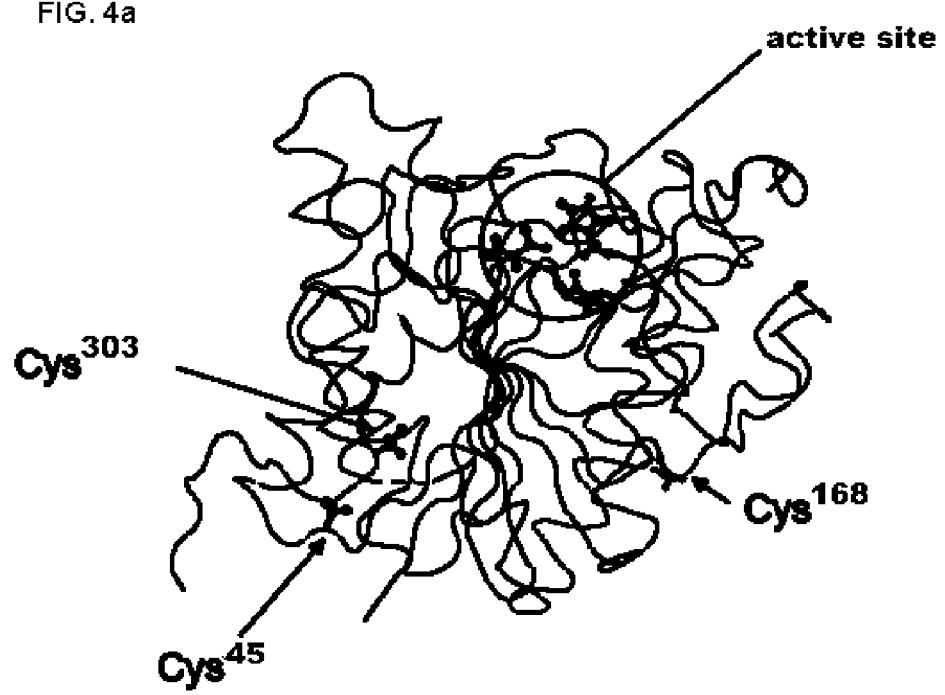
FIG. 4 shows (a) the crystal structure of the wild-type human arginase I (downloaded from NCBI website using Cn3D 4.1 software), showing that $Cys^{45}$ is far away from the active site; (b) the crystal structure of the wild-type Bacillus caldovelox arginase, showing that $Ser^{161}$ is far away from the active site.
Figure 4B:
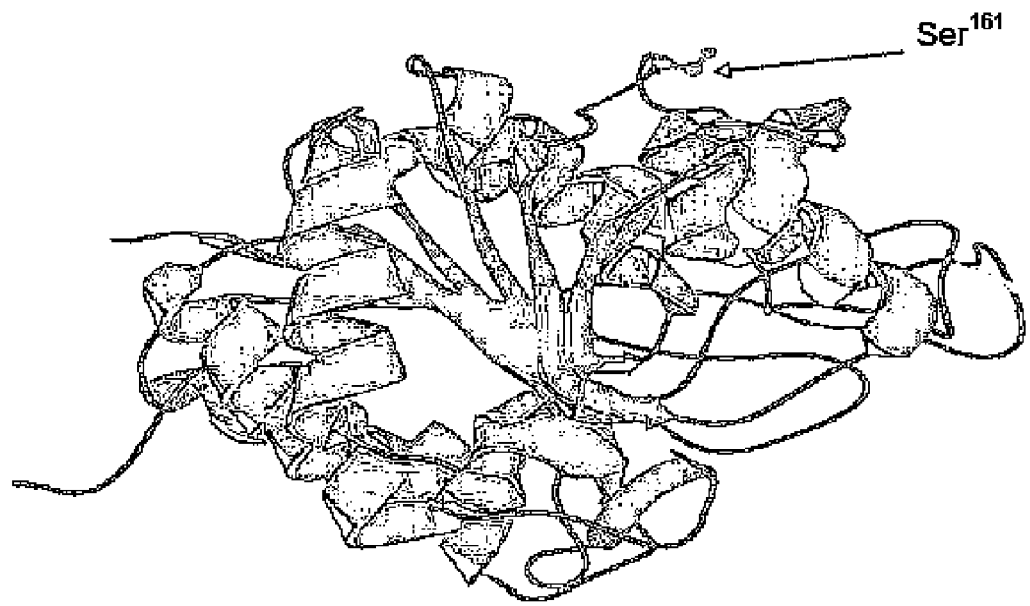

The mutated plasmid was transformed firstly into competent E. coli Top 10 cells. The sequence of mutated plasmid was confirmed by DNA sequencing. The gene sequence of HAI mutant designed for site-directed pegylation is shown in FIG. 1b (SEQ ID No: 2). The mutated plasmid was then transformed into E. coli BL21-DE3 cells for protein expression. The amino acid sequence of the wild-type HAI is shown in FIG. 2a (SEQ ID No: 5). The amino acid sequence of the C168S/C303S mutant is shown in FIG. 2b (SEQ ID No: 6), FIG. 3a (SEQ ID No: 10) and FIG. 3b (SEQ ID No: 12). As shown in FIG. 2b, two cysteine residues in human arginase I were replaced by serine residues. These two serine residues are underlined. The only Cys present is Cys45. This mutant is called C168S/C303S, which only contains one single Cys residue (also underlined). Crystal structure of the wild-type HAI is shown in FIG. 4a. Based on this structure, the rational protein drug design for constructing the C168S/C303S mutant was made. In FIG. 2d, it is shown that one serine residue in Bacillus caldovelox arginase was replaced by cysteine residue. This cysteine residue is underlined. The 6xHis-tag region is also underlined and located at the C terminus. This mutant is called S161C.

Expression and Purification of 6xHis-Tagged Arginases

E. coli BL21-DE3 harboring the plasmid containing a mutated arginase gene encoding 6xHis-tagged human arginase I was grown overnight at 37° C. in LB medium containing 80 μg/mL ampicillin. The inoculum was diluted 1:25 and grown to OD600~0.8 in a shake flask or the inoculum was diluted 1:10 and grown to OD600~15 in a fermentor. The cells were then induced with 0.4 mM IPTG for 4 hours. The bacterial cells were collected by centrifugation, resuspended in 50 mM Tris, 0.1 M NaCl, 10 mM $MnCl_2$, pH 7.4, and disrupted by high pressure homogenization.

Figure 7A:
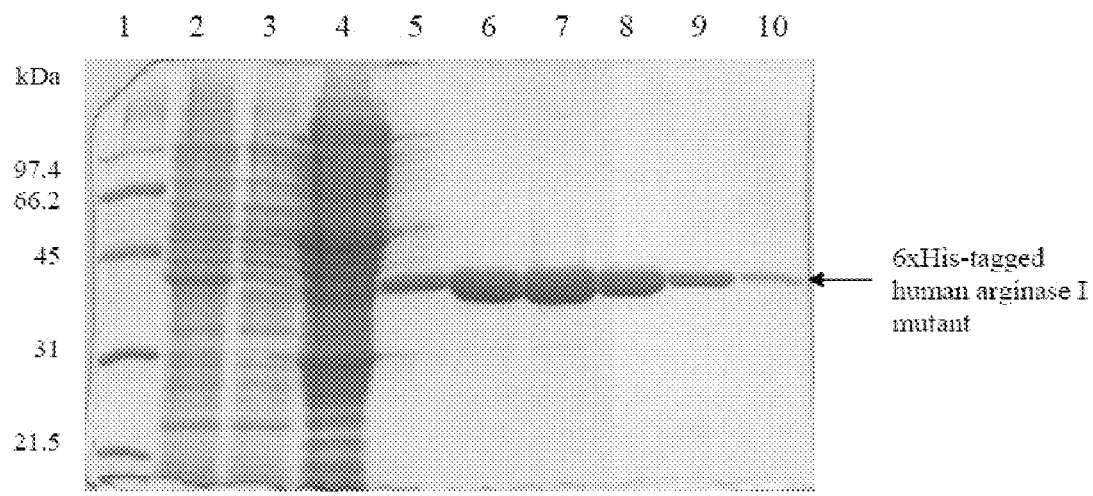
FIG. 7 shows the SDS-PAGE analysis of different fractions involving 6xHis-tagged human arginase I mutant (a) and 6xHis-tagged Bacillus caldovelox arginase mutant (b).
Figure 7B:
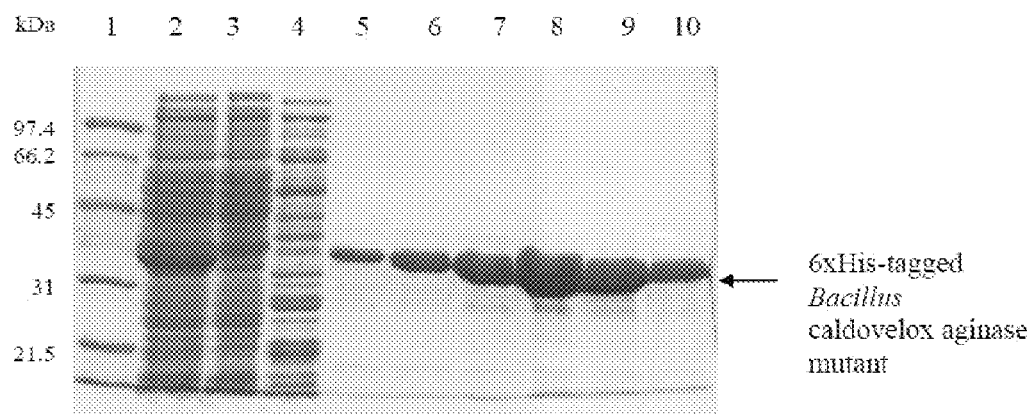

The 6xHis-tagged human arginase I was purified by a chelating FF sepharose (GE Healthcare) column (5.0 cm×9 cm; bed volume of 176 mL) equilibrated with Buffer A (0.02 M sodium phosphate, 0.5 M NaCl, pH 7.4). The 6xHis-tagged arginase were eluted with a gradient of 0.15 to 0.25 M imidazole (FIG. 6a & FIG. 6b). The flow rate was 20 mL/min. The fractions (FIG. 7a & FIG. 7b) containing purified arginase were collected. The yields of purified arginase were about 280 mg/L cell cultures.

The exact procedure as descried above for 6xHis-tagged human arginase I was repeated to obtain purified 6xHis-tagged Bacillus caldovelox arginase.

Site-Directed Pegylation of 6xHis-Tagged Arginases

Figure 5A:
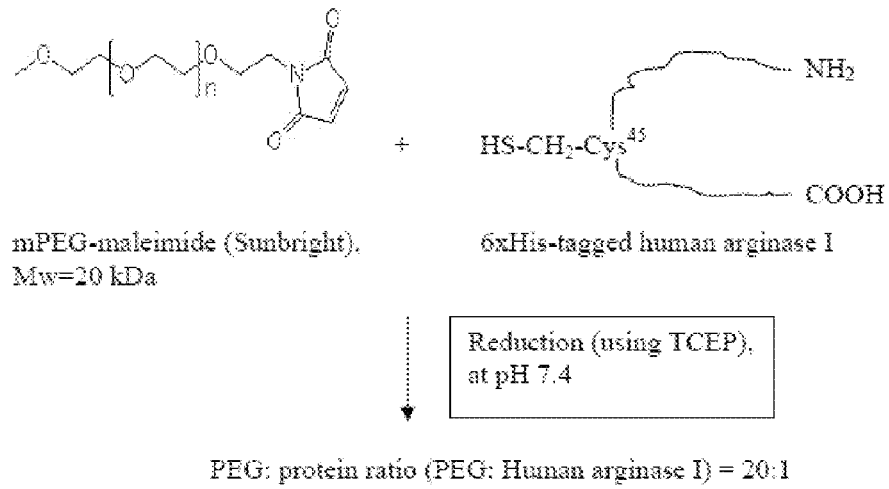
FIG. 5 shows (a) the conjugation procedures for $Cys^{45}$-specific mono-pegylation of the 6xHis-tagged human arginase I mutant with a single chain mPEG-maleimide (20 kDa), showing that the double bond of a maleimide undergoes an alkylation reaction with a sulfhydryl group to form a stable thioether bond, and (b) the corresponding procedures for $Cys^{161}$-specific mono-pegylation of the 6xHis-tagged Bacillus caldovelox arginase mutant.
Figure 5B:
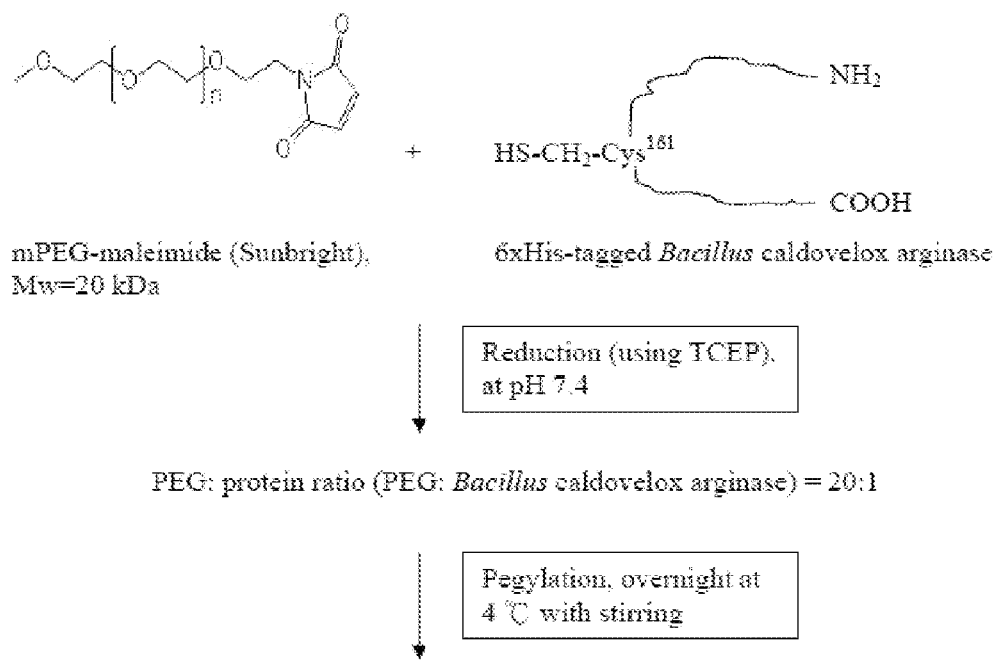

FIG. 5a shows the procedures for conjugating $Cys^{45}$-specific mono-pegylation of the 6xHis-tagged human arginase I mutant with a single chain mPEG-maleimide (20 kDa), referred to as "HAI-PEG20". The double bond of a maleimide undergoes an alkylation reaction with a sulfhydryl group to form a stable thioether bond. FIG. 5b shows the conjugation procedures for $Cys^{161}$-specific mono-pegylation of the 6xHis-tagged Bacillus caldovelox arginase mutant with a single chain mPEG-maleimide (20 kDa), referred to as "BCA-PEG20". One gram of 6xHis-tagged arginase was diafiltered into 0.02 M sodium phosphate, 0.5 M NaCl, pH 7.4, using Millipore Tangential Flow Filtration system (500 mL) with 10 K (cut-off) membrane (Millipore). The concentration of arginase was finally diluted to ~2 mg/mL. The reducing agent Tris(2-carboxyethyl)phosphine, TCEP, was added in a molar excess of 10 moles to one mole of arginase for reduction and the solution was gently stirred for 4 hours at room temperature. mPEG-Maleimide or mPEG-MAL (20 kDa) (Sunbright) in a molar excess of 20 moles to one mole of arginase was added to the reduced arginase and stirred for overnight at 4° C.

Figure 8A:
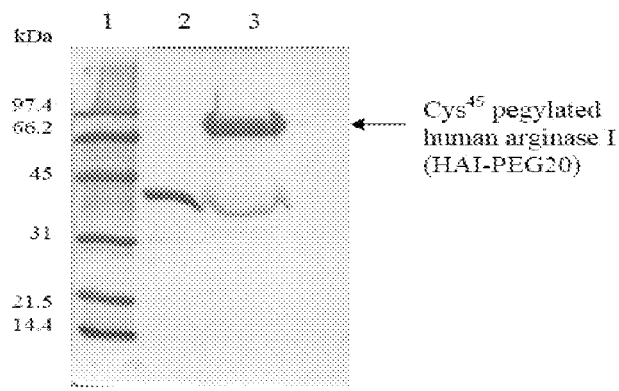
FIG. 8 shows (a) the SDS-PAGE analysis of the unpegylated human arginase I mutant and the $Cys^{45}$ pegylated human arginase I mutant (Lane 1: protein molecular weight marker, Lane 2: unpegylated human arginase I mutant, and Lane 3: $Cys^{45}$ pegylated human arginase I (HAI-PEG20)); (b) the SDS-PAGE analysis of unpegylated Bacillus caldovelox arginase mutant and the $Cys^{161}$ pegylated Bacillus caldovelox arginase (Lane 1: protein molecular weight marker; Lane 2: the unpegylated Bacillus caldovelox arginase mutant; and Lane 3: $Cys^{161}$ pegylated Bacillus caldovelox arginase (BCA-PEG20)).
Figure 8B:
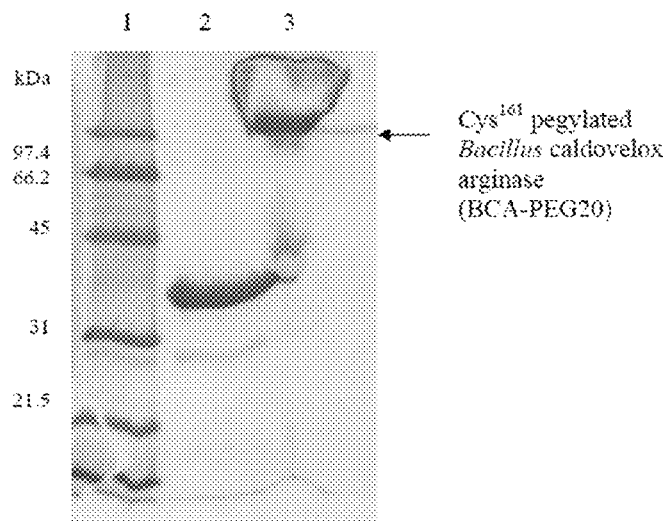
Figure 9A:
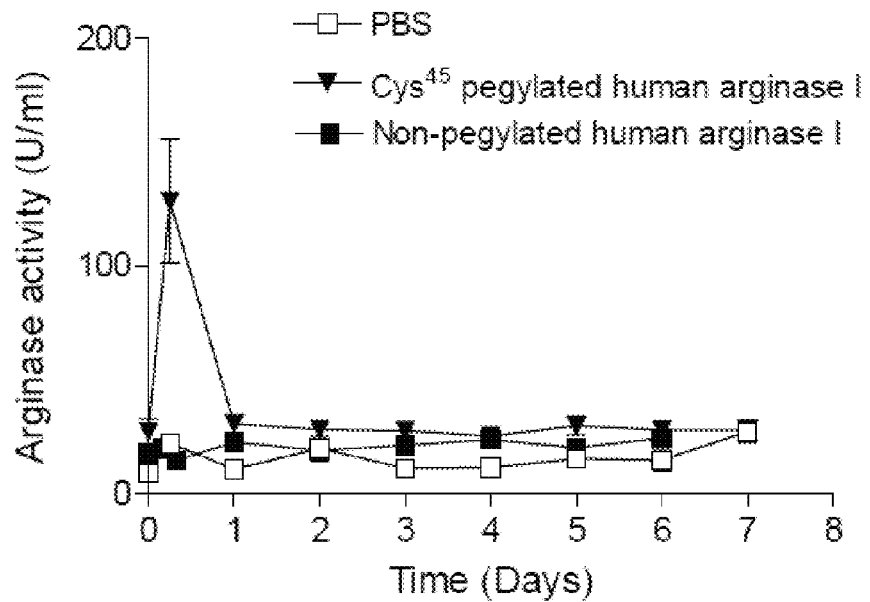
FIG. 9 shows (a) the pharmacokinetic profiles of a single dose of non-pegylated and $Cys^{45}$ pegylated human arginase I (HAI-PEG20) injected intraperitoneally in BALB/c mice, and (b) the pharmacokinetic profiles of a single dose of non-pegylated and $Cys^{161}$ pegylated Bacillus caldovelox arginase (BCA-PEG20) injected intraperitoneally in BALB/c mice.
Figure 9B:
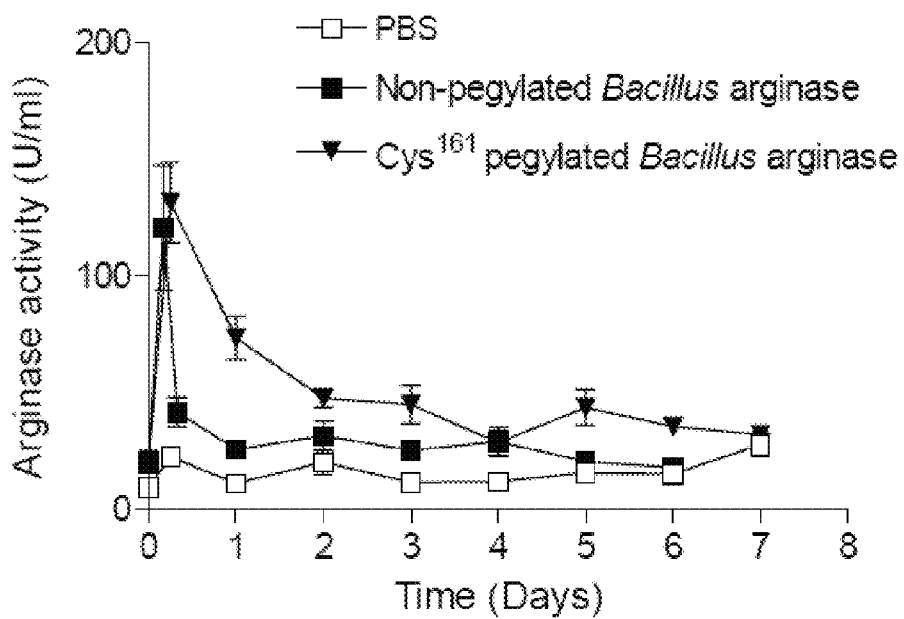

The progress of site-directed pegylation was monitored by SDS-PAGE (FIGS. 8a & 8b). Under the above described conditions, the free sulfhydryl group of cysteine at position 45 on human arginase I was specifically linked via a stable thioether bond to the activated maleimide group of mPEG-MAL (20 kDa). The final products of conjugation comprises predominantly $Cys^{45}$ pegylated human arginase I, unconjugated human arginase I, and mPEG-MAL (20 kDa). Similarly for Bacillus caldovelox arginase, the cysteine residue at position 161 was specifically linked via a stable thioether bond to the activated maleimide group of mPEG-MAL (20 kDa).

The mPEG-MAL (20 kDa) pegylated arginase is advantagous over the mPEG-MAL (5 kDa) pegylated arginase in terms of a loner half-time and advantageous the mPEG-MAL (40 kDa) pegylated arginase in terms of a better solubility.

Batch Fermentation in a 2-Liter Fermenter

The E. coli BL21-DE3 strain containing the arginase gene was stored at −80° C. To prepare the seed inoculums for batch and fed-batch fermentation, 100 μL frozen stock of the aforementioned strain were transferred into 250 mL flask containing 80 mL of fermentation medium. The bacterial culture was cultivated at 37° C. and pH 7.0 in an orbital shaker rotating at 250 rpm. The cultivation was terminated when OD600 nm reached 5.5-6.0 at about 8-10 hours. The 12 mL (1%) seed inoculums was introduced into the 2-L fermenter containing 1200 mL autoclaved enriched fermentation medium. The batch fermentation was carried out at a temperature of 37° C. The pH was maintained at 7.0 by adding sodium hydroxide and hydrochloric acid. The dissolved oxygen level was controlled at above 30% air saturation by introducing air at 1-4 L/min and adjusting the stirring rate of the fermenter at 300-1200 rpm. Isopropyl-beta-D-thiogalacto-P (IPTG) 100 mM, inducer of the protein expression of Bacillus caldovelox arginase (BCA), was introduced into the fermentation broth to a final concentration of 0.5 mM when the OD600 nm was about 11.0 at 5 hours. After the IPTG induction, the fermentation was continued until 9 hours when the OD600 nm was about 16.4. The fermentation cells were harvested for separation and purification of BCA at 4 hours after IPTG induction. The aforementioned strain produced active BCA in an amount of about 105 mg/L of the fermentation medium. The time-course of the fermentation is plotted in FIG. 6a1. The history plot of this batch fermentation showing the changes of parameters such as temperature, stirring rate, pH and dissolved oxygen values is depicted in FIG. 6b 1.

Fed-Batch Fermentation in a 2-L Fermenter

The Fed-batch fermentation with high cell density culture was carried out at 37° C., pH 7.0 and dissolved oxygen was kept above 30% air saturation during the whole fermentation process. The procedure for preparing the seed inoculums was similar to that of the batch fermentation described above. The fermentation was initially started with batch cultivation strategy by introducing 5 mL (1%) seed inoculums into the 2-L fermenter containing 500 mL autoclaved enriched fermentation medium. The dissolved oxygen decreased gradually to around 30% air saturation during the growth phase in batch cultivation period. Once the dissolved oxygen level increased above 80%, representing the depletion of carbon source, the $PO_2$ stat fed-batch strategy was started with the addition of feeding enriched medium. In this strategy, the feeding rate was adjusted to maintain the dissolved oxygen level below 60%, which provided minimal but adequate amount of carbon source during fermentation process. Isopropyl-beta-D-thiogalacto-P (IPTG) 100 mM was introduced into the fermentation broth to a final concentration of 0.5 mM when the OD600 nm was about 100 at 18 hours. After the IPTG induction, the fermentation was continued until 28 hours when the OD600 nm was about 186.8. The fermentation cells were harvested for separation and purification of BCA at 10 hours after IPTG induction. The aforementioned strain produced active BCA in an amount of about 1489.6 mg per liter of the fermentation medium, which is higher than all the other reported yields of different types of arginase. The time-course of the fermentation is plotted in FIG. 6a2. The history plot of this batch fermentation showing the changes of parameters such as temperature, stirring rate, pH and dissolved oxygen values is depicted in FIG. 6b2.

Comparison of Batch and Fed-Batch Fermentation

Table 1 below compares the results of batch and fed-batch fermentation. The comparison demonstrates that the fed-batch fermentation is much superior to the batch operation in terms of culture OD600, cell dry weight and yield of BCA per liter culture.

TABLE 1

|  | Batch fermentation | Fed-batch fermentation |
| --- | --- | --- |
| Maximum $OD_{600}$ reached | 16.4 | 186.8 |
| Cell dry weight (g) | 4.9 | 76.6 |
| yield of BCA (mg/L) | 105.0 | 1489.6 |
| yield of BCA (mg/g-cell) | 21.4 | 19.4 |

Purification of Site-Directed Pegylated Arginases

Affinity nickel ion column chromatography was used to separate 6xHis-tagged site-directed pegylated arginases from mPEG-MAL (20 kDa) as described as follows. The final products of conjugation were loaded onto a chelating FF sepharose (GE Healthcare) column (5.0 cm×9 cm; bed volume of 176 mL) equilibrated with Buffer A (0.02 M sodium phosphate, 0.5 M NaCl, pH 7.4). The column was washed with 5 column volumes of Buffer A to remove free mPEG-MAL (20 kDa). The pegylated arginase was eluted using a salt gradient from 30% to 100% of Buffer B (0.02 M sodium phosphate, 0.5 M NaCl, 0.5 M imidazole, pH 7.4) for 5 column volumes. The protein content of the eluent was monitored at 280 nm wave length. The column was eluted at a flow rate of 20 mL/min and the pegylated arginase fractions were collected. The pooled fractions were diafiltered into PBS buffer (Gibco) and concentrated to 4-6 mg/mL. Before animal study, the endotoxin in the protein drug was removed using a Q-filter (Sartoris).

In Vitro Cytotoxicity of Site-Directed Pegylated Arginases

In vitro cytotoxicity of $Cys^{45}$ pegylated human arginase I and $Cys^{161}$ pegylated Bacillus caldovelox arginase were studied by standard MTT assay in different human cancer cells (melanoma, hepatocellular carcinoma, gastric adenocarcinoma, colorectal adenocarcinoma, pancreatic carcinoma, pancreatic adenocarcinoma, and T cell leukaemia).

The known numbers of cells (5000) were incubated for 68 hr in each well of 96-well plate in a 5% $CO_2$ incubator at 37° C. in the presence of different concentrations of $Cys^{45}$ pegylated human arginase I and $Cys^{161}$ pegylated *Bacillus caldovelox* arginase. After 68 hr of drug incubation, 50 µg of the MTT (3-(4,5-Dimethylthiazol-2-yl)-2,5-diphenyltetrazolium bromide, a tetrazole) solution was added in each well and incubated for another 4 hr. The supernatant was discarded and 100 µL of 10% SDS/0.01 M HCl was added in each well and then incubated overnight. The absorbance was recorded at 540 nm by a microplate reader (Bio-Rad). The concentration of each drug required to inhibit the 50% cell growth ($IC_{50}$) was determined for different cancer cell lines. Experiment was performed in triplicate.

The $IC_{50}$ values of $Cys^{45}$ pegylated human arginase I and $Cys^{161}$ pegylated *Bacillus caldovelox* arginase for different cell lines were calculated and the results are listed in Table 2. As *Bacillus caldovelox* arginase was never known for anti-cancer response, it is thus the first time to have demonstrated its anti-cancer properties and efficacies. In various melanoma cell lines (SK-MEL-2, SK-MEL-28, A375), the $IC_{50}$ values of $Cys^{45}$ pegylated human arginase I were lower when compared to those of $Cys^{161}$ pegylated *Bacillus caldovelox* arginase. Among different hepatocellular carcinoma cell lines (HepG2, Hep3B, PLC/PRF/5), HepG2 cells were most sensitive to both $Cys^{45}$ pegylated human arginase I and $Cys^{161}$ pegylated *Bacillus caldovelox* arginase. Taken together, all liver cancer (HCC) and melanoma cell lines tested were inhibited efficiently by BCA-PEG20 and HAI-PEG20.

$Cys^{161}$ pegylated *Bacillus caldovelox* arginase was also tested for the other five cancer cell lines including gastric adenocarcinoma, colorectal adenocarcinoma, pancreatic carcinoma, pancreatic adenocarcinoma, and T cell leukaemia. For gastric adenocarcinoma cell lines, the $IC_{50}$ of $Cys^{161}$ pegylated *Bacillus caldovelox* arginase for MKN-45 cells (0.798 U/mL) was similar to AGS cells (0.662 U/mL). Among different colorectal adenocarcinoma cell lines (WiDr, HT-29, SW1116), WiDr cells and HT-29 cells were sensitive to $Cys^{161}$ pegylated *Bacillus caldovelox* arginase. When comparing the pancreatic carcinoma cell line (PANC-1) and the pancreatic adenocarcinoma cell line (BxPC-3), the $IC_{50}$ of $Cys^{161}$ pegylated *Bacillus caldovelox* arginase was lower in PANC-1 cells by four-fold. For T cell leukaemia cell line (Jurkat, Clone E6-1), the $IC_{50}$ of $Cys^{161}$ pegylated *Bacillus caldovelox* arginase (0.41 U/mL) was also low when compared to the other cancer cell lines. Taken together, all cancer cell lines tested were sensitive to (and inhibited by) HAI-PEG20 and BCA-PEG20 treatments.

TABLE 2

| | | In vitro $IC_{50}$ | | | |
|---|---|---|---|---|---|
| | | $Cys^{45}$ pegylated human arginase I | | $Cys^{161}$ pegylated *Bacillus caldovelox* arginase | |
| Tumour | Cell line | U/mL | µg/mL | U/mL | µg/mL |
| Melanoma | SK-MEL-2 | 0.079 | 0.80 | 0.612 | 11.25 |
| | SK-MEL-28 | 0.064 | 0.65 | 0.910 | 16.72 |
| | A375 | 0.088 | 0.90 | 0.15 | 2.76 |
| Hepatocellular carcinoma | HepG2 | 0.097 | 0.99 | 2.002 | 36.79 |
| | Hep3B | 0.290 | 2.95 | 9.1 | 57.68 |
| | PLC/PRF/5 | 0.94 | 9.56 | 2.376 | 43.67 |
| Gastric adenocarcinoma | MKN-45 | — | — | 0.798 | 14.67 |
| | AGS | — | — | 0.662 | 12.17 |
| Colorectal adenocarcinoma | WiDr | 0.075 | 0.76 | 0.192 | 3.53 |
| | HT-29 | — | — | 0.220 | 4.04 |
| | SW1116 | 0.41 | 4.18 | 1.515 | 27.84 |
| Pancreatic carcinoma | PANC-1 | — | — | 0.263 | 4.84 |
| Pancreatic adenocarcinoma | BxPC-3 | — | — | 0.846 | 15.54 |
| T cell leukemia | Jurkat, Clone E6-1 | — | — | 0.410 | 7.54 |

Depletion of Arginine by Site-Directed Pegylated Arginases

Pharmacodynamics of $Cys^{45}$ pegylated human arginase I and $Cys^{161}$ pegylated *Bacillus caldovelox* arginase were studied using BALB/c normal mice. The study was carried out in conjunction with the pharmacokinetic study (described below). Therefore, the protocol remained the same. Again, the blood samples collected was centrifuged immediately at 13,200 rpm for 5 minutes and the plasma layer were collected for further analysis using the Amino Acid Analyzer (Biochrom 30, Biochrom Ltd., England).

Figure 10A:
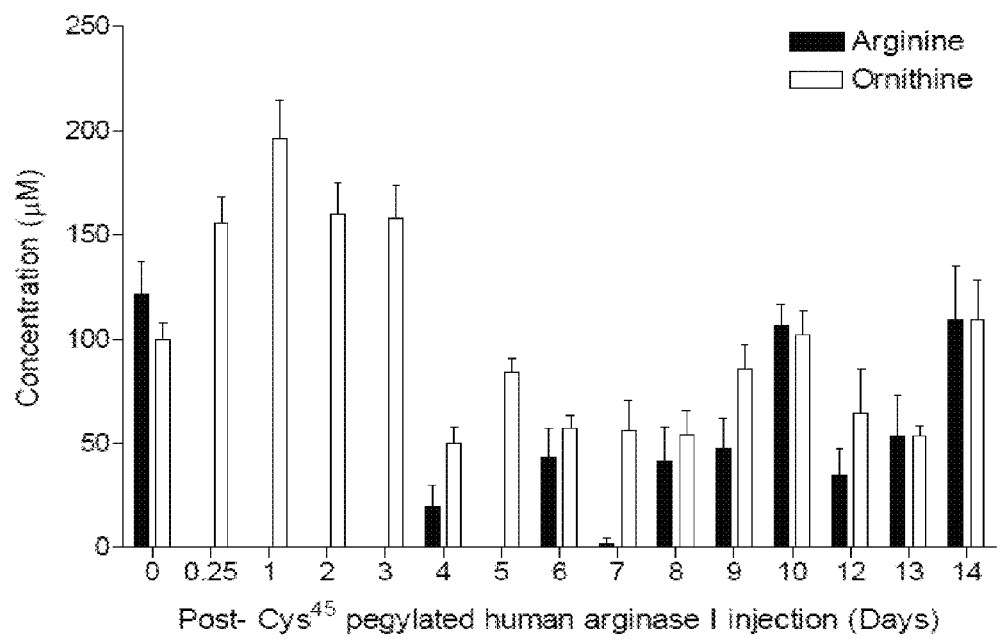
FIG. 10 shows (a) the pharmacodynamic profile of a single dose of $Cys^{45}$ pegylated human arginase I (HAI-PEG20) injected intraperitoneally in BALB/c mice up to Day 14, and (b) the pharmacodynamic profile of a single dose of $Cys^{161}$ pegylated Bacillus caldovelox arginase (BCA-PEG20) injected intraperitoneally in BALB/c mice up to Day 14.

As shown in FIG. 10a, ornithine level started to increase after the injection of $Cys^{45}$ pegylated human arginase I and stayed at a high level (>150 µM) up to Day 3. Arginine was totally depleted starting from 6 hr (Day 0) and started to appear 6.8±2.3 days after arginase administration. This indicated that HAI-PEG20 depleted blood arginine efficiently.

Figure 10B:
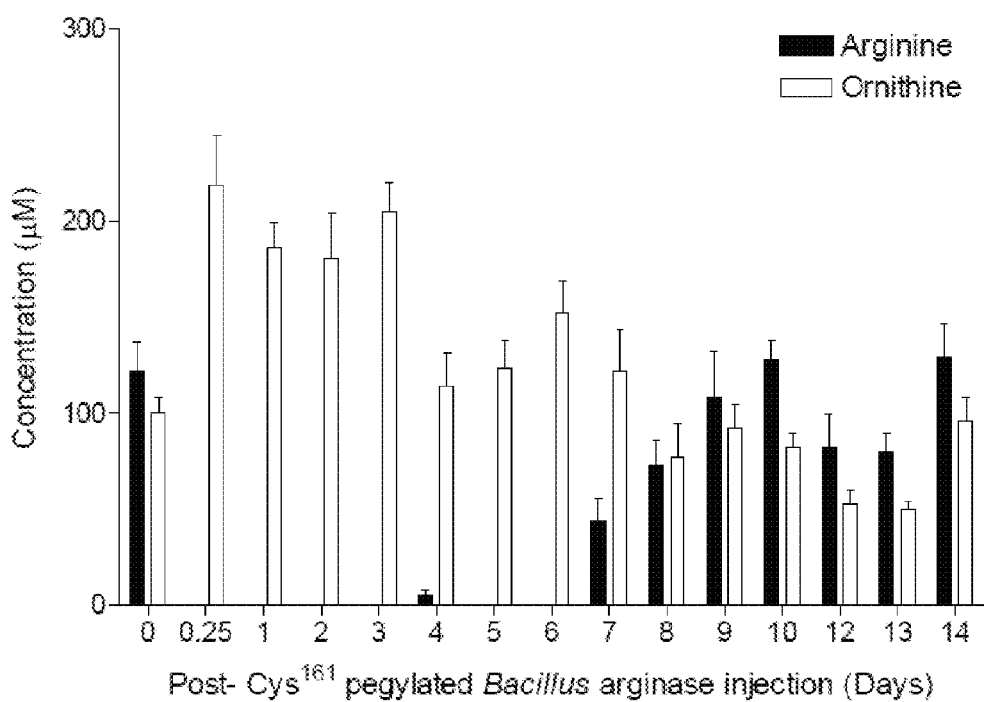

For $Cys^{161}$ pegylated *Bacillus caldovelox* arginase (BCA-PEG20), ornithine level also started to increase and stayed at a high level (>170 µM) up to Day 3 (FIG. 10b). Arginine was totally depleted starting from 6 hr (Day 0) and started to appear 6.7±2.1 days after arginase administration. This indicated that BCA-PEG20 depleted blood arginine efficiently.

Both pegylated arginases ($Cys^{45}$ pegylated human arginase I and $Cys^{161}$ pegylated *Bacillus caldovelox* arginase) displayed a similar pharmacodynamic profile.

In Vivo Anti-Tumour Efficacy on Liver Cancer

In vivo anti-tumour efficacy of non-pegylated (HAI) and $Cys^{45}$ pegylated human arginase I (HAI-PEG20) on liver cancer was then studied.

A number of BALB/c nude mice were injected with hepatocellular carcinoma Hep3B cells intraperitoneally (i.p.) and maintained in vivo. Then each of the 30 BALB/c nude mice was injected with ~1×10$^6$ of the in vivo maintained cancer cells to the right axilla subcutaneously. When palpable tumours of 5 mm diameter were developed, the mice were separated into three different groups (see Table 3). Drugs or PBS buffer were administered intraperitoneally weekly starting on day 0 for 8 weeks. Body weights and tumour dimensions (L: length of the longer diameter and W: length of the shorter diameter of the tumour) were measured twice a week. Tumour volume (½×L×$W^2$) was calculated and plotted against time. After 60 days or when tumour diameter reached 2.5 cm, the mice were euthanized. Survival rates of the mice were recorded at the end of the study.

TABLE 3

In vivo anti-tumour activity protocol

| Group | Testing drug | Mice | Units/mouse | Route |
|---|---|---|---|---|
| 1 | PBS | 5M 5F | n/a | i.p. |
| 2 | Non-pegylated human arginase I | 5M 5F | 500 | i.p. |
| 3 | Cys$^{45}$ pegylated human arginase I | 5M 5F | 500 | i.p. |

Figure 11A:
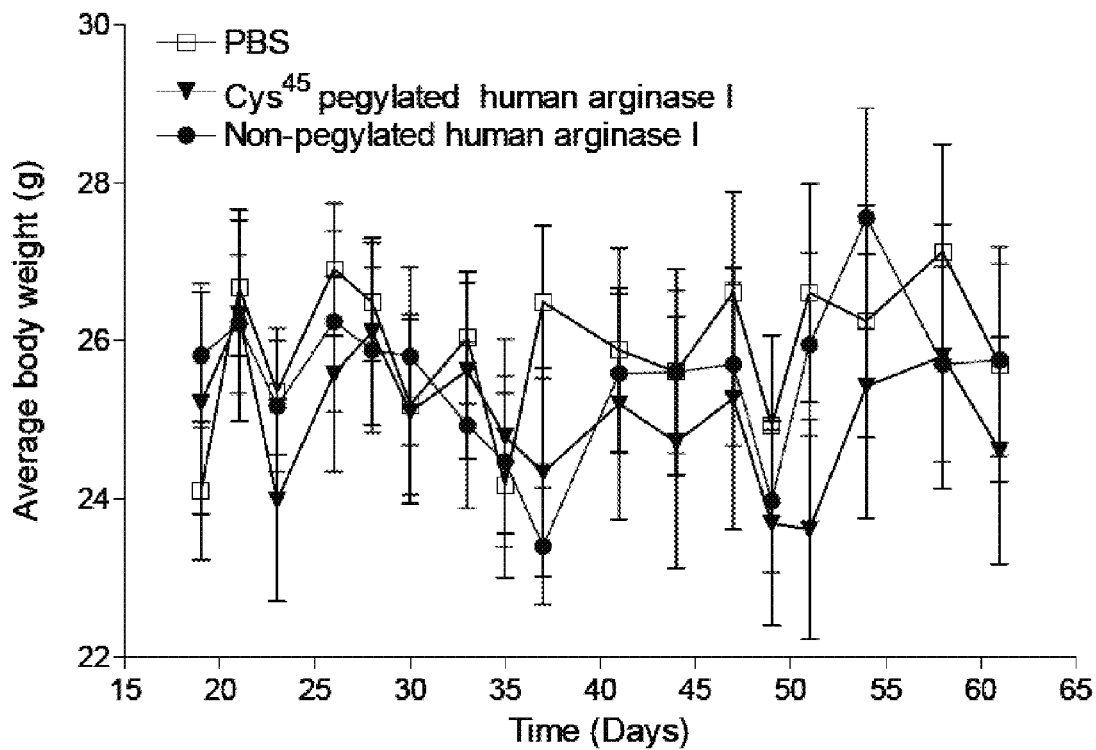
FIG. 11 shows the average body weights (±s.e.m.) of BALB/c nude mice xenografted with Hep3B human liver cancer cells injected with different drugs (a); BALB/c nude mice xenografted with MCF-7 human breast cancer cells injected with $Cys^{161}$ pegylated Bacillus caldovelox arginase (b); BALB/c nude mice xenografted with A549 lungr cancer cells injected with different drugs (c) and BALB/c nude mice xenografted with HCT-15 colorectal cancer cells injected with different drugs (d) during the course of the study.

As shown in FIG. 11a, the average body weights of the PBS control group, the Cys$^{45}$ pegylated human arginase I group, and the non-pegylated human arginase I group were 25.9±0.2 g, 25.0±0.2 g, and 25.5±0.2 g respectively, with no significant change throughout the experiment for each group.

Figure 12A:
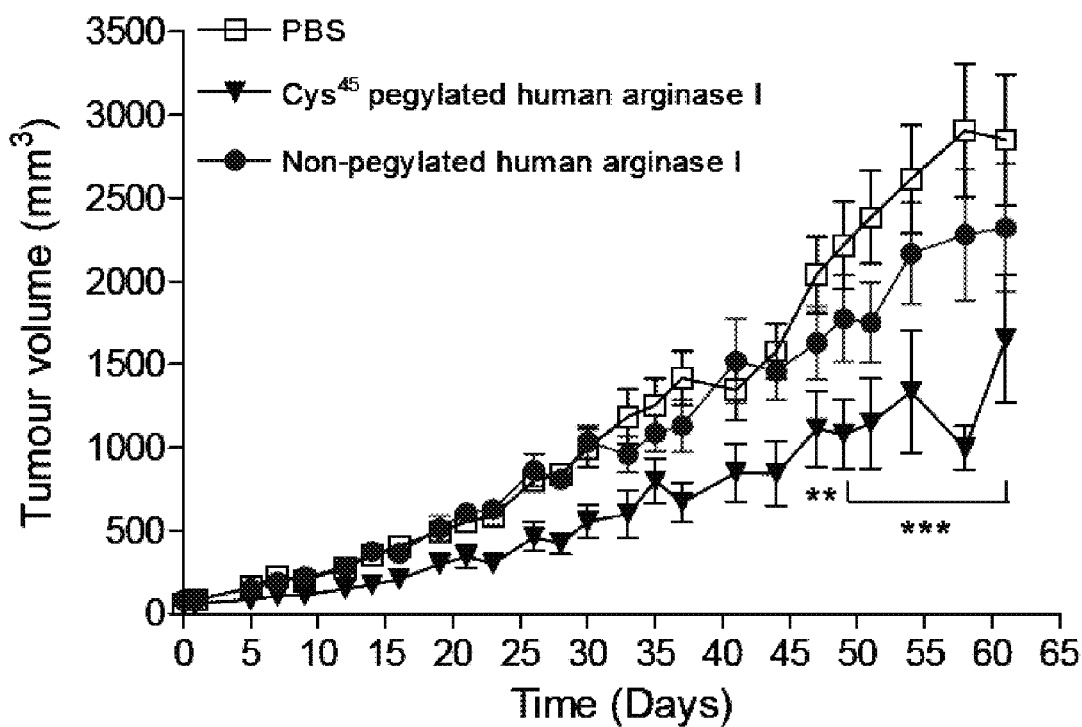
FIG. 12 shows (a) the in vivo activities (efficacies) of non-pegylated and $Cys^{45}$ pegylated human arginase I (HAI-PEG20) in BALB/c nude mice implanted with Hep3B human liver tumour cells subcutaneously; (b) the in vivo activities of $Cys^{161}$ pegylated Bacillus caldovelox arginase (BCA-PEG20) in BALB/c nude mice xenografted with MCF-7 human breast cancer cells subcutaneously; (c) the in vivo efficacies of $Cys^{161}$ pegylated Bacillus caldovelox arginase in BALB/c nude mice bearing A549 lung cancer xenograft subcutaneously, (d) the in vivo efficacies of $Cys^{161}$ pegylated Bacillus caldovelox arginase in BALB/c nude mice bearing A549 lung cancer xenograft subcutaneously (data are expressed as mean number of fold increase in tumor volume±s.e.m); (e) the in vivo efficacies of $Cys^{161}$ pegylated Bacillus caldovelox arginase in BALB/c nude mice bearing HCT-15 colorectal cancer xenograft subcutaneously; and (f) the in vivo efficacies of $Cys^{161}$ pegylated Bacillus caldovelox arginase in BALB/c nude mice bearing HCT-15 colorectal cancer xenograft subcutaneously (data are expressed as mean number of fold increase in tumor volume±s.e.m.).

In terms of the tumour volume, Cys$^{45}$ pegylated human arginase I (HAI-PEG20) significantly reduced the rate of tumour growth starting from Day 47 compared to the PBS control group ($p<0.01$); while non-pegylated human arginase I (HAI) did not show any significant effect ($p>0.05$) (FIG. 12a).

In Vivo Anti-Tumour Efficacy on Breast Cancer

In vivo anti-tumour efficacy of Cys$^{161}$ pegylated *Bacillus arginase* (BCA-PEG20) on breast cancer was determined next.

Athymic nude BALB/c mice (age of 6-8 weeks) were housed under sterile conditions with 12 hour light-dark cycle and provided with autoclaved feed ad libitum. The mice were acclimated for at least 1 week before the start of experiments. Each nude mouse was injected with 1×10$^6$ MCF-7 human breast cancer cells to the right axilla subcutaneously. When palpable tumours of 5 mm diameter were developed, the mice were randomly separated into two different groups (Table 4). Drugs or control vehicle (PBS) were injected intraperitoneally once per week starting from Day 0. Tumour dimensions (L: longest diameter and W: its perpendicular diameter) and body weights were measured on every Mondays, Wednesdays and Fridays with Vernier caliper. Tumour volume was calculated with the formula (½×L×W$^2$) and no. of fold increase in tumour volume was calculated with reference to Day 0. The results were plotted against time. At Day 18 or when tumour diameter reached 2.5 cm, the mice were euthanized and the final tumour and body weight were recorded.

TABLE 4

In vivo anti-tumor activity protocol

| Group | Testing drug | Units/mouse | route | Mice |
|---|---|---|---|---|
| 1 | PBS (control) | N/A | i.p. | 4M 4F |
| 2 | Cys$^{161}$-pegylated *Bacillus caldovelox* arginase | 250 | i.p. | 4M 4F |

Figure 11B:
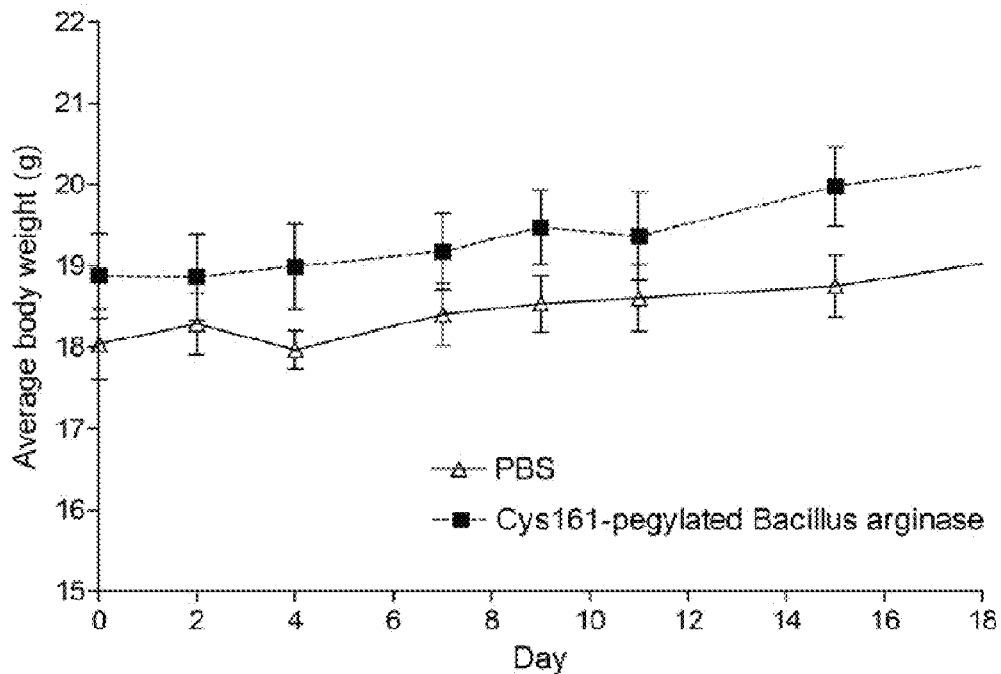
Figure 12B:
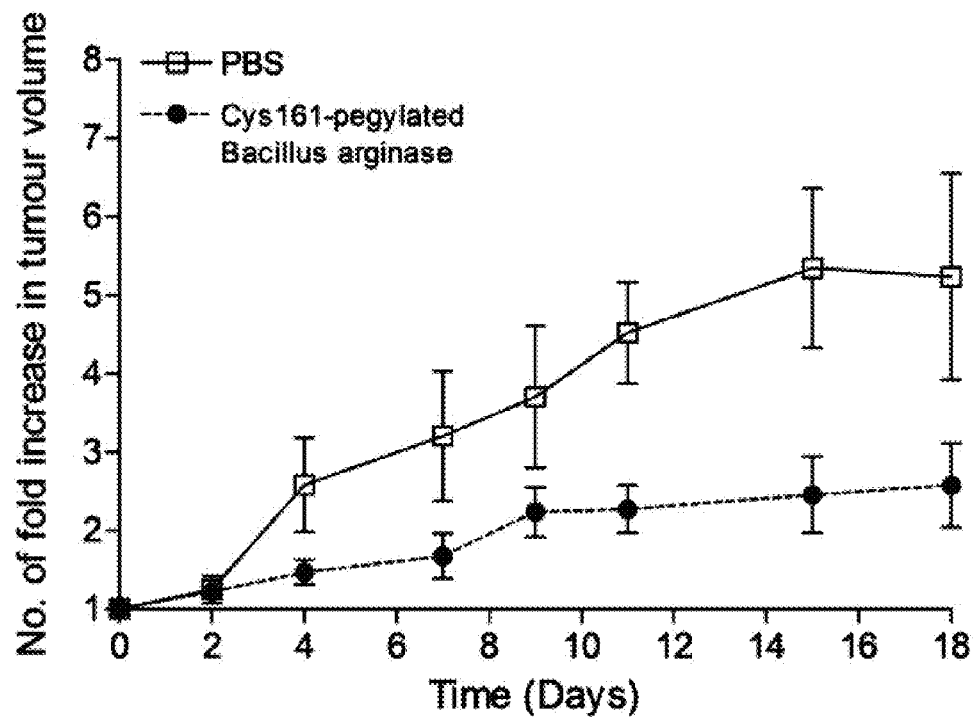

As shown in FIG. 11b, no significant difference in average body weights of the control group (18.76±0.50) and Cys$^{161}$-pegylated *Bacillus caldovelox* arginase (19.76±0.66) was observed throughout the experiment (FIG. 11b). Cys$^{161}$-pegylated *Bacillus caldovelox* arginase significantly suppressed tumour growth and reduced the no. of fold increase in tumour volume in comparion to the PBS control group (2-way ANOVA: $p<0.0001$, FIG. 12b). Using Bonferroni post-test, the reduction is statistically significant starting from Day 15 ($p<0.01$) where the reduction is over 2.8 folds.

In Vivo Anti-Tumour Efficacy on Lung Cancer

Athymic nude BALB/c mice (age of 6-8 weeks) were housed under sterile conditions with 12 hour light-dark cycle and provided with autoclaved feed ad libitum. The mice were acclimated for at least 1 week before the start of experiments. Each nude mouse was injected with 5×10$^6$ A549 human lung cancer cells to the right axilla subcutaneously with matrigel growth supplement. When palpable tumours of ~5 mm diameter were developed, the mice were randomly separated into three different groups (Table 5). Drugs or control vehicle (PBS) were injected intraperitoneally once per week starting from Day 0. Tumour dimensions (L: longest diameter and W: its perpendicular diameter) and body weights were measured on every Mondays, Wednesdays and Fridays with Vernier caliper. Tumour volume was calculated with the formula (½×L×W$^2$) and no. of fold increase in tumour volume (relative tumour volume) was calculated with reference to Day 0.

TABLE 5

In vivo anti-tumor activity protocol

| Group | Testing drug | Units/mouse | route | Mice |
|---|---|---|---|---|
| 1 | PBS (control) | N/A | i.p. | 5M 5F |
| 2 | Unpegylated *Bacillus caldovelox* arginase | 250 | i.p. | 5M 5F |
| 3 | Cys$^{161}$-pegylated *Bacillus caldovelox* arginase | 250 | i.p. | 5M 5F |

Figure 11C:
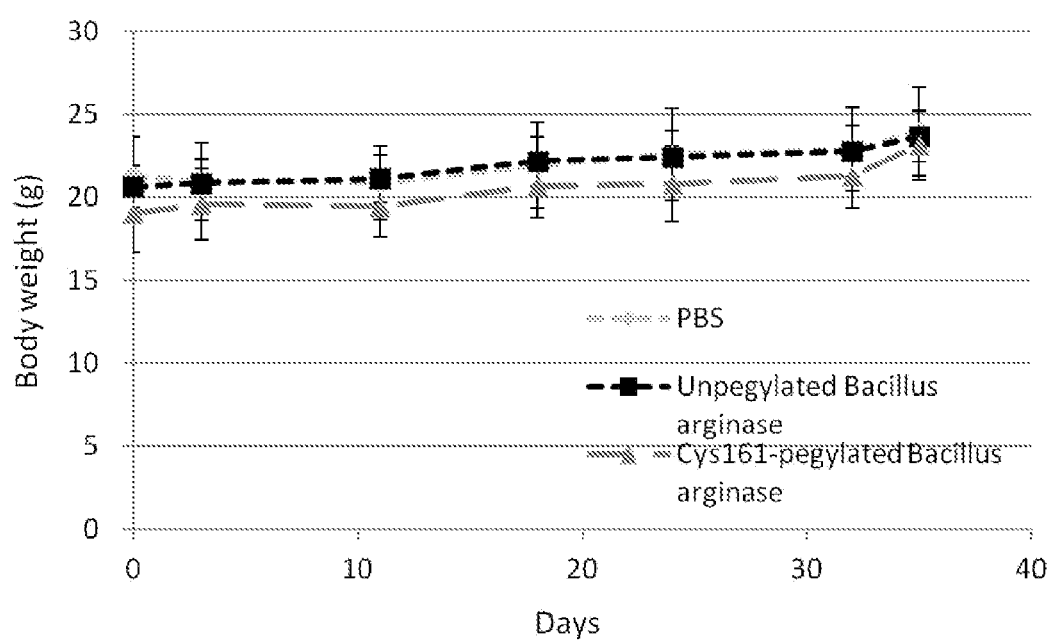

No significant difference in average body weights between different groups was observed throughout the experiment and last recorded as 23.98±2.68 g for the control group, 23.68±1.50 g for the unpegylated *Bacillus caldovelox* arginase and 23.16±2.08 g for the Cys$^{161}$-pegylated *Bacillus caldovelox* arginase at the end of experiment (FIG. 11c).

Figure 12C:
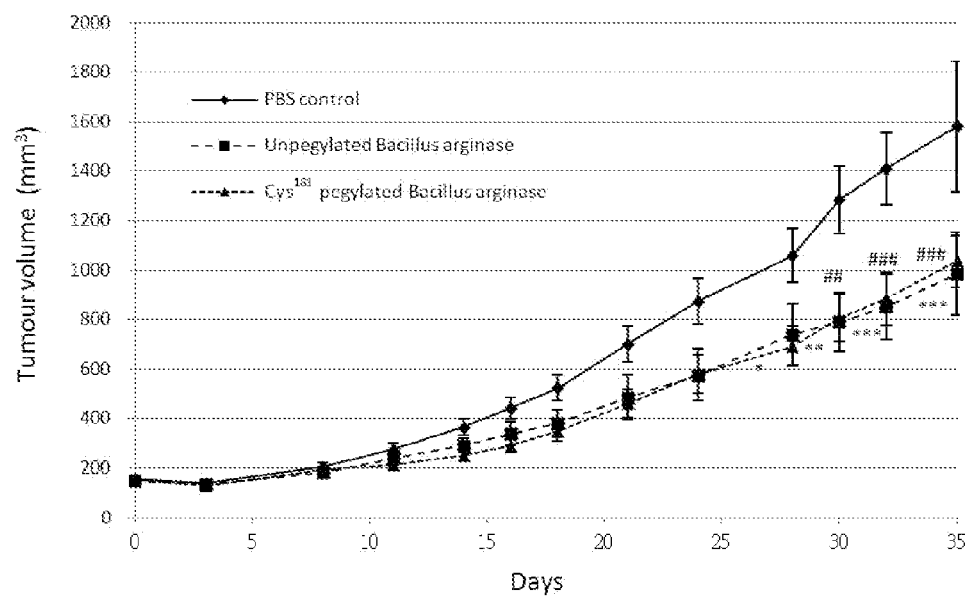
Figure 12D:
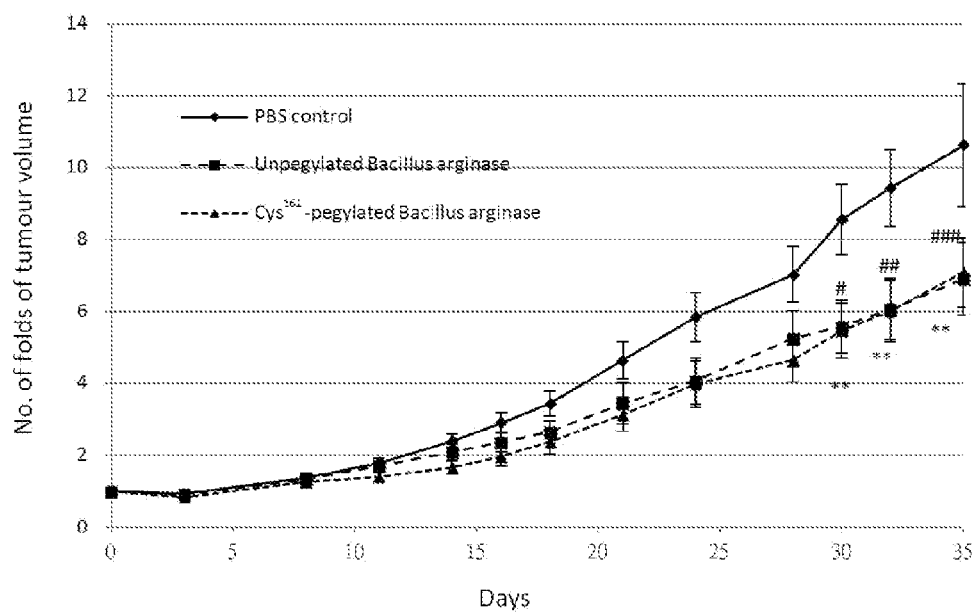

Cys$^{161}$-pegylated *Bacillus caldovelox* arginase (BCA-PEG20) however suppressed tumour growth significantly and statistically in comparison to vehicle control group in terms of progressive changes of tumour volume (FIG. 12c) and no. of folds of tumour volume (FIG. 12d). Two-way ANOVA showed p values at <0.0001 for both parameters while Bonferroni post-test indicated the difference to start from Day 28 ($p<0.05$) to Day 35 ($p<0.001$) for tumour volume and from Day 30 to Day 35 ($p<0.01$ for all points) for relative tumour volume. The unpegylated *Bacillus caldovelox* arginase (BCA) at the same dose regime also showed anti-lung cancer effects in a similar extent with statistical significance for both parameters (two-way ANOVA, both with $p<0.0001$).

In Vivo Anti-Tumour Efficacy on Colorectal Cancer

In vivo anti-tumour efficacy of non-pegylated (BCA) and Cys$^{161}$ pegylated *Bacillus caldovelox* arginase (BCA-PEG20) on colorectal cancer was determined as follows.

Athymic nude BALB/c mice (age of 6-8 weeks) were housed under sterile conditions with 12 hour light-dark cycle and provided with autoclaved feed ad libitum. The mice were acclimated for at least 1 week before the start of experiments. Each nude mouse was implanted with ~3 mm$^3$ of in vivo maintained HCT-15 human colorectal cancer cells to the right axilla subcutaneously. When stable palpable tumours of ~5 mm diameter were developed, the mice were randomly separated into five different groups (Table 6). Intraperitoneal administrations of arginase drugs or control vehicle (PBS) were given twice per week while 5-fluorouracil was given once per week starting from Day 0. Tumour dimensions (L: longest diameter and W: its perpendicular diameter) and body weights were measured on every Mondays, Wednesdays and Fridays with Vernier caliper. Tumour volume was calculated with the formula (½×L×W$^2$) and no. of fold increase in tumour volume (relative tumour volume) was calculated with reference to Day-0. The results were plotted against time. The mice were euthanized at the end of experiment or when tumour diameter reached 2.5 cm.

TABLE 6

In vivo anti-tumor activity protocol

| Group | Testing drug | Units/mouse | route | Mice |
|---|---|---|---|---|
| 1 | PBS (control) | N/A | i.p. | 4M 4F |
| 2 | Unpegylated *Bacillus caldovelox* arginase | 500 | i.p. | 4M 3F |
| 3 | Cys$^{161}$-pegylated *Bacillus caldovelox* arginase | 250 | i.p. | 4M 3F |
| 4 | Cys$^{161}$-pegylated *Bacillus caldovelox* arginase + 5-Fluorouracil | 250 | i.p. | 4M 3F |
| 5 | 5-Fluorouracil | 10 mg/kg | i.p. | 2M 2F |

Figure 11D:
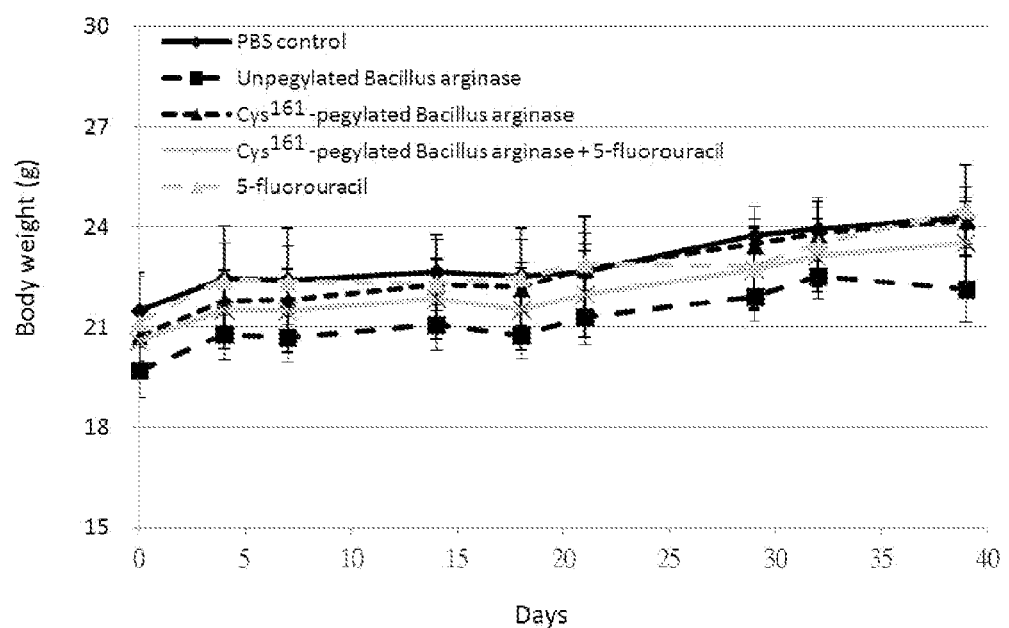

No significant difference in average body weights between different groups was observed throughout the experiment and last recorded as 24.3±0.9 g for the control group, 22.1±1.0 g for the unpegylated *Bacillus caldovelox* arginase group, 24.2±0.7 g for the Cys$^{161}$-pegylated *Bacillus caldovelox* arginase group, 23.5±1.2 g for the Cys$^{161}$-pegylated *Bacillus caldovelox* arginase+5-fluorouracil group and 24.5±1.4 g for the 5-fluorouracil group at the end of experiment (FIG. 11d).

Figure 12E:
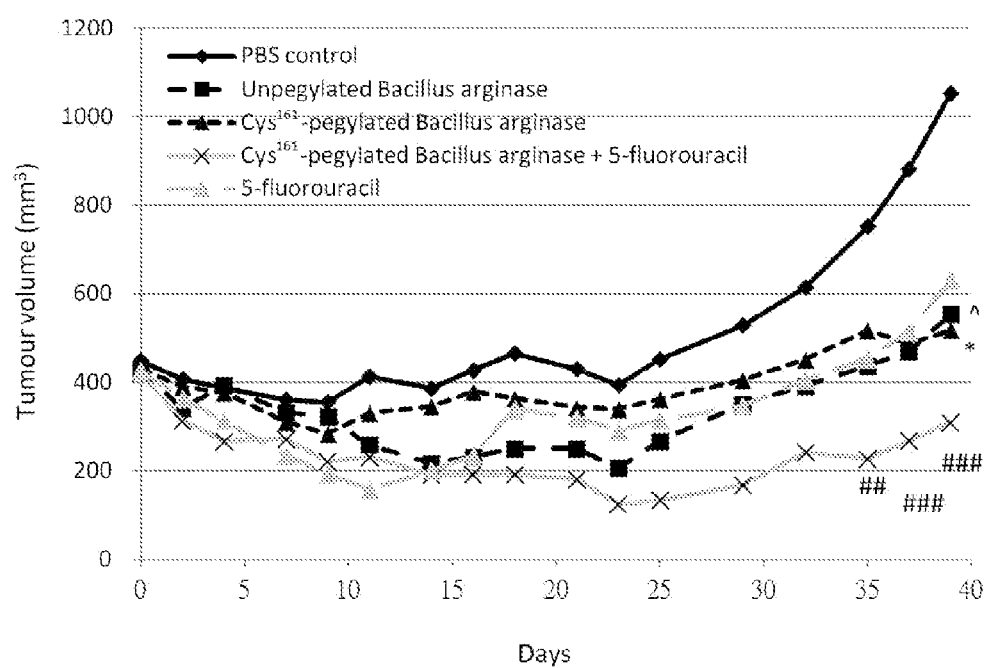
Figure 12F:
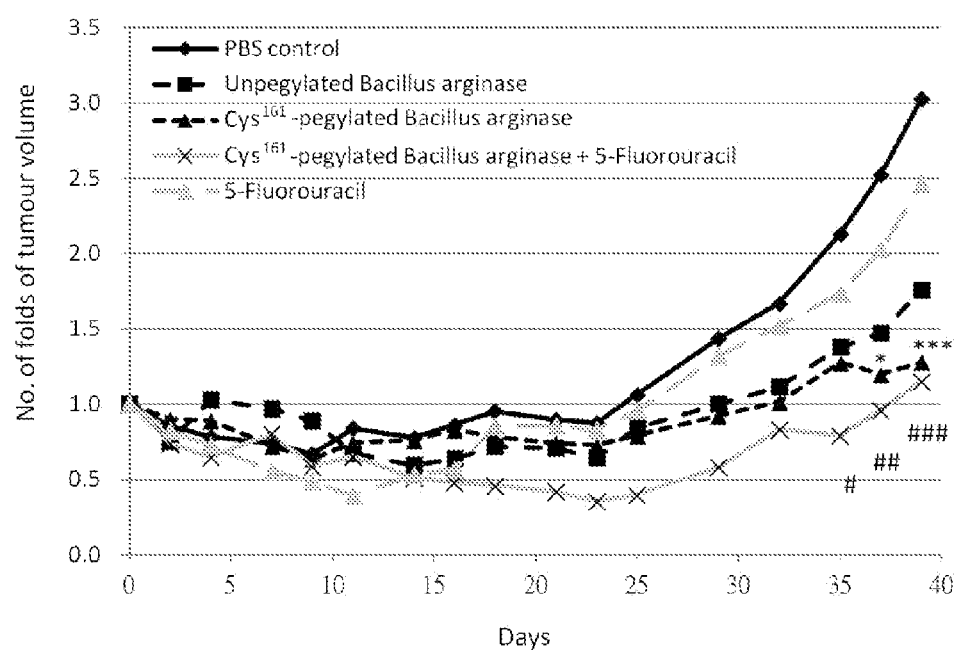

Both Cys$^{161}$-pegylated *Bacillus caldovelox* arginase (BCA-PEG20) and unpegylated *Bacillus caldovelox* arginase (BCA) in all three arginase drugs treated groups suppressed tumour growth with statistical significance (FIG. 12e and FIG. 12f). For the drug combination group (Cys$^{161}$-pegylated *Bacillus caldovelox* arginase plus 5-fluorouracil), two-way ANOVA showed significance for no. of folds of tumour volume and tumour volume with p<0.0001 in both cases. Bonferroni post-test further pinpointed the significant difference for no. of folds of tumour volume to be from Day 36 to Day 40. For Cys$^{161}$-pegylated *Bacillus caldovelox* arginase alone group, two-way ANOVA showed significance for no. of folds of tumour volume and tumour volume with p=0.0005 and p=0.0011, respectively. Bonferroni post-test indicated the difference to be from Day 38 to Day 40 for no. of folds of tumour volume and on Day 40 for tumour volume. For unpegylated *Bacillus caldovelox* arginase group, the p values for no. of folds of tumour volume and tumour volume were 0.0202 and <0.0001, respectively. The 5-fluorouracil group did not show significant tumour suppression in terms of no. of folds of tumour volume (FIG. 12f). The drug combination group resulted in statistically significant lower tumour volume and no. of folds of tumour volume than both the Cys$^{161}$-pegylated *Bacillus caldovelox* arginase alone group (p<0.0001 and p=0.0120, respectively) and the 5-fluorouracil alone group (p=0.0158 and p=0.0434, respectively). The results indicated a synergistic therapeutic effect for the Cys$^{161}$-pegylated *Bacillus caldovelox* arginase and 5-fluorouracil.

In Vivo Inhibitory Efficacy on Breast Cancer Metastasis $1 \times 10^5$ cells of a mouse metastatic breast cancer cell line (4T1) were injected orthotopically into the No. 4 inguinal mammary fat pad of wild-type BALB/c mice at the age of 6-8 weeks. When the tumors reached an average of 5 mm, the mice were divided into two different treatment groups (Table 7). BCA-PEG20 (250 U/mouse) or control vehicle (PBS) were injected intraperitoneally twice per week starting from Day 0. Body weight was measured every week. After three weeks, the mice were sacrificed and analyzed for the lung metastasis. The number of lung metastases was counted under a dissecting microscope after rinsing with PBS.

No significant difference in averaged body weight between different groups was observed throughout the experiment and last recorded as 21.8 g for control group and 21.5 g for the BCA-PEG20 group at the end of experiment.

Results demonstrate that BCA-PEG20 reduced the spontaneous lung tumor nodule formation compared with the PBS vehicle group. The spontaneous lung metastases were too numerous to count in PBS group but only 4 nodules on the average were found in the BCA-PEG20 treatment group (Table 8). The result demonstrates that arginine depletion by BCA-PEG20 inhibits breast tumor metastasis.

TABLE 7

In vivo anti-metastasis protocol

| Group | Testing drug | Units/mouse | route | Mice |
|---|---|---|---|---|
| 1 | PBS (control) | N/A | i.p. | 1M |
| 2 | BCA-PEG20 | 250 | i.p. | 2M |

TABLE 8

| Group | Testing drug | Spontaneous lung metastases |
|---|---|---|
| 1 | PBS (control) | TNTC* |
| 2 | BCA-PEG20 | 4 |

Effect on HIV (HAI-PEG20)

The 50% inhibition concentration (IC$_{50}$) of the Cys$^{45}$ pegylated human arginase I (HAI-PEG20) on human immunodeficiency virus (HIV) was determined as a measure of its effect on HIV.

The efficiency of an antiviral drug can be estimated using cell culture models for viral replication. The HIV replication assay utilizes H9 cells and HIV-1 strain RF. H9 cells, derived from human T lymphocytes, are highly susceptible to infection by CXCR4-using HIV-1 isolates, and show clear signs of cytopathic effects a few days post infection. HIV-1 strain RF is a CXCR4-using class B isolate that replicates to high levels in H9 cells.

H9 cells were seeded in four 96-well plates at $5 \times 10^4$ viable cells/mL and the cultures incubated at 37° C. The following day, two 96-well plates were inoculated with HIV-1 at 0.005 multiplicity of infection (50 μL per well).

Twenty-four hours after infection, the cells of one infected 96-well plate were treated with the Cys$^{45}$ pegylated human arginase I (HAI-PEG20) diluted to a final concentration of 1 U/mL, 10 U/mL and 50 U/mL in tissue culture medium (10% RPMI). Eight replicates were tested for each drug concentration and 100 μL were added per well.

Azido-thymidine (AZT) was used as a benchmark drug for this assay to ensure that a dose response was obtained. This was diluted appropriately (0.01, 0.1 and 1 μg/mL) in 10% RPMI and added to the second infected plate. Eight replicates were tested for each drug concentration and 100 μL were added per well.

A cytotoxicity control was set up in parallel; this consisted of one 96-well plate of uninfected cells treated with three drug concentrations (1 U/mL, 10 U/mL and 50 U/mL; 8 replicates per drug concentration). This z could allow the cytotoxic concentration to be determined (CC$_{50}$).

The remaining 96-well plate was inoculated with tissue culture medium alone to serve as the negative control.

Five days post infection plates were examined for cytopathic effect and the IC$_{50}$ of the drug determined by comparing syncytial cell number in drug treated and non-treated cells.

Figure 13:
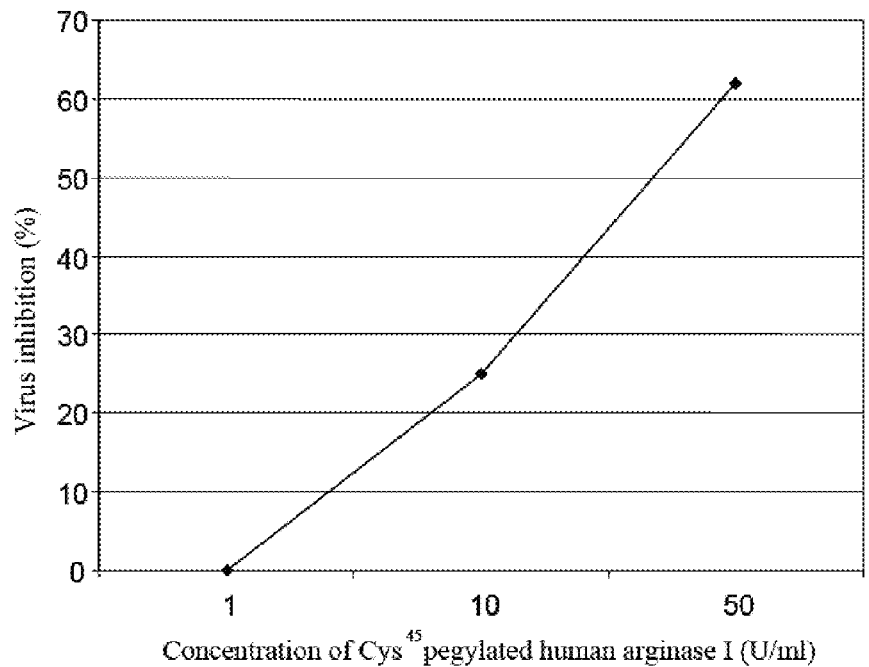
FIG. 13 shows an HIV inhibition assay for $Cys^{45}$ pegylated human arginase I (HAI-PEG20).

The results show that H9 cells inoculated with HIV strain RF had viral infection, whereas H9 cells inoculated with tissue culture medium alone remained healthy throughout the study. Cytopathic effect was observed in the H9 cultures infected with HIV and treated with the $Cys^{45}$ pegylated human arginase I (HAI-PEG20) at all concentrations. Eight out of eight (8/8) infected wells treated with the pegylated enzyme at a final concentration of 1 U/mL, displayed cytopathic effect. For infected wells treated with the enzyme at a final concentration of 10 U/mL, 6/8 wells displayed cytopathic effect. When the drug was tested at the highest final concentration of 50 U/mL, 3/8 wells displayed cytopathic effect. These results are shown in Table 9 and FIG. 13. The $IC_{50}$ of the drug was found to be approximately 37 U/mL.

Figure 14:
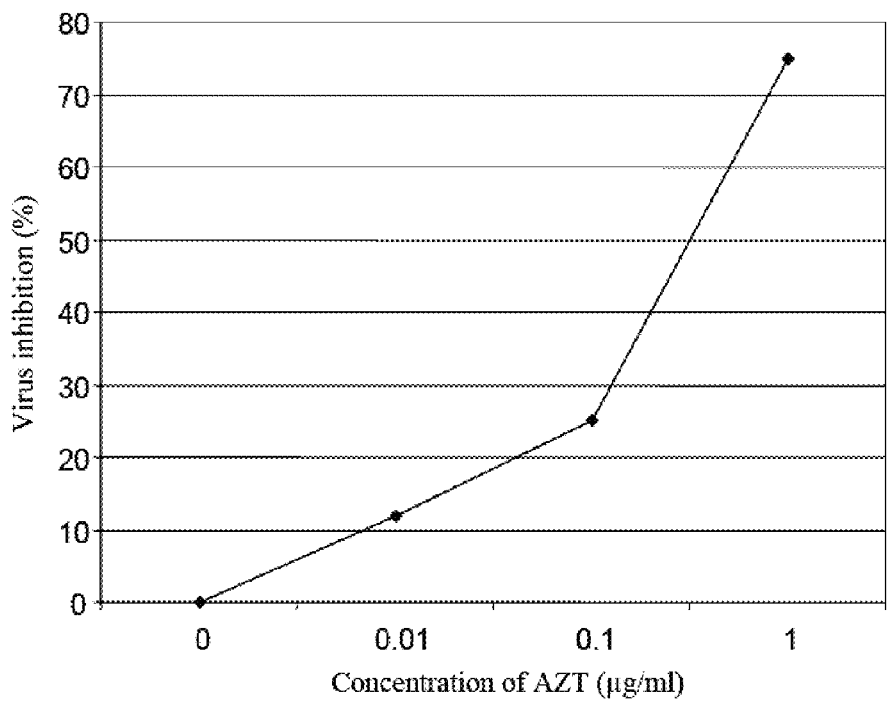
FIG. 14 shows the HIV inhibition assay for azido-thymidine (AZT).

When the benchmark drug AZT was added to infected wells at 0.01 μg/mL, 7/8 wells displayed cytopathic effect. For infected wells treated with AZT at 0.1 μg/mL, 6/8 wells displayed cytopathic effect and when tested at 1 μg/mL, 2/8 wells displayed cytopathic effect. These results are illustrated in FIG. 14. The $IC_{50}$ of the AZT was found to be 0.58 μg/mL.

TABLE 9

Virus inhibition assay

| Sample | Results |
|---|---|
| HIV without $Cys^{45}$ pegylated human arginase I treatment | 24/24 |
| HIV without $Cys^{45}$ pegylated human arginase I treatment (second plate) | 22/24 |
| HIV treated with $Cys^{45}$ pegylated human arginase I (50 U/mL) | 3/8 |
| HIV treated with $Cys^{45}$ pegylated human arginase I (10 U/mL) | 6/8 |
| HIV treated with $Cys^{45}$ pegylated human arginase I (1 U/mL) | 8/8 |
| HIV treated with AZT (0.01 μg/mL) | 7/8 |
| HIV treated with AZT (0.1 μg/mL) | 6/8 |
| HIV treated with AZT (1 μg/mL) | 2/8 |
| Negative control | 0/96 |
| Cytotoxicity control - uninfected cells treated with $Cys^{45}$ pegylated human arginase I (50 U/mL) | 8/8* |
| Cytotoxicity control - uninfected cells treated with $Cys^{45}$ pegylated human arginase I (10 U/mL) | 8/8* |
| Cytotoxicity control - uninfected cells treated with $Cys^{45}$ pegylated human arginase I (1 U/mL) | 8/8* |

Each well was inoculated with 50 μL of HIV at 0.005 multiplicity of infection.
*= cytotoxicity observed in each well, therefore viability counts performed for 1 well for each concentration. The results are recorded as a ratio; e.g. 1/X, where 1 is the no. of positive wells/no. of wells inoculated.

Figure 15:
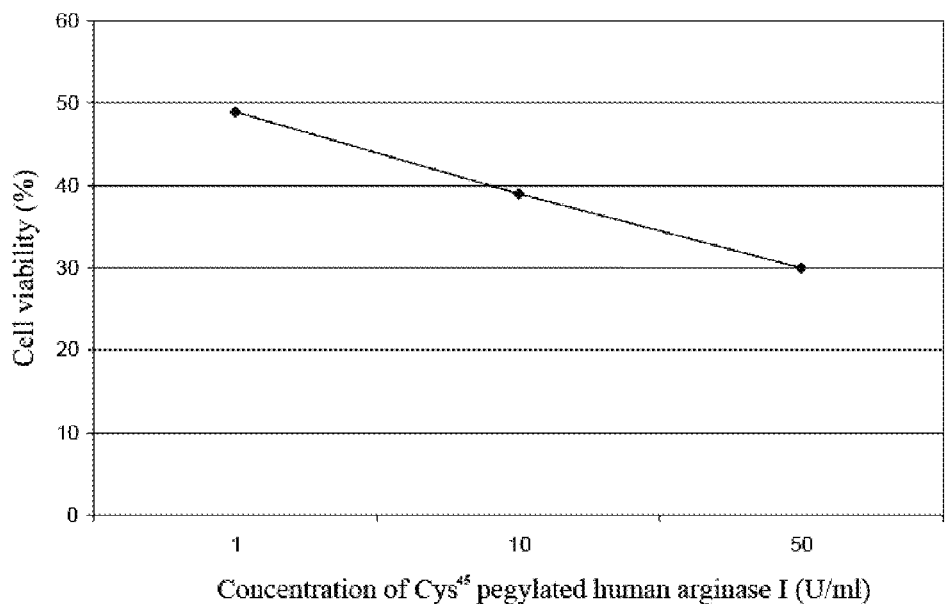
FIG. 15 shows the cytotoxicity of $Cys^{45}$ pegylated human arginase I (HAI-PEG20).

Table 10 presents the viability counts for the cytotoxicity control. In the cytotoxicity test, all wells displayed symptoms of cytotoxicity, therefore viability counts were performed on one well for each concentration of $Cys^{45}$ pegylated human arginase I. The highest concentrations resulted in cell viabilities of 30% and 39% for 50 U/mL, and 10 U/mL respectively. For 1 U/mL, cell viability was 58%. Based on this cell viability was assessed for all 8 wells and the average determined to be 48.9%. This approximates to a 50% reduction in cell viability based on the cell viability of cells (96.8%) when cells were seeded onto the 96 well plates. These results are displayed in Table 10 and FIG. 15, clearly demonstrating that HAI-PEG20 has inhibitory effects on HIV replication.

TABLE 10

Cell viability in cytotoxicity control

| Sample | | Results | | | Average % viability |
|---|---|---|---|---|---|
| | | Live cells | Total cells | % viability | |
| 50 U/mL - 1 well | | 9 | 30 | 30 | N/A |
| 10 U/mL - 1 well | | 11 | 28 | 39 | N/A |

TABLE 10-continued

Cell viability in cytotoxicity control

| Sample | | Results | | | Average % viability |
|---|---|---|---|---|---|
| | | Live cells | Total cells | % viability | |
| 1 U/mL | well 1 | 19 | 33 | 58 | 48.9 |
| | well 2 | 30 | 63 | 48 | |
| | well 3 | 23 | 59 | 39 | |
| | well 4 | 21 | 60 | 35 | |
| | well 5 | 33 | 58 | 57 | |
| | well 6 | 29 | 56 | 52 | |
| | well 7 | 31 | 49 | 63 | |
| | well 8 | 24 | 61 | 39 | |

N/A = not applicable

In Vitro Anti-Cancer Effects

In vitro cancer cell culture studies on the anti-cancer efficacies of different arginine-depleting enzymes were conducted for various cancer types.

Cell Proliferation Assay: For each cancer cell line, cells ($5 \times 10^3$) in 100 μL culture medium were seeded to the wells of a 96-well plate and incubated for 24 hours by standard method. The culture medium was replaced with medium containing different concentrations of one of the arginases or arginine deiminase (ADI). The plates were incubated for an additional 3 days at 37° C. in an atmosphere of 95% air/5% $CO_2$. The metabolically viable cell fraction was determined by the MTT assay, which was performed to estimate the number of viable cells in the culture. Non-linear regression with Prism 4.0 (Graphpad Software) was used to fit a sigmoidal dose response curve, and the amount of each of the arginine-degrading enzymes (in terms of U/mL or unit/ml or μg/mL) needed to achieve 50% inhibition of cell growth was defined as $IC_{50}$.

RT-PCR studies: Total RNA was extracted from cancer cell lines grown in culture using the Qiagen RNeasy kit. For reverse transcription-polymerase chain reaction (RT-PCR), the RNA was first reverse-transcribed into cDNA by iScript cDNA Synthesis kit (Bio-Rad, CA) according to the manufacturer's instruction. Briefly, 5 □g of total RNA was subjected to RT at 42° C. for 30 mM. A 2 μL portion of cDNA was then amplified using 50 μL of reaction mixture containing 0.5 units of iTaq DNA polymerase (Bio-Rad, CA). PCR was performed in a DNA thermal Mycycler (Bio-Rad, CA). The following flanking primers were used:

(a) Human ASS (448 bp product):

```
Sense:
5'-GGGGTCCCTGTGAAGGTGACC-3';

Anti-sense:
5'-CGTTCATGCTCACCAGCTC-3'
```

(b) Human ASL (218 bp product):

```
Sense:
5'-CTCCTGATGACCCTCAAGGGA-3';

Anti-sense:
5'-CATCCCTTTGCGGACCAGGTA-3'
```

(c) Human OTC (221 bp product):

```
Sense:
5'-GATTTGGACACCCTGGCTAA-3';

Anti-sense:
5'-GGAGTAGCTGCCTGAAGGTG-3'
```

(d) Human GAPDH (306 by product):

```
Sense:
5'-AGCCACATCGCTCAGACA-3';

Anti-sense:
5'-GCCCAATACGACCAAATCC-3'
```

The reaction products were subjected to 1% agarose gel electrophoresis. After electrophoresis and staining with ethidium bromide, all PCR product band intensities were analyzed by Lumi-Imager (Boehringer Mannheim, Ind.), and the relative mRNA expression levels were estimated by normalization with the house keeping gene GADPH.

As the results indicate, arginases and ADI are all efficient arginine-degrading enzymes. Unexpectedly, we found that all the cancer cell lines tested here are sensitive to arginases but many cancer cell lines are actually resistant to ADI treatment. It was discovered in the present invention that this difference is due to the fact that arginase converts arginine to ornithine and urea while ADI converts it to citrulline and ammonia. Citrulline can be recycled back to arginine if the cancer cells are ASS-positive and ASL-positive, leading to drug resistance. Most strikingly, if the cancer cells are OTC-negative, they cannot recycle ornithine back to arginine in the cells even if they are ASS-positive and ASL-positive. This guideline provided by the present invention has been found to be consistent with all our data as well as data from other research groups. Under this guideline, for instance, if the cancer cells are either ASS-negative or ASL-negative or both, they would be arginase-sensitive and ADI-sensitive. On the other hand, if the cancer cells are both ASS-positive and ASL-positive but OTC-negative, they would be arginase-sensitive and ADI-resistant. Therefore, it is believed that that arginases have broader anti-cancer applications than ADI. Furthermore, ammonia (product from ADI reaction) is more toxic than urea (product from arginase reaction). Thus, the arginase anti-cancer agents of the present invention are believed to be more safe than ADI.

In vitro anti-cancer efficacy results are summarized in Tables 11a-11g. As indicated in Table 11a, all the melanoma cell lines tested were sensitive to arginase treatments. When arginase was added to culture medium, arginine was converted to ornithine and urea. All these cells were OTC-negative and according to the guideline discussed above, these cells cannot recycle the arginase reaction product ornithine back to arginine in the cells and therefore the cells are inhibited due to the lack of arginine. According to the $IC_{50}$ values, all the arginases tested were very effective on the inhibition of cancer cell growth.

Although all the melanoma cell lines tested were all ASS-positive and ASL-positive, the expression levels of ASS were low, which can be confirmed by performing an ASS activity assay. The low ASS expression level explains why these cell lines were all sensitive to ADI treatments. B16 is a mouse melanoma cell line and it is also sensitive to both arginases and ADI. Thus, it is believed that ADI kills the melanoma cells was due to the low level of ASS expression while arginases kill the melanoma cells because they are OTC-negative.

In Table 11b, it is shown that all the leukemia cell lines tested were sensitive to arginase treatments. Some of these cancer cells tested were OTC-negative and according to the guideline discussed above, these cells cannot recycle the arginase reaction product ornithine back to arginine in the cells and therefore the cells are inhibited due to the lack of arginine. According to the $IC_{50}$ values, all the arginases tested were very effective on inhibition of leukemia cancer cell growth. For ADI treatments, all the 4 leukemia cell lines tested were sensitive except the RPMI8226 cell line, which is resistant to ADI treatment, most likely due to the fact that it is both ASS-positive and ASL-positive. Therefore, for inhibiting leukaemia cells, arginases are advantageous over ADI.

Table 11c shows that all the colorectal cancer cell lines tested were sensitive to arginase treatments. All these cancer cells tested were OTC-negative. In consistent with the guideline discussed above, these cells cannot recycle the arginase reaction product ornithine back to arginine in the cells and therefore the cells are inhibited due to the lack of arginine. According to the $IC_{50}$ values, all the arginases tested were very effective on the inhibition of colorectal cancer cell growth. For ADI treatments, only 2 colorectal cancer cell lines (WiDr and HT29) tested were sensitive and the other 2 (SW1116 and HCT15) were resistant to ADI treatment, most likely due to the fact that they are both ASS-positive and ASL-positive. For HT29, although it was ASS-positive and ASL-positive according to the RT-PCR data, the expression level of ASS was low, as confirmed by performing an ASS activity assay, which explains why this cell line was sensitive to ADI treatment.

Also shown in Table 11c, most strikingly, all the pancreatic cancer cell lines tested were sensitive to arginase treatments. All these cancer cells tested were OTC-negative. As discussed above, these cells cannot recycle the arginase reaction product ornithine back to arginine in the cells and therefore the cells are inhibited due to the lack of arginine. According to the $IC_{50}$ values, all the arginases tested were very effective on the inhibition of pancreatic cancer cell growth. For ADI treatments, only one pancreatic cancer cell line (Panc1) tested was sensitive and the other 2 (BxPC3 and HPAFII) were resistant to ADI treatment. Clearly, for inhibiting pancreatic cancer cells, arginases are better than ADI.

Table 11d shows that all the gastric cancer cell lines tested were sensitive to arginase treatments. All these cancer cells tested were OTC-negative and thus, as discussed above, these cells cannot recycle the arginase reaction product ornithine back to arginine in the cells and therefore the cells are inhibited due to the lack of arginine. As the $IC_{50}$ values indicate, all the arginases tested were very effective on the inhibition of gastric cancer cell growth. In a sharp contrast, all the gastric cancer cell lines tested were resistant to ADI treatment, most likely due to the fact that they are both ASS-positive and ASL-positive. This similar result was obtained for the liver cancer (or HCC) cell lines tested as shown in Table 11e.

Table 11e also shows that the retinoblastoma cancer cell line Y79 tested was sensitive to arginase treatments but resistant to ADI treatment, most likely due to the fact that they are both ASS-positive and ASL-positive.

Table 11f shows that the lung cancer cell line A549 tested was sensitive to arginase treatments. These cancer cells tested were OTC-negative. It is also sensitive to ADI treatment, most likely due to the fact that they are either ASS-negative or ASL-negative. In contrast, also shown in Table 11f, all the cervical cancer cell lines tested were sensitive to arginase treatments (they were all OTC-negative), but only 2 cervical cancer cell line (SiHa and C-33A) tested were sensitive and the other 3 (HeLa, ME180, CC3) were resistant to ADI treatment, most likely due to the fact that they are both ASS-positive and ASL-positive.

The results for breast cancel cells are shown in Table 11g. As it shown, all the breast cancer cell lines tested were sensitive to arginase treatments (they were all OTC-negative). Strikingly, only one breast cancer cell line (MDA-MB-231) tested was sensitive and the other 3 (MCF-7, ZR-75-1, Hs578T) were resistant to ADI treatments.

Also shown in Table 11g are results for the prostate cancer cell line, which was found to be sensitive to both arginase and ADI treatments. As discussed above, such results can be explained by the fact that this cell line is both OTC-negative and ASS-negative.

TABLE 11a

| Type of cancer | Cell line name (medium, source) | BCA U/mL (μg/mL) | HAI U/mL (μg/mL) | rhArg U/mL (μg/mL) | ADI U/mL (μg/mL) | ARG | OTC | ASS | ASL |
|---|---|---|---|---|---|---|---|---|---|
| melanoma | SK-mel-2 (EMEM 10% FBS, 1% PS ATCC) | 0.612 (11.25) | 0.079 (0.80) | 0.0556 (1.31) | 0.0022 (0.082) | − | − | + L | + |
| | SK-mel-24 (EMEM 10% FBS, 1% PS NCI) | | | 0.204 (4.82) | 0.012 (0.45) | − | − | + L | + |
| | SK-mel-28 (EMEM 10% FBS, 1% PS ATCC) | 0.91 (16.72) | 0.064 (0.65) | 0.0523 (1.233) | 0.00084 (0.031) | − | − | + L | + |
| | A375 (DMEM 10% FBS, 1% PS ATCC) | 0.15 (2.76) | 0.061 (0.62) | 0.0288 (0.679) | 0.00059 (0.022) | − | − | + L | + |
| | B16 (DMEM 10% FBS, 1% PS ATCC) | | | 0.02 (0.48) | 0.004 (0.11) | − | − | + L | + |

TABLE 11b

| Type of cancer | Cell line name (medium, source) | BCA U/mL (μg/mL) | HAI U/mL (μg/mL) | rhArg U/mL (μg/mL) | ADI U/mL (μg/mL) | ARG | OTC | ASS | ASL |
|---|---|---|---|---|---|---|---|---|---|
| leukemia | HL60 (RPMI 10% FBS, 1% PS ATCC) | | | 0.03 (0.679) | 0.016 (0.591) | + | − | − | + |
| | K562 (RPMI 20% FBS, 1% PS ATCC) | | | 0.06 (1.357) | 0.003 (0.085) | − | − | + | − |
| | RPMI8226 (RPMI 10% FBS, 1% PS ATCC) | | | 0.09 (2.036) | R | | | | |
| | Jurkat (RPMI 10% FBS, 1% PS ATCC) | 0.41 (7.54) | | 0.037 (0.86) | 0.002 (0.074) | | | | |

TABLE 11c

| Type of cancer | Cell line name (medium, source) | BCA U/mL (μg/mL) | HAI U/mL (μg/mL) | rhArg U/mL (μg/mL) | ADI U/mL (μg/mL) | ARG | OTC | ASS | ASL |
|---|---|---|---|---|---|---|---|---|---|
| colorectal | (WiDr DMEM 10% FBS, 1% PS ATCC) | 0.215 (3.96) | 0.075 (0.76) | 0.038 (0.84) | 0.035 (0.9) | + | − | + | − |
| | SW1116 (RPMI 10% FBS, 1% PS ATCC) | 1.417 (20.98) | 0.41 (4.18) | 0.15 (3.394) | R | + | − | + | + |
| | HT29 (DMEM 10% FBS, 1% PS ATCC) | 0.231 (4.24) | | 0.03 (0.679) | 0.032 (0.83) | + | − | + L | + |
| | HCT15 (RPMI 10% FBS, 1% PS ATCC) | | 0.63 (6.44) | 0.083 (1.043) | R | + | − | + | + |
| pancreatic | Panc1 (DMEM 10% FBS, 1% PS ATCC) | 0.263 (4.84) | | 0.09 (2.036) | 0.049 (1.39) | − | − | + L | + |
| | BxPC3 | 0.846 | | 0.08 | R | + | − | + | + |

TABLE 11c-continued

| Type of cancer | Cell line name (medium, source) | BCA U/mL (μg/mL) | HAI U/mL (μg/mL) | rhArg U/mL (μg/mL) | ADI U/mL (μg/mL) | ARG | OTC | ASS | ASL |
|---|---|---|---|---|---|---|---|---|---|
| | (EMEM 10% FBS, 1% PS ATCC) | (15.54) | | (1.809) | | | | | |
| | HPAFII (DMEM 10% FBS, 1% PS ATCC) | | | 0.86 (19.35) | | R | − | − | + | + |

TABLE 11d

| Type of cancer | Cell line name (medium, source) | BCA U/mL (μg/mL) | HAI U/mL (μg/mL) | rhArg U/mL (μg/mL) | ADI U/mL (μg/mL) | ARG | OTC | ASS | ASL |
|---|---|---|---|---|---|---|---|---|---|
| gastric | AGS (RPMI 10% FBS, 1% PS ATCC) | 0.662 (12.17) | | 0.10 (2.262) | | R | − | − | + | + |
| | MKN45 (RPMI 10% FBS, 1% PS Riken Cell bank, Japan) | 0.798 (14.67) | | 0.79 (17.873) | | R | − | − | + | + |
| | BCG-823 (RPMI 10% FBS, 1% PS Beijing Institute of Cancer Research) | | | 0.11 (2.457) | | R | − | − | + | + |

TABLE 11e

| Type of cancer | Cell line name (medium, source) | BCA U/mL (μg/mL) | HAI U/mL (μg/mL) | rhArg U/mL (μg/mL) | ADI U/mL (μg/mL) | ARG | OTC | ASS | ASL |
|---|---|---|---|---|---|---|---|---|---|
| HCC (liver cancer) | PLC/PRF/5 (DMEM 10% FBS, 1% PS ATCC) | 2.376 (43.67) | 0.94 (9.56) | 0.312 (7.07) | | R | + | − | + | + |
| | Hep3B (DMEM 10% FBS, 1% PS ATCC) | 9.1 (57.68) | 0.29 (2.95) | 0.65 (15.0) | | R | + | − | + | + |
| | HepG2 (DMEM 10% FBS, 1% PS ATCC) | 2.002 (36.79) | 0.097 (0.99) | 0.177 (4.00) | | R | + | − | + | + |
| | Huh7 (DMEM 10% FBS, 1% PS ATCC) | | | 1.59 (43) | | R | + | − | + | + |
| | SK-HEP-1 (DMEM 10% FBS, 1% PS ATCC) | 12.27 (77.79) | 1.725 (6.05) | 0.15 (4) | 0.007 (0.2) | − | − | + L | + |
| retinoblastoma | Y79 (RPMI 10% FBS, 1% PS ATCC) | | | 0.5 (11.3) | | R | − | − | + | + |

TABLE 11f

| Type of cancer | Cell line name (medium, source) | BCA U/mL (μg/mL) | HAI U/mL (μg/mL) | rhArg U/mL (μg/mL) | ADI U/mL (μg/mL) | ARG | OTC | ASS | ASL |
|---|---|---|---|---|---|---|---|---|---|
| lung | A549 (DMEM 10% FBS, 1% PS ATCC) | 0.3294 (2.09) | | 0.035 (0.44) | 0.011 (0.29) | − | − | − | + |

TABLE 11f-continued

| Type of cancer | Cell line name (medium, source) | BCA U/mL (μg/mL) | HAI U/mL (μg/mL) | rhArg U/mL (μg/mL) | ADI U/mL (μg/mL) | ARG | OTC | ASS | ASL |
|---|---|---|---|---|---|---|---|---|---|
| Cervical | HeLa (DMEM 10% FBS, 1% PS ATCC) | 0.719 (13.21) | 0.366 (3.72) | 0.065 (0.82) | R | – | – | + | + |
| | ME180 (DMEM 10% FBS, 1% PS ATCC) | 1.42 (26.16) | 0.214 (2.18) | 0.153 (1.93) | R | – | – | + | + |
| | CC3 (DMEM 10% FBS, 1% PS ATCC) | 0.84 (15.50) | | 0.42 (5.29) | R | – | – | + | + |
| | SiHa (DMEM 10% FBS, 1% PS ATCC) | 0.32 (5.84) | 0.024 (0.24) | 0.03 (0.38) | 0.0025 (0.064) | – | – | – | + |
| | C-33A (DMEM 10% FBS, 1% PS ATCC) | 0.19 (3.55) | 0.033 (0.34) | 0.058 (0.72) | 0.0014 (0.036) | – | – | – | + |

TABLE 11g

| Type of cancer | Cell line name (medium, source) | BCA U/mL (μg/mL) | HAI U/mL (μg/mL) | rhArg U/mL (μg/mL) | ADI U/mL (μg/mL) | ARG | OTC | ASS | ASL |
|---|---|---|---|---|---|---|---|---|---|
| breast | MCF-7 (EMEM 10% FBS, 1% PS ATCC) | 0.05 (0.91) | | 0.28 (6.36) | R | – | – | + | + |
| | ZR-75-1 (DMEM 10% FBS, 1% PS ATCC) | | | 0.14 (3.18) | R | – | – | + | + |
| | Hs578T (DMEM 10% FBS, 1% PS, 10 g/ml insulin NCI) | | | 3.75 (85.2) | | | – | + | + |
| | MDA-MB-231 (DMEM 10% FBS, 1% PS NCI) | 0.22 (4.11) | 0.273 | 0.44 (10.0) | 0.16 (5.93) | – | – | +L | + |
| | 4T1 | 0.68 | 0.058 | 0.023 (0.29) | 0.0007 (0.017) | | | | |
| Prostate | PC3 (DMEM 10% FBS, 1% PS ATCC) | 0.263 (4.84) | 0.40 (4.07) | 0.08 (1.47) | 0.0025 (0.064) | – | – | – | + |
| | LNCap (EMEM 10% FBS, 1% PS ATCC) | 2.119 (38.94) | 0.47 (4.78) | 0.41 (5.16) | 0.13 (3.34) | | | | |

For Table 11, "+"=mRNA was detected by RT-PCR, indicating the corresponding gene is expressed; "–"=mRNA was not detected by RT-PCR, indicating the gene is not expressed; "R" indicates that the cell line is ADI-resistant and the $IC_{50}$ value cannot be estimated; and "L" indicates that the cell line has a relatively low level of ASS expression and therefore the cell line is still ADI-sensitive.

Figure 18:
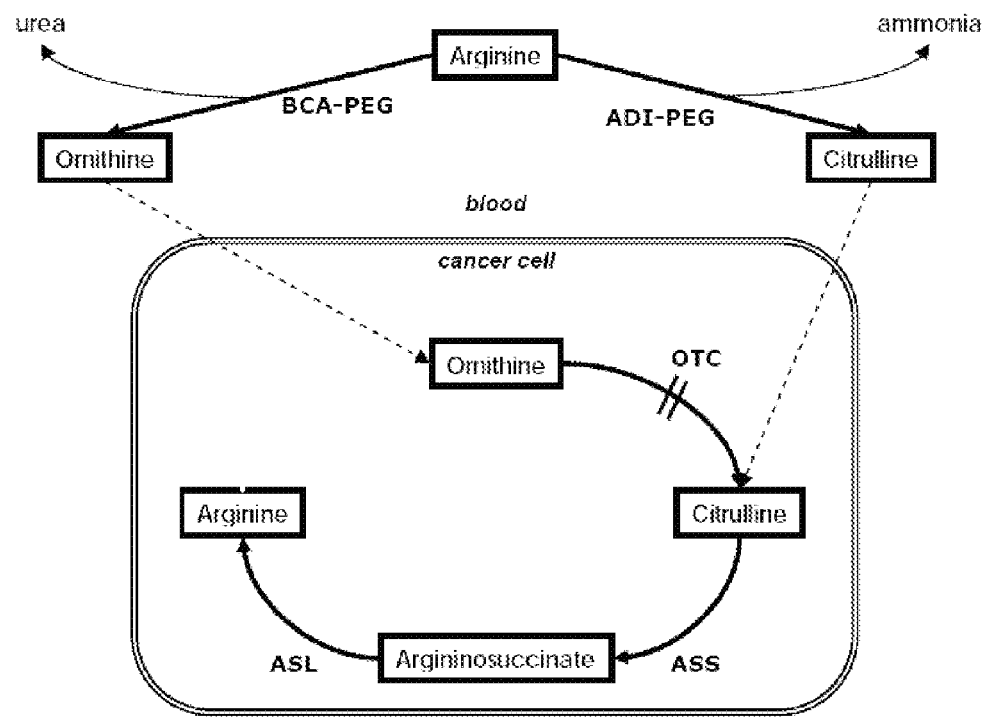
FIG. 18 illustrates a hypothesis and working model for cancer cells that are OTC-negative.

While not wish to be bound by the following hypothesis and working models, applicants believe the following hypothesis and working models are consistent with the experimental data of the present invention and thus are useful guides for further utilization of the inventions disclosed herewith (also see FIG. 18).

Hypothesis and working models explaining why OTC-negative cancer cells are arginase-sensitive but can be ADI-resistant. When arginase is added in the culture medium or pegylated arginase is injected in the blood (in the body), arginine is converted into ornithine and urea by the arginase enzymatic reaction. Ornithine formed then passes into the cancer cells. Unlike normal cells, cancer cells grow rapidly and require much more arginine than normal cells for protein synthesis and other cellular processes. If the cancer cells are OTC-positive, ASS-positive and ASL-positive, ornithine can be recycled back into arginine. Therefore, cancer cells still have arginine and they are not arginine-deficient and cancer growth is not inhibited. On the other hand, cancer cells that are OTC-negative or ASS-negative or ASL-negative or any combination of these deficiencies or low expression level of any of these genes, the synthesis (or recycle) pathway from ornithine to arginine is blocked and therefore cancer cells are lack of arginine and cancer cell growth is thus inhibited and cancer cell death may occur.

Hypothesis and working models for liver cancer cells that are OTC-negative. Model relating urea cycle gene expression and resistance towards pegylated arginine deiminase (ADI-PEG) and pegylated *Bacillus caldovelox* arginase (BCA-PEG20). Liver cancer cells express the urea cycle enzymes argininosuccinate synthetase (ASS), argininosuccinate lyase (ASL) and arginase (ARG), but lack ornithine transcarbamylase (OTC). BCA-PEG20 in the bloodstream depletes arginine and produces ornithine, which enters the cell but fails to be recycled via the urea cycle owing to the absence of OTC. ADI-PEG converts arginine to citrulline, which can be readily converted back to arginine by ASS and ASL after uptake into liver cancer cells. Therefore, in this model, the liver cancer cells are sensitive to BCA-PEG20 treatment (inhibited by BCA-PEG20) but resistant to ADI-PEG treatment.

Hypothesis and working models for cancer cells that are OTC-negative. Model relating gene expression in cancer cells and resistance towards pegylated arginine deiminase (ADI-PEG) and pegylated *Bacillus caldovelox* arginase (BCA-PEG20). For cancer cells that do not express arginase (ARG), cancer cells express the enzymes argininosuccinate synthetase (ASS), argininosuccinate lyase (ASL), but lack ornithine transcarbamylase (OTC). BCA-PEG20 in the bloodstream depletes arginine and produces ornithine, which enters the cell but fails to be recycled owing to the absence of OTC. ADI-PEG converts arginine to citrulline, which can be readily converted back to arginine by ASS and ASL after uptake into the cancer cells. Therefore, in this model, the cancer cells are sensitive to BCA-PEG20 treatment (inhibited by BCA-PEG20) but resistant to ADI-PEG treatment. This model can be applied to cancer cells in general.

Method of Further Enhance Arginase Activity by Using Cobalt as Metal Cofactor

The native metal cofactor of arginase is manganese ($Mn^{2+}$). It is surprisingly discovered by the present invention that replacing the manganese with cobalt dramatically enhances the enzyme's activity. Either *Bacillus caldovelox* arginase (BCA) or the human arginase I (HAI) was expressed as described previously. The purification method was the same as described before except 10 mM of metal ion ($CoSO_4$ or $MnSO_4$) was added into the purified protein elution from Nickel affinity chromatography instead of added before Nickel affinity chromatography. Eluted factions containing the arginase enzyme were incubated with 10 mM metal for 15 min at 50~55° C., followed by filtration through a 0.45 μm syringe filter. Then the solution was exchanged with storage buffer by ultrafiltration.

Figure 16:
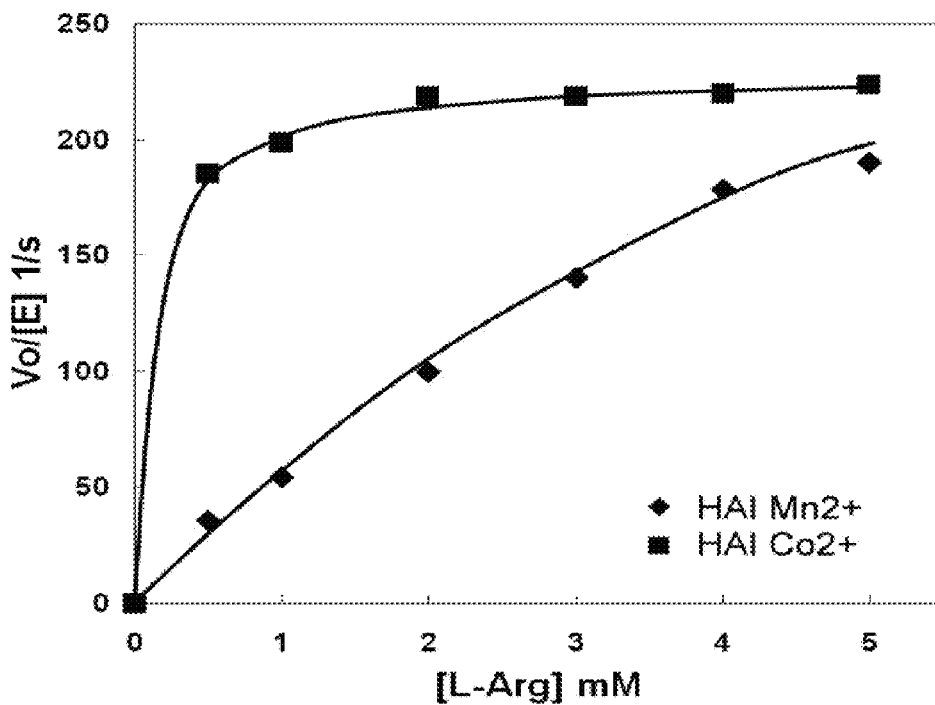
FIG. 16 shows a comparison of steady-state kinetics of human arginase I with different metal cofactors, i.e., $Mn^{2+}$ and $Co^{2+}$.

Diacetylmonoxine (DAMO) assay was used to determine the kinetic parameters of human arginase with different metal cofactors. All enzymatic reactions were carried out at pH 7.4. The results are shown in FIG. 16. The steady-state kinetics of recombinant human arginase I (HAI) or huArg substituted with $Mn^{2+}$ or $Co^{2+}$ were measured in sodium phosphate buffer pH 7.4, 25° C. The Km of HAI with $Mn^{2+}$ (HAI $Mn^{2+}$) or huArg $Mn^{2+}$ and HAI with $Co^{2+}$ (HAI $Co^{2+}$) or huArg $Co^{2+}$ are 1.83 mM and 0.19 mM respectively. Since the Km value is improved about 10-fold in HAI $Co^{2+}$ or huArg $Co^{2+}$, its specific activity is improved 10-fold and is a much more efficient drug to deplete arginine than HAI $Mn^{2+}$ or huArg $Mn^{2+}$.

Enhancing Arginase Activity by Further Modifying Genetic Modification

Figure 17:
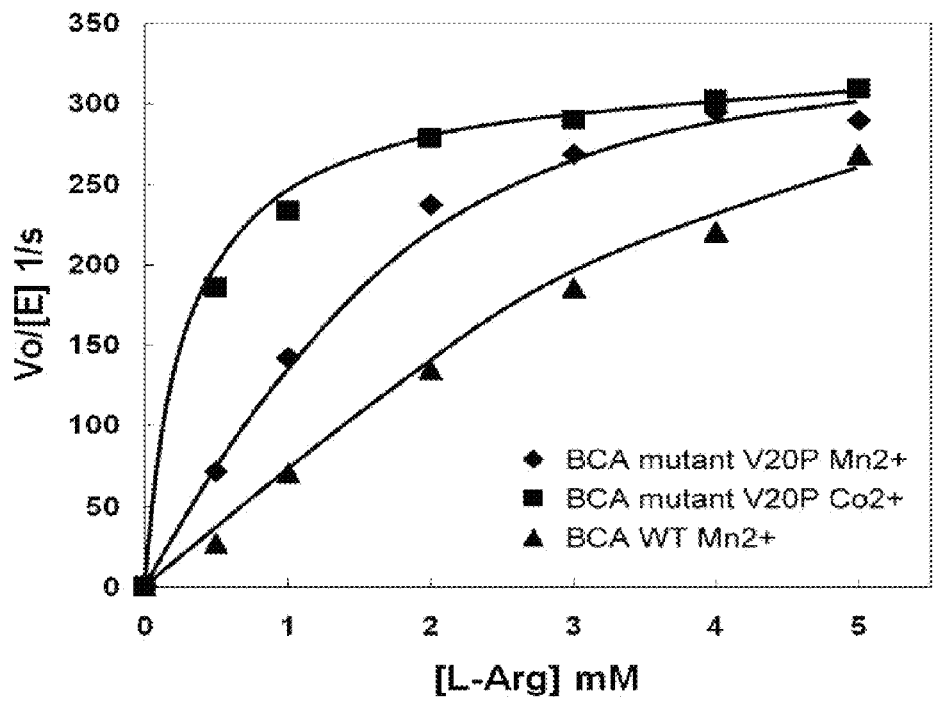
FIG. 17 shows a comparison of steady-state kinetics of the V20P mutant of Bacillus caldovelox arginase (BCA) and the wild-type BCA substituted with $Mn^{2+}$ ($BCAWTMn^{2+}$) or $Co^{2+}$.

It is surprisingly discovered by the present invention that the position 20 of BCA can be substituted with other amino acids to improve enzyme activity. The $20^{th}$ amino acid residue valine in the wild-type sequence was substituted with proline (or any other amino acids for example serine or glycine, which improves the specific activity of BCA) by site directed mutagenesis (for example codon GTT [valine] to CCG [proline]). The mutant genes were cloned, expressed and purified for detailed studies. An exemplary such mutant enzyme was made by replacing valine with proline, referred to as "BCA mutant V20P" or "bcArg V20P mutant". Steady-state kinetics of the BCA mutant V20P and BCA with $Mn^{2+}$ or $Co^{2+}$ were measured in sodium phosphate buffer pH 7.4, 25° C. and were shown in FIG. 17. The Km values of BCA mutant V20P with $Mn^{2+}$ (BCA mutant V20P $Mn^{2+}$) and BCA mutant V20P with $Co^{2+}$ (BCA mutant V20P $Co^{2+}$) are about 1.29 mM and 0.18 mM respectively. The Km of BCA with $Mn^{2+}$ (BCAW-T$Mn^{2+}$) is about 3.2 mM. Therefore, the BCA mutant V20P with $Co^{2+}$ as cofactor [Km=0.18 mM] is a much more efficient drug to deplete arginine than the BCA (BCAWT$Mn^{2+}$) [Km=3.2 mM].

In Vitro Cancer Cell Line Studies Using BCA Mutant V20P

Cell proliferation assay was conducted as follows.

$2.5 \times 10^3$ Sk-mel-28 (EMEM), $5 \times 10^3$ HEK293 (EMEM), MCF-7 (EMEM), HCT-15 (RPMI), Hep3B (DMEM), PANC-1 (DMEM), Hela (DMEM) and A549 (DMEM) cells were seeded to each well of a 96-well plate in 100 μL culture medium and were allowed to adhere to the plate overnight. On the next day, the culture medium was replaced with medium containing different concentrations of BCA and BCA mutant V20P protein drug. $2 \times 10^4$ Jurkat (RPMI) floating cells were seeded to each well of a 96-well plate in 50 μL culture medium at the day of adding protein drug and different concentrations of protein drug in 50 μL were added directly to each well. The cells were allowed to incubate for an additional 3 days at 37° C. in an atmosphere of 95% air/5% $CO_2$. MTT cell proliferation assay (Invitrogen) was then performed to estimate the number of viable cells in the culture. In brief, 10 μL of 5 mg/mL of water-soluble MTT regents was added to 100 μL culture medium and incubated at 37° C. for 4 h. MTT is chemically reduced by cells into purple formazan, which is then dissolved by acidified SDS (0.01 N HCl in 10% SDS) in tissue culture medium. Concentration of the cleavage product formazan was then measured by reading its absorbance with a spectrophotometer with a 570 nm filter. Cell proliferation data were expressed as a percentage of control. Non-linear regression was used to fit a sigmoidal dose response curve with Prism 4.0 (Graphpad Software), and the amount of protein drug needed to achieve 50% cell growth inhibition was defined as $IC_{50}$. The results are shown in Table 12. The corresponding enzymatic activities are shown in Table 13.

TABLE 12

$IC_{50}$ of BCA and BCA mutant V20P in different kinds of cancer cells

| | | $IC_{50}$ Value | | | | Fold of Difference | |
| | | BCA | | BCA mutant V20P | | (BCA/BCA mutant V20P) | |
| | | (U/mL) | (mg/mL) | (U/mL) | (mg/mL) | (U/mL) | (mg/mL) |
|---|---|---|---|---|---|---|---|
| HCT-15 | Colon | 15.62 | 0.0916 | 7.34 | 0.0132 | 2.13 | 6.96 |
| Jurkat | Leukemia | 6.84 | 0.0401 | 0.90 | 0.0016 | 7.60 | 24.85 |
| MCF-7 | Breast | 5.51 | 0.0323 | 2.87 | 0.0051 | 1.92 | 6.28 |
| sk-mel-28 | Melanoma | 3.35 | 0.0197 | 1.52 | 0.0027 | 2.20 | 7.21 |
| HEK293 | Kidney | 3.86 | 0.0226 | 3.40 | 0.0061 | 1.14 | 3.71 |
| A549 | Lung | 2.67 | 0.0157 | 1.64 | 0.0029 | 1.63 | 5.32 |
| Hep3B | Liver | 9.42 | 0.0552 | 9.43 | 0.0169 | 1.00 | 3.27 |
| Hela | Cervical | 2.83 | 0.0166 | 1.37 | 0.0025 | 2.07 | 6.75 |
| PANC-1 | Pancreatic | 1.20 | 0.0070 | 0.87 | 0.0016 | 1.38 | 4.51 |

TABLE 13

Specific activity of the proteins

| | Protein concentration (mg/mL) | Specific activity (U/mg) | Enzyme activity (U/mL) |
|---|---|---|---|
| BCA | 3.046 | 170.47 | 519.3 |
| BCA mutant V20P | 2.63 | 557.3 | 1465.7 |

The results show that BCA mutant V20P is much more efficient in killing various types of cancer cells in in vitro drug efficacy studies.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A pharmaceutical composition for treating an arginine-dependent disease comprising a polyethylene glycol-arginase conjugate having a polyethylene glycol moiety covalently attached to a genetically-modified human arginase, wherein said genetically-modified human arginase has a single amino acid position for covalently attaching to the polyethylene glycol moiety, wherein said polyethylene glycol-arginase conjugate has a serum circulation half-life higher than the serum circulation half-life of pure, unmodified human arginase, wherein said polyethylene glycol-arginase conjugate has decreased immunogenicity compared to the immunogenicity of pure, unmodified human arginase, wherein said single amino acid position is sufficiently far from the active site of the genetically-modified human arginase such that the polyethylene glycol attachment does not interfere with the active site, wherein the genetically-modified human arginase comprises SEQ ID NO: 6 and the single amino acid position for the attachment of polyethylene glycol is position 45 of SEQ ID NO: 6 ($Cys^{45}$).

2. A pharmaceutical composition for treating an arginine-dependent disease comprising a polyethylene glycol-arginase conjugate having a polyethylene glycol moiety covalently attached to a genetically-modified *Bacillus caldovelox* arginase, wherein said genetically-modified *Bacillus caldovelox* arginase has a single amino acid position for covalently attaching to the polyethylene glycol moiety, wherein said polyethylene glycol-arginase conjugate has a serum circulation half-life higher than the serum circulation half-life of pure, unmodified *Bacillus caldovelox* arginase, wherein said polyethylene glycol-arginase conjugate has decreased immunogenicity compared to the immunogenicity of pure, unmodified *Bacillus caldovelox* arginase, wherein said single amino acid position is sufficiently far from the active site of the genetically-modified *Bacillus caldovelox* arginase such that the polyethylene glycol attachment does not interfere with the active site, wherein the genetically-modified *Bacillus caldovelox* arginase comprises SEQ ID NO: 8 and the single amino acid position for the attachment of polyethylene glycol is position 161 of SEQ ID NO: 8 ($Cys^{161}$).

3. The pharmaceutical composition of claim 1 wherein the ratio of said polyethylene glycol moiety to the genetically-modified human arginase is substantially one.

4. The pharmaceutical composition of claim 2 wherein the ratio of said polyethylene glycol moiety to the genetically modified *Bacillus caldovelox* arginase is substantially one.

5. The pharmaceutical composition of claim 1 wherein the polyethylene glycol is a single chain or branched chain polyethylene glycol.

6. The pharmaceutical composition of claim 2 wherein the polyethylene glycol is a single chain or branched chain polyethylene glycol.

7. The pharmaceutical composition of claim 1 further comprising a pharmaceutically acceptable carrier, excipient, or auxiliary agent.

8. The pharmaceutical composition of claim 2 further comprising a pharmaceutically acceptable carrier, excipient, or auxiliary agent.

9. The pharmaceutical composition of claim 1 wherein the arginine-dependent disease is an arginine-dependent cancer or a viral infection by a virus selected from HIV, hepatitis B, and hepatitis C.

10. The pharmaceutical composition of claim 2 wherein the arginine-dependent disease is an arginine-dependent cancer or a viral infection by a virus selected from HIV, hepatitis B, and hepatitis C.

* * * * *